(12) United States Patent
Bley et al.

(10) Patent No.: US 6,472,536 B1
(45) Date of Patent: Oct. 29, 2002

(54) 2-(SUBSTITUTED-PHENYL)AMINO-IMIDAZOLINE DERIVATIVES

(75) Inventors: Keith Roger Bley, Mountain View; Robin Douglas Clark, Palo Alto; Alam Jahangir, San Jose; Bruce Andrew Kowalczyk, Redwood City; Francisco Javier Lopez-Tapia, Fremont; Alexander Victor Muehldorf; Counde O'Yang, both of Sunnyvale; Thomas Weitao Sun, Fremont, all of CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 2 days.

(21) Appl. No.: 09/666,065

(22) Filed: Sep. 19, 2000

Related U.S. Application Data

(62) Division of application No. 09/137,507, filed on Aug. 20, 1998, now Pat. No. 6,184,242.
(60) Provisional application No. 60/089,916, filed on Jun. 19, 1998, provisional application No. 60/088,015, filed on Jun. 4, 1998, and provisional application No. 60/057,808, filed on Sep. 4, 1997.

(51) Int. Cl.[7] ............................................. C07D 233/50
(52) U.S. Cl. ................................................... 548/311.1
(58) Field of Search ..................................... 548/311.1

(56) References Cited

U.S. PATENT DOCUMENTS

| 3,931,216 A | 1/1976 | Franzmair |
| 4,287,201 A | 9/1981 | Olson et al. |
| 4,374,143 A | 2/1983 | Dolman |
| 4,396,617 A | 8/1983 | Dolman et al. |
| 4,588,737 A | 5/1986 | Huang |
| 4,889,868 A | 12/1989 | Huang |
| 5,326,776 A | 7/1994 | Winn et al. |

FOREIGN PATENT DOCUMENTS

| EP | 0017484 B1 | 4/1983 |
| EP | 0187989 A1 | 7/1986 |
| GB | 2038305 | 7/1980 |
| WO | WO 96/30350 | 10/1996 |

OTHER PUBLICATIONS

K. Anderson, *Pharmacological Reviews* 1993 45(3), 253–308.
Byrn et al., *Pharmaceutical Research* 1995, 12(7), 945–954.
*Goodman & Gillman's, the Pharmacological Basis of Therapeutics*, 9th Edition, McGraw–Hill, New York, 1996, Chapter 26, 601–616.
Murata et al., *Nature* 1997, 388, 678–682.

*Primary Examiner*—Patricia L. Morris
(74) *Attorney, Agent, or Firm*—Janet Kaku; Gloria Pfister

(57) ABSTRACT

This invention relates to IP receptor antagonists selected from the group of compounds represented by Formula I:

where:

$R^1$ is a group represented by formula (A), (B) or (C);

and other substituents as defined in the specification, and their pharmaceutically acceptable salts or crystal forms thereof; and pharmaceutical compositions containing them; and methods for their use as therapeutic agents.

9 Claims, 2 Drawing Sheets

2-(SUBSTITUTED-PHENYL)AMINO-IMIDAZOLINE DERIVATIVES

CROSS REFERENCE TO RELATED APPLICATIONS

This is a division of patent application Ser. No. 09/137,507, filed on Aug. 20, 1998, now U.S. Pat. No. 6,184,242, which in turn claims the benefit under 35 U.S.C. 119(e) to prior U.S. Provisional Application Nos. 60/089,916, filed Jun. 19, 1998; 60/088,015, filed Jun. 4, 1998; and 60/057,808, filed Sep. 4, 1997.

BACKGROUND OF THE INVENTION

1. Field of the Invention

This invention relates to IP receptor antagonists, especially to certain 2-(substituted-phenyl)amino-imidazoline derivatives; pharmaceutical compositions containing them; and methods for their use as therapeutic agents.

2. Background Information and Related Disclosures

Prostaglandins or prostanoids (PG) are a group of biologically active compounds derived from membrane phospholids and are formed from certain polyunsaturated fatty acids. They fall into several main classes designated by letters including D, E, F, G, H, and I (prostacyclin). The main classes are further subdivided as indicated by subscripts 1, 2, or 3, which reflect the fatty acid precursor, for example $PGE_1$ or $PGE_2$. Prostanoids are ubiquitously produced and the rate of their production usually increases in response to diverse stimuli. They thereby exhibit a wide variety of pharmacological properties.

The diversity of effects of prostanoids can be explained by the existence of a number of distinct receptors that mediate their action. The receptors have been named for the natural prostaglandin for which they have the greatest affinity and have been divided into five main types, designated as DP ($PGD_2$), FP ($PG_{2\alpha}$), IP ($PGI_2$), TP ($TXA_2$), AND EP ($PGE_2$). Additional information relating to prostaglandins and their receptors are described in *Goodman & Gillman's, The Pharmacological Basis of Therapeutics*, ninth edition, McGraw-Hill, New York, 1996, Chapter 26, pages 601–616.

Prostanoids are generated by most cells in response to mechanical, thermal or chemical injury and inflammatory insult, and are responsible for the sensitization or direct activation of nearby sensory nerve endings. The hyperalgesic effects (an increased responsiveness to a stimulus that is normally painful) of several prostanoids have been reported in several inflammatory models of nociception. Even though $PGE_2$ has attained wide recognition as the primary mediator of hyperalgesia, significant quantities of other prostanoids, including $PGI_2$, are released by injury or inflammation. Indeed, when the effects of $PGE_2$ and $PGI_2$ on sensory neurons are compared directly, $PGI_2$ is equally or more effective as a hyperalgesic or sensitizing agent both in vivo and in vitro assays. However, to date, there have been no selective receptor antagonists which could unequivocally characterize the prostanoid receptor subtype(s) that mediate the sensitizing effects of $PGE_2$ or $PGI_2$.

When the intrinsic instability and pharmacokinetic properties of $PGI_2$ are taken into account, a preponderance of in vivo analgesia studies in rodents suggest that $PGI_2$ plays a major role in the induction of hyperalgesia. Likewise, in vitro studies provide substantial evidence to suggest that IP receptors act as important modulators of sensory neuron function. Since IP receptors in sensory neurons are coupled to activation of both adenylyl cyclase and phospholipase C, and hence, cAMP-dependent protein kinase and protein kinase C, these receptors can exert powerful effects on ion channel activity and thus neurotransmitter release.

Recent compelling evidence for a prominent role for IP ($PGI_2$-preferring) receptors in inflammatory pain has been obtained from recent studies in transgenic mice lacking the IP receptor (T. Murata et al., *Nature* 1997, 388, 678–682). In these animals, the acetic acid-induced writhing response or the carrageenan-induced paw edema was reduced to levels similar to those seen with administration of indomethacin in wild-type mice. In contrast, spinal nociceptive reflexes measured by the tail-flick and hot-plate test were normal. The modest writhing response induced by $PGE_2$ was unchanged in the transgenic animals.

Based upon these observations, the compounds of the present invention are expected to be effective antinociceptive agents.

In addition to being mediators of hyperalgesia, prostanoids are known to be generated locally in the bladder in response to physiologic stimuli such as stretch of the detrusor smooth muscle, injuries of the vesical mucosa, and nerve stimulation (K. Anderson, *Pharmacological Reviews* 1993, 45(3), 253–308). $PGI_2$ is the major prostanoid released from the human bladder. Several lines of evidence suggest that prostanoids may be the link between detrusor muscle stretch produced by bladder filling and activation of C-fiber afferents by bladder distension. It has been proposed that prostanoids may be involved in the pathophysiology of bladder disorders, e.g., bladder outlet obstruction, and conditions associated with urinary incontinence such as urge incontinence, stress incontinence, and bladder hyperreactivity. Therefore, antagonists of prostanoid IP receptors are expected to be useful in the treatment of such conditions.

Certain 2-(substituted-phenyl)amino-imidazoline compounds have been exemplified in the patent literature. For example, European Patent No. 0 017 484 B1 (Fujisawa Pharmaceutical) discloses compounds useful for treatment of hypertensive, inflammatory and gastrointestinal disorder and relief from pain of various origins; U.S. Pat. No. 4,287,201 (Olson et al.) discloses compounds useful in delaying the onset of egg production in young pullets, interrupting egg production in mature hens, and in producing an artificial molt; U.S. Pat. No. 4,396,617 (Dolman and Kuipers) discloses fungicides active against rust of beans, brown rust of wheat and mildew on cereals; U.S. Pat. No. 4,889,868 (Huang) discloses lipoxygenase and phospholipase C inhibitors and platelet-activating factor receptor antagonists useful for the treatment of inflammatory or allergic conditions and myocardial infarctions; U.S. Pat. No. 5,326, 776 (Winn et al.) discloses compounds that are angiotensin II receptor antagonists; British Patent Application No. GB 2 038 305 (Duphar International Research) discloses compounds that can be used to inhibit growth of side shoots tobacco or tomato plants, or inhibit lawn growth, or dwarf ornamental plants; and PCT Published Application No. WO 96/30350 (Fujisawa Pharmaceutical) discloses compounds useful as a medicament for prophylactic and therapeutic treatment of nitric oxide synthase-mediated diseases.

The disclosures of these and other documents referred to throughout this application are incorporated herein by reference.

SUMMARY OF THE INVENTION

This invention provides compounds represented by Formula I:

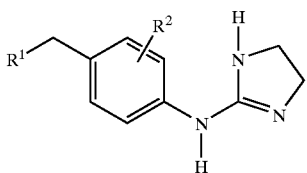

wherein:
R¹ is a group represented by formula (A), (B) or (C);

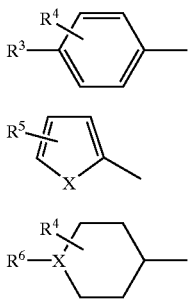

wherein:
X is independently in each occurrence S, O or N;
$R^2$ and $R^4$ are each independently in each occurrence:
  (1) hydrogen,
  (2) alkyloxy, or
  (3) halogen;
$R^3$ is independently in each occurrence:
  (1) alkyl,
  (2) cycloalkyl,
  (3) halogen,
  (4) heterocyclyl,
  (5) —$NR^8R^9$,
  (6) —$(CH_2)_m CONR^8R^9$, wherein m is an integer from 0 to 3,
  (7) —$(CH_2)_m SO_2NR^8R^9$, wherein m is an integer from 0 to 3,
  (8) —$(CH_2)_m NR^7COR^9$, wherein m is an integer from 0 to 3,
  (9) —$(CH_2)_m NR^7SO_2R^9$, wherein m is an integer from 0 to 3,
  (10) —$(CH_2)_m NR^7C(V)NR^8R^9$, wherein V is S or O, and m is an integer from 0 to 3,
  (11) —$(CH_2)_m OY$ wherein m is an integer from 0 to 3, and Y is:
    hydrogen, alkyl, alkyloxyalkyl, cycloalkyl, haloalkyl, hydroxyalkyl, heterocyclyl, or carboxyalkyl, or
  (12) —$O(CH_2)_n Z$ wherein n is an integer from 1 to 4 and Z is:
    cycloalkyl, hydroxyalkyl, cycloalkyloxy, heterocyclyl, aryloxy, heteroaryl, —$COR^9$, —$CCNR^8R^9$, —$SO_2R^9$, —$SO_2NR^8R^9$, —$NR^7SO_2R^9$, or unsubstituted aryl or mono-, di-, or tri-substituted aryl, the substituents being independently selected from alkyl, halogen, or alkyloxy;
$R^5$ is independently in each occurrence:
  (1) —$(CH_2)_m OY$ wherein m is an integer from 0 to 3, and Y is:
    hydrogen, alkyl, alkyloxyalkyl, cycloalkyl, haloalkyl, hydroxyalkyl, heterocyclyl, or carboxyalkyl, or
  (2) —$O(CH_2)_n Z$ wherein n is an integer from 1 to 4, and Z is:
    cycloalkyl, hydroxyalkyl, cycloalkyloxy, heterocyclyl, aryloxy, heteroaryl, —$COR^9$, —$CONR^8R^9$, —$SO_2R^9$, —$SO_2NR^8R^9$, or —$NR^7SO_2R^9$, or unsubstituted aryl or mono-, di- or tri-substituted aryl, the substituents being independently selected from alkyl, halogen, or alkyloxy;
$R^6$ is independently in each occurrence:
  (1) hydrogen,
  (2) —$COR^9$,
  (3) —$CONR8R^9$,
  (4) —$C(V)NR^8R^9$ wherein V is O or S,
  (5) —$SO_2R^9$, or
  (6) —$SO_2NR^8R^9$;
$R^7$ and $R^8$ are each independently in each occurrence:
  (1) hydrogen,
  (2) alkyl, or
  (3) hydroxyalkyl;
$R^9$ is independently in each occurrence:
  (1) alkyl,
  (2) cycloalkyl,
  (3) arylalkyl,
  (4) hydroxyalkyl,
  (5) haloalkyl,
  (6) heterocyclyl,
  (7) unsubstituted aryl or mono-, di-, or tri-substituted aryl, the substituents being independently selected from alkyl, halogen, or alkyloxy, or
  (8) heteroaryl;
or $R^8$ and $R^9$ are taken together with the nitrogen to which they are attached to form a 5- or 6-membered monocyclic saturated or unsaturated ring, and in which the ring is optionally substituted or unsubstituted with oxo;
or $R^7$ and $R^9$ are taken together with the nitrogen to which they are attached to form a 5- or 6-membered monocyclic saturated or unsaturated ring, and in which the ring is optionally substituted or unsubstituted with oxo;
or a pharmaceutically acceptable salt or a crystal form thereof.

This invention further provides pharmaceutical compositions containing as an ingredient a therapeutically effective amount of a compound of Formula I or its pharmaceutically acceptable salt or a crystal form thereof, in admixture with one or more suitable carriers.

This invention further provides a method for treating pain conditions from a wide variety of causes, including but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, and post-traumatic injuries (including fractures and sports injuries); inflammation from a variety of causes, including but not limited to, bacterial, fungal or viral infections, rheumatoid arthritis, osteoarthritis, surgery, bladder infection or idiopathic bladder inflammation, over-use, old age, nutritional deficiencies, prostatis, conjunctivitis, pain associated with functional bowel disorders such as irritable bowel syndrome; and additionally for treating bladder disorders associated with bladder outlet obstruction, and urinary incontinence (including urge incontinence, stress incontinence, and bladder hyperreactivity); asthma; and septic shock in mammals comprising administering to a mammal in need of a therapeutically effective amount of a compound of Formula I or its pharmaceutically acceptable salt or a crystal form thereof.

DETAILED DESCRIPTION OF THE INVENTION

Definitions

Figure 1:
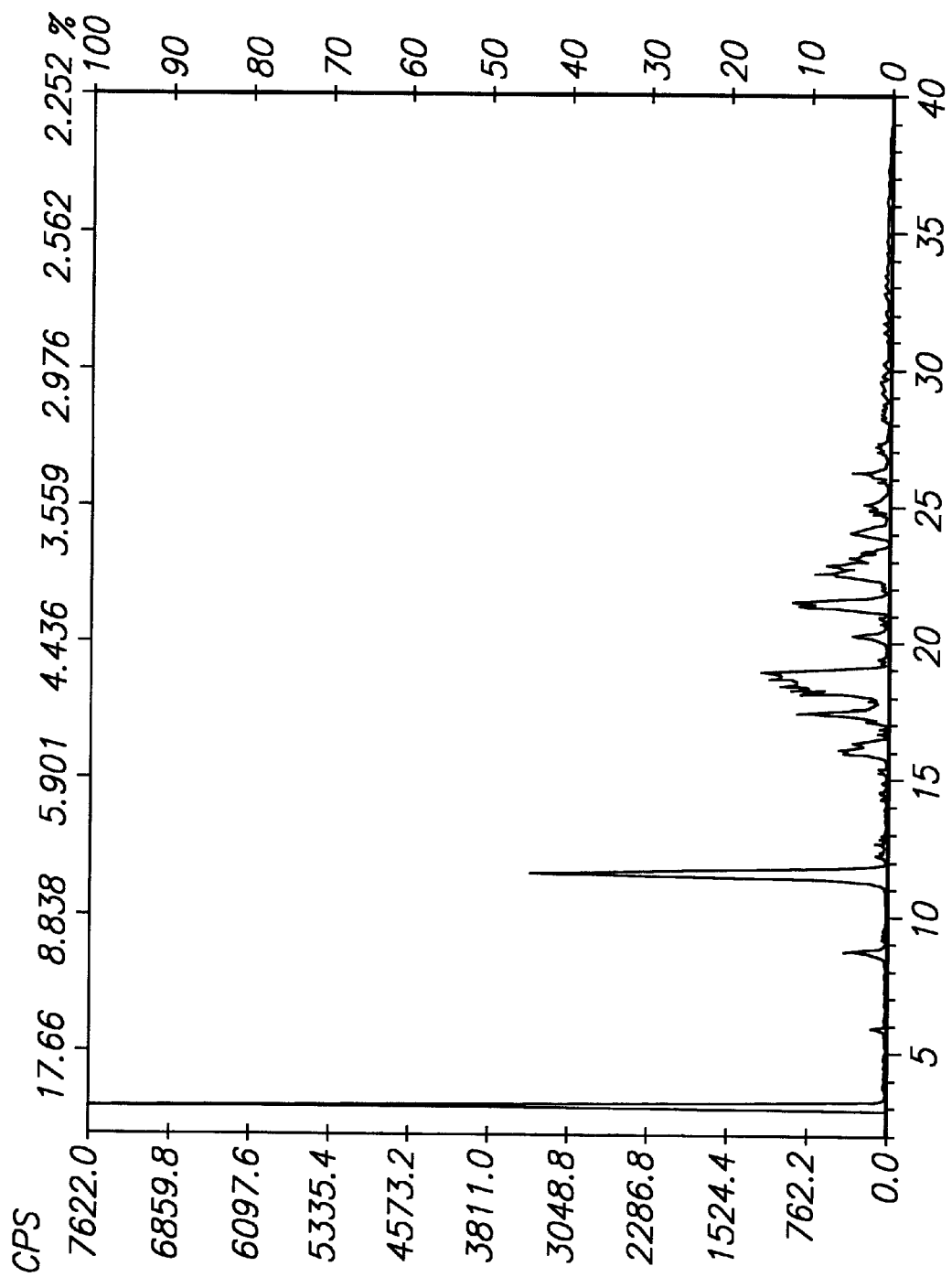
FIG. 1 shows the X-ray diffraction pattern of Crystal Form I of 2-[4-(4-isoproxybenzyl)phenyl]amino-imidazoline sulfate.

Unless otherwise stated, the following terms used in the specification and claims have the meanings given below:

"Alkyl" means a monovalent branched or unbranched saturated hydrocarbon radical having from one to eight carbon atoms inclusive, such as methyl, ethyl, propyl, isopropyl, isobutyl, sec-butyl, tert-butyl, pentyl, n-hexyl, and the like.

"Cycloalkyl" means a monovalent saturated carbocyclic radical having from three to fourteen carbon atoms inclusive, such as cyclopropylmethyl, cycylopropylethyl, cyclopropyl, cyclobutyl, 3-ethylcyclobutyl, cyclopentyl, cyclopentyl, cycloheptyl, and the like.

"Alkyloxy" means a radical —OR where R is alkyl as defined above, optionally substituted with one or more alkyloxy groups. Examples include, but are not limited to, methoxy, ethoxy, isopropoxy, sec-butoxy, isobutoxy, 2-ethoxy-1-(ethoxymethyl)ethoxy, and the like.

"Cycloalkyloxy" means a radical —OR where R is cycloalkyl as defined above, for example cyclopentyloxy, cyclohexyloxy, and the like.

"Hydroxyalkyl" means a linear monovalent hydrocarbon radical of one to four carbons or a branched monovalent hydrocarbon radical of three or four carbon atoms substituted with one or two hydroxy groups, provided that if two hydroxy groups are present, they are not both on the same carbon atom. Examples of hydroxyalkyl radicals include, but are not limited to hydroxymethyl, 1-hydroxymethyl-ethyl, 2-hydroxypropyl, 3-hydroxypropyl, 2-hydroxybutyl, 3-hydroxybutyl, 4-hydroxybutyl, 2,3-dihydroxypropyl, 1-(hydroxymethyl)-2- hydroxyethyl, 2,3-dihydroxybutyl, 3,4-dihydroxybutyl and 2-(hydroxymethyl)-3-hydroxypropyl, and the like, preferably 2-hydroxyethyl, and 1-(hydroxymethyl)- 2-hydroxyethyl.

"Alkyloxyalkyl" means hydroxyalkyl where the hydrogen atom(s) or one or the both hydroxy groups are replaced by $C_{1-4}$ alkyl, for example 2-methoxyethyl, 3-methoxy-butyl, 2-methoxymethyl, 2-isopropoxy-ethyl or 2-ethoxy-1-(ethoxymethyl)ethyl, and the like.

"Carboxyalkyl" means the radical —RCOOH where R is alkyl as defined above, for example 2-propionic acid; 3-butanoic acid, and the like.

"Aryl" means a monocyclic aromatic hydrocarbon radical of five or six ring atoms, or a 9 to 14-membered bicyclic or tricyclic ring system in which at least one ring is aromatic in nature. Examples of aryl radicals include, but are not limited to, benzyl, phenyl, naphthyl, and the like.

"Aryloxy" means a radical —OR where R is aryl as defined above, e.g., phenoxy, or the like.

"Arylalkyl" means the radical $R^aR^b$— where $R^a$ is aryl as defined above, and $R^b$ is alkyl as defined above, for example benzyl, phenethyl, 3-phenylpropyl, and the like.

"Heteroaryl" means a monocyclic aromatic ring or a 9 to 14-membered bicyclic ring system in which at least one ring is aromatic in nature, and includes heterocycles having one, two or three heteroatoms within the ring, chosen from nitrogen, oxygen, and sulfur. Examples of heteroaryl radicals include, but are not limited to, thienyl, imidazolyl, pyridinyl, pyrazinyl, and the like.

"Heterocylyl" means a monovalent saturated carbocyclic radical having a five, six or seven ring atoms of which one or two are selected from nitrogen, oxygen or sulfur. Examples of heterocyclyl radicals include, but are not limited to, tetrahydrofuranyl, tetrahydropyranyl, [1,3]dioxan-5-yl, 5-methyl-[1,3]dioxan-5-yl, morpholino, imidazolinyl, piperidinyl, pyrrolidinyl, pyrrolidin-2-one, pyrrolidin-2,3-dione, and the like; most preferably tetrahydropyranyl.

"Halogen" means fluoro, bromo, chloro and iodo, preferably fluoro and chloro.

"Haloalkyl" means alkyl substituted with one to three fluorine or chlorine atoms, for example chloromethyl, trifluoromethyl, 2,2,2-trifluoroethyl, 2,2,2-trichloroethyl, and the like.

"Amino-protecting group" means a protecting group that preserves a reactive amino group that otherwise would be modified by certain chemical reactions. Amino-protecting groups commonly used include those which are well-known in the art, for example benzyloxycarbonyl (carbobenzyloxy, CBZ), p-methoxybenzyloxycarbonyl, trialkylsilylcarboxyl, trifluoromethylcarbonyl, p-nitrobenzyloxycarbonyl, N-tert-butoxycarbonyl (BOC), and the like. Certain amino-protecting groups are more preferred over others because of the relative ease of removal.

"Optional" or "optionally" means that the subsequently described event or circumstance may but need not occur, and that the description includes instances where the event or circumstance occurs and instances in which it does not. For example, "optional bond" means that the bond may or may not be present and that the description includes both single and double bonds.

"Inert organic solvent" or "inert solvent" means a solvent inert under the conditions of the reaction being described in conjunction therewith, including for example, benzene, toluene, acetonitrile, tetrahydrofuran, N,N-dimethylformamide, chloroform ($CHCl_3$), methylene chloride or dichloromethane ($CH_2Cl_2$), dichloroethane, diethyl ether, ethyl acetate, acetone, methylethyl ketone, methanol, ethanol, propanol, isopropanol, tert-butanol, dioxane, pyridine, and the like. Unless specified to the contrary, the solvents used the reactions of the present invention are inert solvents.

A "pharmaceutically acceptable carrier" means a carrier that is useful in preparing a pharmaceutical composition that is generally compatible with the other ingredients of the composition, not deleterious to the recipient, and neither biologically nor otherwise undesirable, and includes a carrier that is acceptable for veterinary use as well as human pharmaceutical use. "A pharmaceutically acceptable carrier" as used in the specification and claims includes both one and more than one such carrier.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-napthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Crystal form" refers to various solid forms of the same compound, for example polymorphs, solvates, and amorphous forms.

(a) Polymorphs are crystal structures in which a compound can crystallize in different crystal packing arrangements, all of which have the same elemental composition. Different polymorphs usually have different X-ray diffraction patterns, infrared spectra, melting points, density, hardness, crystal shape, optical and electrical properties, stability, and solubility. Recrystallization solvent, rate of crystallization, storage temperature, and other actors may cause one crystal form to dominate.

(b) Solvates are generally a crystal form that contains either stoichiometric or non-stoichiometric amounts of a solvent. Often, during the process of crystallization some compounds have a tendency to trap a fixed molar ratio of solvent molecules in the crystalline solid state, thus forming a solvate. When the solvent is water, hydrates may be formed.

(c) Amorphous forms are noncrystalline materials with no long range order and generally do not give a distinctive powder X-ray diffraction pattern.

Crystal forms of the present invention have been obtained for 2-[4-(4-isoproxybenzyl)phenyl]amino-imidazoline sulfate, and are designated as Crystal Forms I and II. Crystal Forms I and II were obtained by utilizing the methods described in Examples 1 and 22, respectively, and are described in more detailing Examples 21–23. Crystal forms, in general, are further described in in Byrn et al., *Pharmaceutical Research*, 1995, vol 12(7), 945–954, and in *Remington: The Science and Practice of Pharmacy* 1995, edited by E. W. Martin, Mack Publishing Company, 19th edition, Easton, Pa., Vol. 2, Chapter 83, 1447–1462.

"Treating" or "treatment" of a disease includes:

(1) preventing the disease, i.e., causing the clinical symptoms of the disease not to develop in a mammal that may be exposed to or predisposed to the disease but does not yet experience or display symptoms of the disease, (2) inhibiting the disease, i.e., arresting the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease state being treated, the severity of the disease treated, the age and relative health of the subject, the route and form of administration, the judgement of the attending medical practitioner, and other factors.

As is well-known in the art, the imidazolin-2-ylamino group in compounds such as the compounds of Formula I is in tautomeric equilibrium with the imidazolin-2-ylideneamino group:

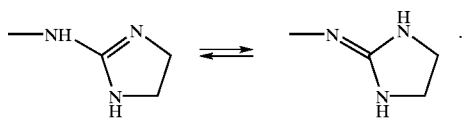

For convenience, all the compounds of Formula I are shown as having the imidazolin-2yl-amino structure, but it is to be understood that compounds of both tautomeric forms are intended to be within the scope of the invention.

Nomenclature

The naming and numbering of the compounds of this invention is illustrated below:

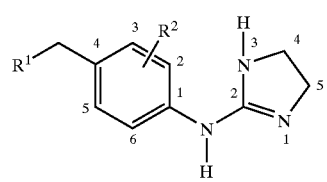

I

Side chains of the $R^1$ substituent are numbered as shown below:

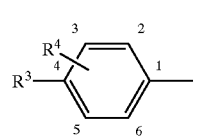

(A)

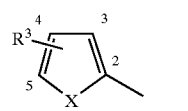

(B)

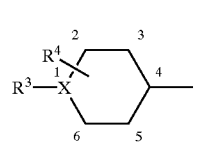

(C)

The compounds of the invention are named as imidazoline derivatives, and the nomenclature used in this application is generally based on the IUPAC recommendations. However, because a strict adherence to these recommendations would result in the names changing substantially when only a single substituent is changed, compounds have been named in a form that maintains consistency of nomenclature for the basic structure of the molecule.

For example, a compound of Formula I wherein $R^1$ is a group represented by formula (A), $R^2$ and $R^4$ are hydrogen, and $R^3$ is sec-butoxy, is named 2-[4-(4-sec-butoxybenzyl) phenyl]amino-imidazoline.

For example, a compound of Formula I wherein $R^1$ is a group represented by formula (B) in which X is S, $R^2$ and $R^4$ are hydrogen, and $R^5$ is methoxy, is named 2-[4-(5-methoxythienyl-2-ylmethyl)phenyl]amino-imidazoline.

For example, a compound of Formula I wherein $R^1$ is a group represented by formula (C) in which X is N, $R^2$ and $R^4$ are hydrogen, and $R^6$ is ethylaminocarbonyl, is named 2-[4-(1-ethylaminocarbonyl-piperidin-4-ylmethyl)phenyl] amino-imidazoline.

Preferred Compounds

Among the family of compounds of the present invention set forth in the Summary of the Invention, a preferred category includes the compounds of Formula I in which $R^2$ and $R^4$ are each independently in each occurrence hydrogen or halogen; preferably hydrogen, fluoro or chloro.

Within this category, one preferred subgroup includes the compounds of Formula I in which $R^1$ is a group represented by formula (A) wherein:

(1) $R^3$ is —$(CH_2)_m$OY wherein m is an integer from 0 to 3, and Y is preferably:
   (a) alkyl, preferably methyl, isopropyl, sec-butyl, isobutyl, or tert-butyl;
   (b) alkyloxyalkyl, preferably 2-ethoxy-1-(ethoxymethyl)ethyl;
   (c) cycloalkyl, preferably cyclopentyl or cyclohexyl; or
   (d) heterocyclyl, preferably tetrahydropyran-2-yl or tetrahydropyran-4-yl;
(2) $R^3$ is —$O(CH_2)_n$Z, wherein n is an integer from 1 to 4, and Z is preferably:
   (a) cycloalkyl, preferably cyclopentyl or cyclohexyl;
   (b) heterocyclyl, preferably tetrahydropyran-2-yl or tetrahydropyran-4-yl; or
   (c) hydroxyalkyl, preferably 1-hydroxymethyl;
(3) $R^3$ is —$(CH_2)_m SO_2 NR^8 R^9$ or —$(CH_2)_m CONR^8 R^9$, wherein m is an integer from 0 to 3 and
   (a) $R^8$ is hydrogen or alky, preferably hydrogen, methyl, ethyl, or isopropyl;
   (b) $R^9$ is
     (i) alkyl, preferably methyl, ethyl, propyl, isopropyl, sec-butyl, n-butyl, isobutyl, sec-butyl, or tert-butyl; or
     (ii) arylalkyl, preferably benzyl; or
(4) $R^3$ is —$(CH_2)_m NR^7 SO_2 R^9$ or —$(CH_2)_m NR^7 COR^9$, wherein m is an integer from 0 to 3 and
   (a) $R^7$ is hydrogen or alky, preferably hydrogen methyl, ethyl, or propyl;
   (b) $R^9$ is
     (i) alkyl, preferably methyl, ethyl, propyl, or isopropyl;
     (ii) aryl, preferably phenyl; or
     (iii) arylalkyl, preferably benzyl.

Within this category, another preferred subgroup includes the compounds of Formula I in which $R^1$ is a group represented by formula (B) wherein X is S: and
(1) $R^3$ is —$(CH_2)_m$OY, preferably wherein m is an integer from 0 or 1, and Y is:
   (a) alkyl, preferably methyl, isopropyl, isobutyl, sec-butyl or tert-butyl;
   (b) alkyloxyalkyl, preferably 2-ethoxy-1-(ethoxymethyl)ethyl;
   (c) cycloalkyl, preferably cyclopentyl or cyclohexyl; or
   (d) heterocyclyl, preferably tetrahydropyran-2-yl or tetrahydropyran-4-yl; or (2) $R^3$ is —$O(CH_2)_n$Z, wherein n is an integer from 1 to 4, and Z.

Within this category, another preferred subgroup includes the compounds of Formula I in which $R^1$ is a group represented by formula (C) wherein X is N.

Exemplary particularly preferred compounds are:

2-[4-(4-isoproxybenzyl)phenyl]amino-imidazoline;

2-{4-[4-(sec-butoxy)benzyl]phenyl}amino-imidazoline;

2-{4-[4-(cyclopentyloxy)benzyl]phenyl}amino-imidazoline;

2-{4-[4-(tetrahydropyran-4-yloxy)benzyl]phenyl}amino-imidazoline;

2-{4-[4-(tetrahydropyran-4-ylmethoxy)benzyl]phenyl}amino-imidazoline;

2-{4-[4-(tetrahydropyran-2-ylmethoxy)benzyl]phenyl}amino-imidazoline;

2-{4-[2-fluoro-4-(tetrahydropyran-4-ylmethoxy)benzyl]phenyl}amino-imidazoline;

2-{4-[4-(2-ethoxy-1-(ethoxymethyl)ethoxy)benzyl]phenyl}amino-imidazoline;

2-[4-(4-cyclopentyloxythienyl-2-ylmethyl)phenyl]amino-imidazoline;

2-{4-[4-(4-methoxyphenyl)sulfonylmethylaminoethoxybenzyl]phenyl}amino-imidazoline;

2-{4-[4-(1-hydroxymethyl-ethoxy)benzyl]phenyl}amino-imidazoline;

2-[4-(5-methoxythienyl-2-ylmethyl)phenyl]amino-imidazoline;

2-[4-(4-butylaminosulfonylbenzyl)phenyl]amino-imidazoline;

2-[4-(4-isoproxymethylbenzyl)phenyl]amino-imidazoline;

2-[4-(4-sec-butoxymethylbenzyl)phenyl]amino-imidazoline;

2-[4-(4-(isobutylaminosulfonyl)benzyl)phenyl]amino-imidazoline;

2-[4-(4-benzylaminocarbonylbenzyl)phenyl]amino-imidazoline;

2-[4-(4-isopropylaminosulfonylbenzyl)phenyl]amino-imidazoline;

2-[4-(4-isobutylaminocarbonylbenzyl)phenyl]amino-imidazoline; and

2-[4-(4-tert-butylaminosulfonylbenzyl)phenyl]amino-imidazoline.

GENERAL SYNTHETIC SCHEME

Compounds of this invention can be made by the methods depicted in the reaction schemes shown below.

The starting materials and reagents used in preparing these compounds are either available from commercial suppliers such as Aldrich Chemical Co., or are prepared by methods known to those skilled in the art following procedures set forth in references such as *Fieser and Fieser's Reagents for Organic Synthesis*, Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C., and most preferably at about room (or ambient) temperature, e.g., about 20° C.

In general, the compounds of Formula I are prepared by reacting intermediate phenylamine compounds of Ia to Il with an imidazoline compound 40 as an acid addition salt or a free base. Schemes A to G describe methods to prepare intermediate phenylamine compounds where $R^1$ is a group represented by formula (A); Schemes H to I describe methods to prepare intermediate phenylamine compounds where $R^1$ is a group represented by formula (B); and Schemes J to L describe methods to prepare intermediate phenylamine compounds where $R^1$ is a group represented by formula (C). Scheme M describes a method to prepare compounds of Formula I.

Scheme A

Scheme A describes a method of preparing compounds of Formula I wherein $R^1$ is a group represented by formula (A) and $R^3$ is ——O(CH$_2$)$_n$Z or ——(CH$_2$)$_m$OY, from the corresponding intermediate compound of formula Ia.

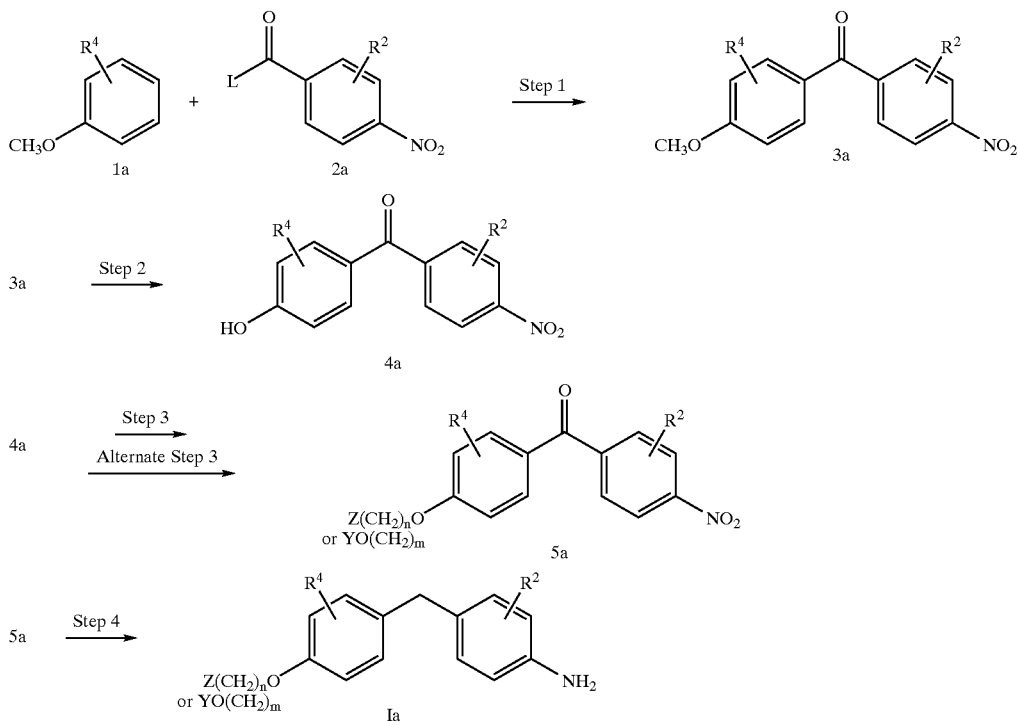

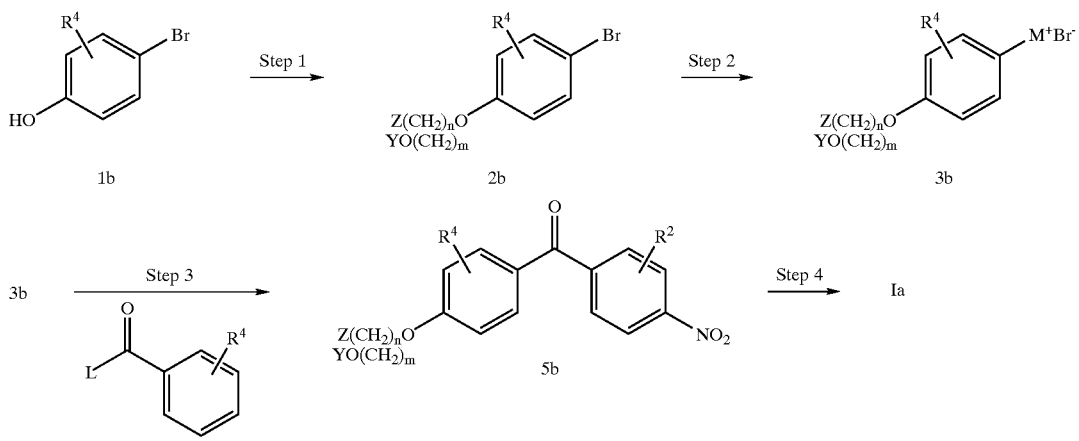

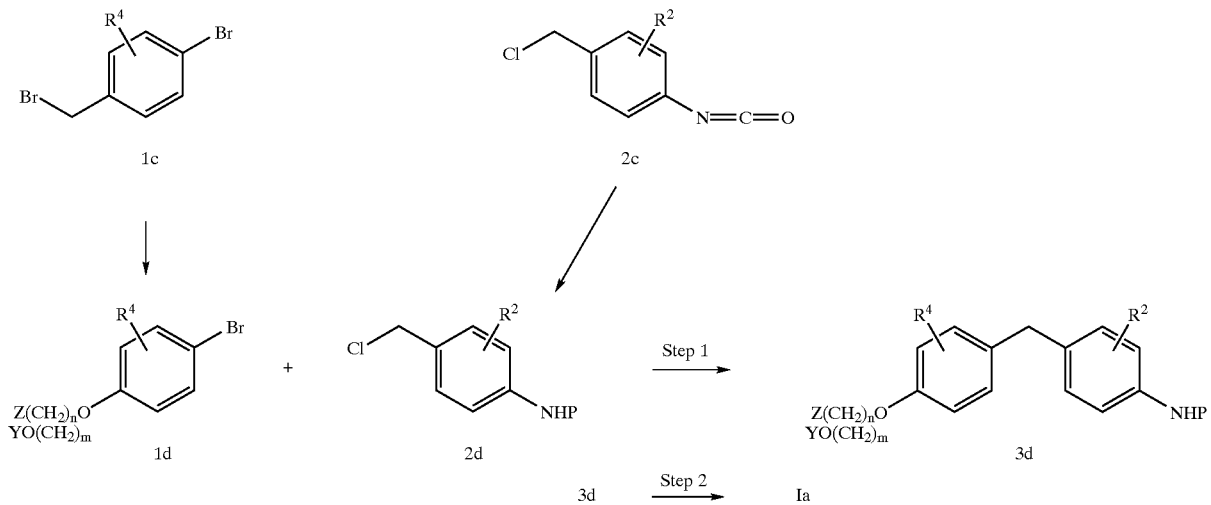

In general, the starting compounds of formula 1a, 1b, 1c, 2a, 2c, and 3a are commercially available, for example from Aldrich Chemical Company, or are known to or can readily be synthesized by those of ordinary skill in the art. For example, a methoxybenzoyl-nitrobenzene 3a can be prepared by the method described in Shani, Jashovam et al., *J. Med. Chem.*, 1985, 28, 1504.

Route (a) describes a preparation of a compound of formula Ia where $R^3$ is defined as above, in particular where m is an integer 0.

In step 1, a methoxybenzoyl-nitrobenzene 3a is prepared by acylating a methoxybenzene 1a with an acylating agent 2a where L is a leaving group such as chloro, under Friedel-Crafts acylating conditions. The reaction is carried out under an inert atmosphere in the presence of a Lewis acid such as aluminum chloride or boron trifluoride, and the like. Suitable inert organic solvents for the reaction include halogenated hydrocarbons, such as dichloromethane, dichloroethane, carbon disulfide, and the like, preferably carbon disulfide.

In step 2, a hydroxybenzoyl-nitrobenzene 4a is prepared by treating compound 3a with a strong acid such as a mixture of hydrobromic acid in glacial acetic acid. The demethylation reaction proceeds upon heating at a high temperature or at reflux temperature.

In step 3, a compound 5a is prepared by the direct alkylation of compound 4a with an alkylating agent such as an alkyl halide or with an acylating agent such as a halocarboxylic acid ester. The reaction proceeds under an inert atmosphere in the presence of an iodide catalyst such as sodium or potassium iodide, and a base such as potassium carbonate, sodium carbonate or cesium carbonate. Suitable solvents for the reaction include aprotic organic solvents, for example acetone, acetonitrile, N,N-dimethylformamide, N-methyl pyrrolidone, tetrahydrofuran, and the like, preferably tetrahydrofuran.

Alternatively, the compound 5a is prepared by reacting compound 4a with an organic phosphine such as triphenylphosphine in combination with a dialkyl azodicarboxylate such as diethyl azodicarboxyate under Mitsunobu reaction conditions. Suitable solvents for the reaction include inert organic solvents such as N,N-dimethylformamide, N-methyl pyrrolidone, ethyl acetate, tetrahydrofuran, and the like, preferably tetrahydrofuran.

In step 4, a phenylamine compound of formula Ia is prepared by the reducing the keto group and nitro group of compound 5a. Suitable keto and nitro group reducing conditions include nickel boride in acidic methanol or catalytic hydrogenation using a platinum or palladium catalyst (e.g., $PtO_2$ or Pd/C, preferably 10% Pd/C) in a protic organic solvent such as acidic methanol or acidic ethanol, preferably acidic ethanol.

Route (b) describes an alternative preparation of a compound of formula Ia where $R^3$ is as defined above, in particular where m is an integer 0.

In step 1, a substituted-bromobenzene 2b is prepared by treating a bromophenol 1b with an alkylating agent such as an alkyl halide. The reaction proceeds in the presence of a base such as potassium carbonate, sodium carbonate or cesium carbonate, and a catalyst such as sodium iodide. Suitable solvents for the reaction include aprotic solvents such as N,N-dimethylformamide, tetrahydrofuran, acetonitrile, and the like.

In step 2, a organometallic compound 3b where $M^+Br^-$ is an organometallic reagent, can be readily synthesized by those of ordinary skill in the art, for example by treating compound 2b with a suitable metal under Grignard reaction conditions. The reaction proceeds under an inert atmosphere in an aprotic organic solvent such as tetrahydrofuran.

In step 3, a benzoyl-nitrobenzene 5b is prepared by reacting compound 3b with an acylating agent such as an acyl halide where L is a leaving group such as chloro, in the presence of a catalyst such as tetrakis(triphenylphosphine) palladium. The reaction proceeds under an inert atmosphere in an aprotic organic solvent such as tetrahydrofuran.

A phenylamine compound of formula Ia is subsequently prepared by utilizing the methods described above in Scheme A, route (a), step 4.

Route (c) describes an alternative preparation of a compound of formula Ia where $R^3$ is as defined above, in particular where m is an integer 1.

A benzyl bromide 1d is prepared by reacting a bromobenzyl bromide 1c with a desired alcohol in the presence of a strong base such as sodium hydride. The reaction proceeds under an inert atmosphere in an aprotic solvent such as N,N-dimethylformamide, tetrahydrofuran, acetonitrile, and the like.

An amino-protected chlorobenzyl-phenylamine 2d where P is an amino-protecting group, is prepared by reacting a chlorobenzyl isocyanate 2c with an amino-protecting reagent such as a trialkylsilyethyl alcohol. The reaction proceeds under an inert atmosphere in an aprotic solvent such as N,N-dimethylformamide, tetrahydrofuran, acetonitrile, and the like.

In step 1, an amino-protected benzylphenyl 3d is prepared by coupling compound 1d and compound 2d under Stille reaction conditions. For example, the reaction proceeds in the presence of lithiated compounds such as tert-butyllithium; tin compounds such as tributyltin halide; and a catalyst such as tetrakis(triphenylphosphine)palladium. The reaction proceeds under an inert atmosphere in an aprotic solvent such as hexamethylphosphoramide, N,N-dimethylformamide, tetrahydrofuran, acetonitrile, dimethyl sulfoxide, and the like.

In step 2, a phenylamine compound of formula Ia is prepared by removing the amino-protecting group from compound 3d by treatment with a specific cleaving reagent, for example tetra-n-butylammonium fluoride. The reaction proceeds under an inert atmosphere in an aprotic solvent such as N,N-dimethylformamide, tetrahydrofuran, acetonitrile, dimethyl sulfoxide, and the like.

Exemplary preparations of compounds of Formula I by this method from the corresponding compounds of formula Ia are described in detail in Examples 1–4. Exemplary preparations of compounds of formula 1d and 2d are described in detail in Preparations 1 and 2, respectively.

Scheme B

Scheme B describes an alternative method of preparing compounds of Formula I where $R^1$ is a group represented by formula (A) and $R^3$ is alkyl, cycloalkyl, halo, heterocyclyl, or —$NR^8R^9$, from the corresponding intermediate compound of formula Ib.

Route (a)

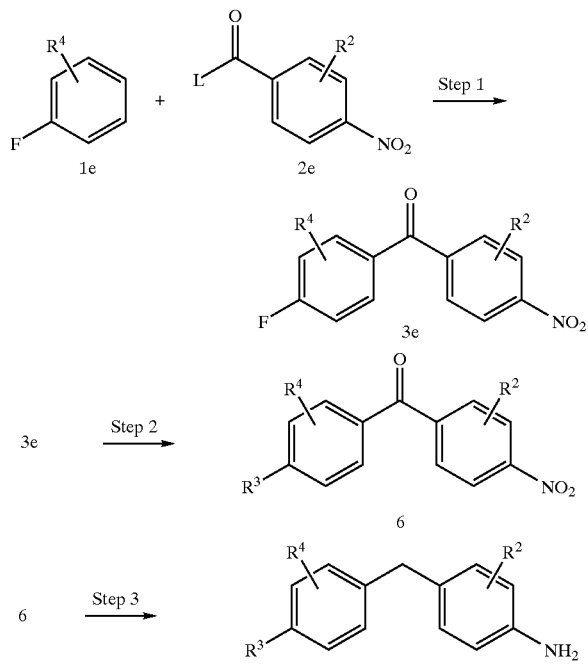

Route (b)

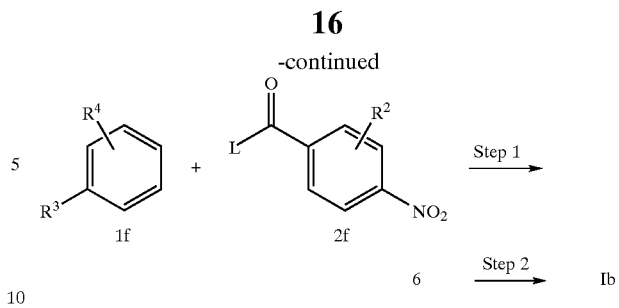

In general, the starting compounds 1e, 2e, if, and 2f are commercially available, for example from Aldrich Chemical Company, or are known to or can readily be synthesized by those of ordinary skill in the art.

Route (a) describes a preparation of a compound of formula Ib where $R^3$ is as defined above starting from a fluorobenzene 1e.

In step 1, a fluorobenzoyl-nitrobenzene 3e is prepared by acylating a fluorobenzene 1 e with an acylating agent 2e where L is a leaving group such as chloro. Suitable solvents or the reaction include halogenated hydrocarbons, such as dichloromethane, dichlorcethane, carbon disulfide, and the like, preferably carbon disulfide.

In step 2, an $R^3$-substituted-benzoyl-nitrobenzene 6 is prepared by he displacement of the fluoro group of the compound of formula 3e by a primary or secondary amine, such as dimethylamine, morpholine, and the like. The reaction is carried out in the presence of a base, e.g., potassium carbonate, sodium carbonate, cesium carbonate, and the like, in an aprotic organic solvent such as tetrahydrofuran, N,N-dimethylformamide, dimethyl sulfoxide, and the like, preferably dimethyl sulfoxide.

In step 3, a phenylamine compound of formula Ib is prepared by the reduction of the keto group and nitro group of the compound of formula 6, utilizing the reaction conditions described in Scheme A, route (a), step 4.

Route (b) describes an alternative preparation of a compound of formula Ib, in particular where $R^3$ is alkyl or cycloalkyl.

In step 1, an alkylbenzoyl-nitrobenzene 6 is prepared by reacting alkylbenzene if with an acylating agent 2f where L is a leaving group such as chloro, under Friedel-Crafts acylating conditions. The reaction is carried out in the presence of a Lewis acid such as aluminum chloride or boron trifluoride, and the like. Suitable solvents for the reaction include halogenated hydrocarbons such as dichloromethane, dichloroethane, carbon disulfide, and the like, preferably carbon disulfide.

In step 2, a phenylamine compound of formula Ib is prepared by the reduction of the keto group and nitro group of the compound of formula 6, utilizing the reaction conditions described in Scheme A, route (a), step 4.

An exemplary preparation of a compound of Formula I by this method from the corresponding compound of formula Ib is described in detail in Example 5.

Scheme C

Scheme C describes an alternative method of preparing compounds of Formula I where $R^1$ is a group represented by formula (A) and $R^3$ is ——$(CH_2)_m NR^7 SO_2 R^9$, from the corresponding intermediate compounds of formula Ic.

Route (a)

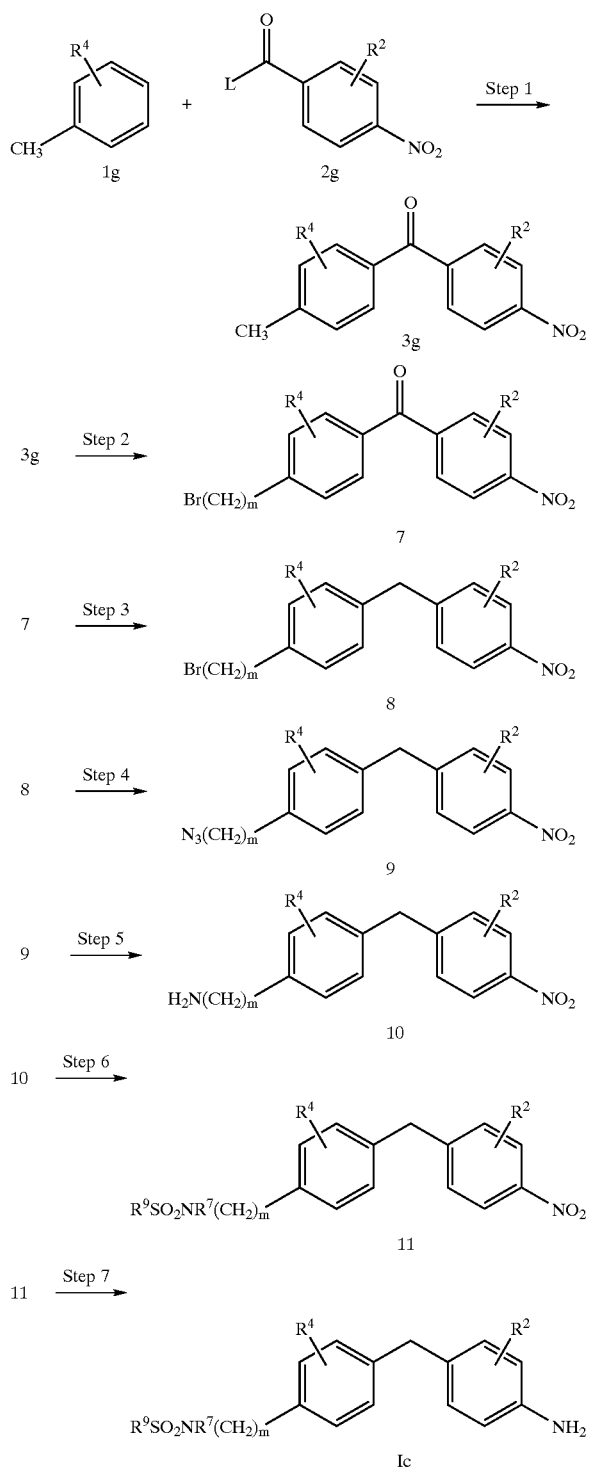

Route (b)

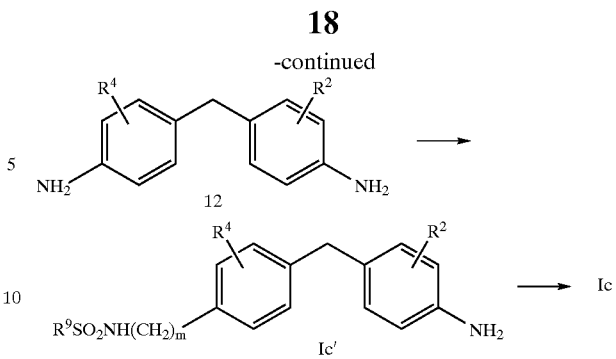

Route (a) describes the preparation of a compound of formula Ic where $R^3$ is a sulfonamide group, in particular where m is an integer 1:

In step 1, a methylbenzoyl-nitrobenzene 3g is prepared by acylating a methylbenzene 1g with an acylating agent 2g where L is a leaving group such as chloro, under Friedel-Crafts acylating conditions. The reaction is carried out under an inert atmosphere in the presence of a Lewis acid such as aluminum chloride or boron trifluoride, and the like. Suitable inert organic solvents for the reaction include halogenated hydrocarbons, such as dichloromethane, dichloroethane, carbon disulfide, and the like, preferably carbon disulfide.

In step 2, a bromobenzoyl-nitrobenzene 7 is prepared by benzylic bromination of compound of formula 3g with a suitable brominating agent such as N-bromosuccinimide. The bromination proceeds upon heating in the presence of a free radical initiator such as benzoyl peroxide under an inert atmosphere (e.g., argon or nitrogen, preferably argon). Suitable nonpolar solvents for the reaction are chlorinated or aromatic hydrocarbons such as carbon tetrachloride or benzene.

In step3, a bromobenzyl-nitrobenene 8 is prepared by reduction of the keto group in compound of formula 7 by treatment with a reducing agent selective for the keto group, such as triethylsilane. The reaction proceeds under an inert atmosphere in the presence of a strong acid such as trifluoromethanesulfonic acid. Suitable solvents for the reaction include halogenated hydrocarbons such as dichloromethane or dichloroethane.

In step 4, an azidobenzyl-nitrobenzene 9 is prepared by the displacement of the benzylic bromide of compound 8 with a nucleophilic azide anion. Suitable solvents for the reaction are aprotic organic solvents such as N,N-dimethylformamide, N-methylpyrrolidone, tetrahydrofuran, and the like.

In step 5, an aminobenzyl-nitrobenzene 10 is prepared by the reduction of the azide to a primary amine by reacting compound 9 with a suitable azide reducing agent such as triphenylphosphine and water. Suitable solvents for the reaction are organic solvents such as diethyl ether, 1,4-dioxane, tetrahydrofuran, and the like, preferably tetrahydrofuran.

In step 6, a sulfonylaminobenzyl-nitrobenzene 11 is prepared by reacting compound 10 with a sulfonylating agent $R^9 SO_2 L$ where L is a leaving group, particularly chloro, in the presence of a base, e.g., triethylamine. Sulfonyl halides are commercial available or may be prepared by methods such as those described in (1) Langer, R. F., *Can. J. Chem.*, 1983, 61, 1583–1592; Aveta, R. et al., *Gazetta Chimica Italiana*, 1986, 116, 649–652; or King, J. F. and Hillhouse, J. H., *Can J. Chem.*, 1976, 54, 498. Suitable solvents for the reaction are halogenated hydrocarbons such as dichloromethane, or a two-phase system utilizing water and ethyl acetate (e.g., Schotten-Baumann reaction procedure).

In step 7, a phenylamine compound of formula Ic is prepared by reducing the nitro group of compound 11 to an amino group. Suitable nitro reducing agents include nickel boride in acidic methanol or catalytic hydrogenation using a platinum or palladium catalyst (e.g., $PtO_2$ or Pd/C) in an organic solvent such as ethanol or ethyl acetate.

Alternatively, route (b) describes the preparation of a compound of formula Ic where $R^3$ is a sulfonamide group, in particular where m is an integer 0:

A compound of formula Ic' is prepared by reacting a 4,4'-methylenedianiline 12 with a sulfonylating agent such as a sulfonyl halide, and utilizing the reaction conditions described above in step 6, and performing an acid-base extraction with a hydroxide and a mineral acid.

Optionally, a compound of formula Ic can be prepared by further alkylating the compound of formula Ic' with a suitable alkylating agent in the presence of a strong base such as potassium tert-butoxide. Suitable solvents include aprotic organic solvents such as acetonitrile; N,N-dimethylformamide, dimethyl sulfoxide, and the like, preferably dimethyl sulfoxide.

Exemplary preparations of compounds of Formula I by this method from the corresponding compounds of formulae Ic' and Ic are described in detail in Examples 6–9.

Scheme D

Scheme D describes an alternative method of preparing compounds of Formula I where $R^1$ is a group represented by formula (A) and $R^3$ is ——$(CH_2)_mNR^7COR^9$, from the corresponding intermediate compounds of formula Id.

Route (a)

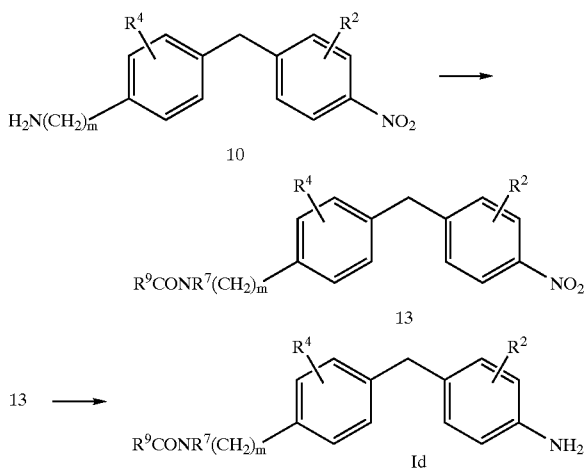

Route (b)

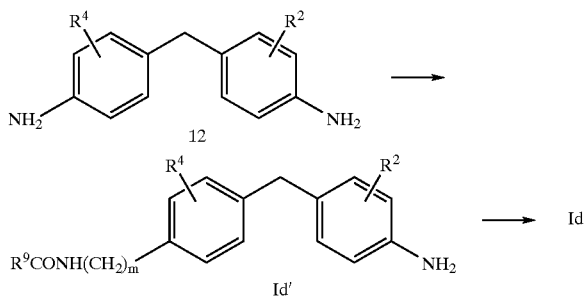

Route (a) describes the preparation of a compound of formula Id where $R^3$ is a carboxamide group, in particular where m is an integer 1:

In general, a compound of formula Id is prepared by utilizing the reaction conditions previously described in Scheme C, route (a), but in step 6, the aminobenzylnitrobenzene 10 is reacted with a acylating agent $R^9COL$ where L is a leaving group such as chloro, to give a carboxamide 13. A phenylamine compound of Formula Id is then prepared by proceeding correspondingly as in step 7.

Alternatively, route (b) describes the preparation of a compound of Formula Id where $R^3$ is a sulfonamide group, in particular where m is an integer 0:

In general, a compound of formula Id' is prepared by utilizing the reaction conditions previously described in Scheme C, route (b), but the 4,4'-methylenedianiline 12 is reacted with an acylating agent such as a acyl halide to give a compound of formula Id'. Then optionally, a compound of formula Id can be prepared by further alkylating the compound of formula Id' with a suitable alkylating agent in the presence of a strong base such as potassium tert-butoxide. Suitable solvents include aprotic organic solvents such as tetrahydrofuran, N,N-dimethylformamide, dimethyl sulfoxide, and the like, preferably dimethyl sulfoxide.

An exemplary preparation of a compound of Formula I by this method from the corresponding compound of formula Id is described in Example 7.

Scheme E

Scheme E describes an alternative method of preparing compounds of Formula I where $R^1$ is a group represented by formula (A) and $R^3$ is ——$(CH_2)_mNR^7C(V)NR^8R^9$ where V is S or O, from the corresponding intermediate compounds of formula Ie.

Route (a)

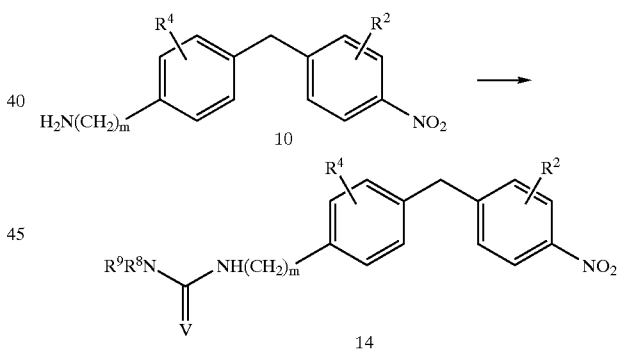

Route (b)

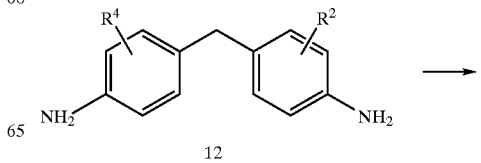

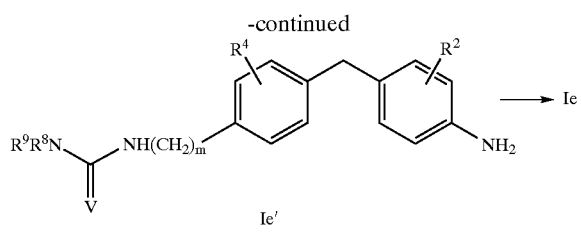

Route (c)

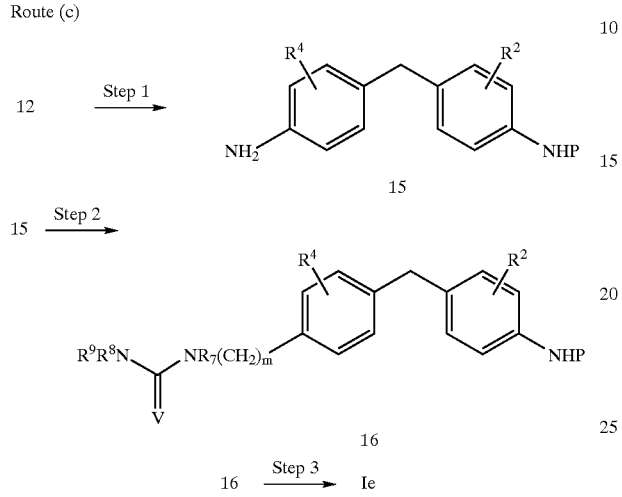

Route (a) describes the preparation of a compound of formula Ie where $R^3$ is an urea/thiourea group, in particular where m is an integer 1:

In general, a compound of formula Ie is prepared by utilizing the reaction conditions previously described in Scheme C, route (a), but in step 6, reacting the aminobenzylnitrobenzene 10 with an isocyanate/isothiocyanate in an aprotic organic solvent, to give an urea/thiourea compound 14. A phenylamine compound of formula Ie is then prepared by proceeding correspondingly as in step 7.

Alternatively, route (b) describes the preparation of a compound of Formula Ie where $R^3$ is a an urea/thiourea group, in particular where m is an integer 0:

In general, a compound of formula Ie' is prepared by utilizing the reaction conditions previously described in Scheme C, route (b), but reacting a 4,4'-methylenedianiline 12 with an isocyanate/thioisocyanate in an aprotic organic solvent such as dichloromethane, tetrahydrofuran, N,N-dimethylformamide, and the like. Then optionally, a compound of formula Ie can be prepared by further alkylating the compound of formula Ie' with a suitable alkylating agent in the presence of a strong base such as potassium tert-butoxide. Suitable solvents include aprotic organic solvents such as tetrahydrofuran, dimethyl sulfoxide, N,N-dimethylformamide, and the like, preferably dimethyl sulfoxide.

Alternatively, route (c) describes the preparation of a compound of Formula I where $R^3$ is an urea/thiourea group, in particular where m is an integer 0:

In step 1, a compound 15 where P is an amino-protecting group, is prepared by attaching a suitable amino-protecting group such as benzyl, tert-butoxycarbonyl (BOC) or carbobenzyloxy (CBZ) to compound 12 by methods known to one of ordinary skill in the art, for example under under Schotten-Baumann conditions.

In step 2, an urea/thiourea compound 16 is prepared by reacting a compound 15 with an isocyanate/isothiourea in a organic solvent including dichloromethane, dicloroethane, or tetrahydrofuran.

In step 3, a compound of formula Ie is prepared by removing the amino-protecting group from compound 16 under hydrogenation conditions using a catalyst such as palladium or platinum catalysts. Suitable solvents for the reaction include protic or aprotic organic solvents such as methanol, ethanol, ethyl acetate, and the like.

An exemplary preparation of a compound of Formula I by this method from the corresponding compound of formula Ie is described in detail in Example 10.

Scheme F

Scheme F describes an alternative method of preparing compounds of Formula I where $R^1$ is a group represented by formula (A), and $R^3$ is ——$(CH_2)_mSO_2NR^8R^9$ from the corresponding intermediate compounds of formula If.

Route (a)

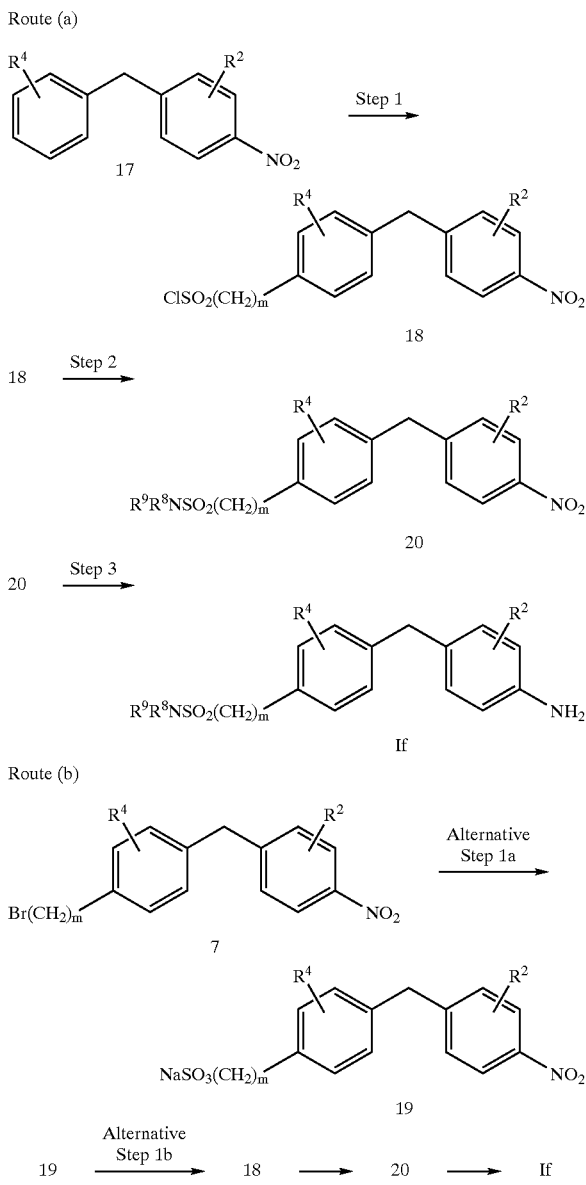

Route (a) describes the preparation of a compound of Formula If where $R^3$ is a sulfonamide group, in particular where m is an integer 0:

In step 1, a chlorosulfonylbenzyl-nitrobenzene 18 is prepared by reacting a benzyl-nitrobenzene 17 with a chlorosulfonating agent such chlorosulfonic acid. The reaction proceeds at a temperature of about −50° to 10° C. in a inert organic solvent such as dichloromethane or dichloroethane.

In step 2, an aminosulfonylbenzyl-nitrobenzene 20 is prepared by reacting compound 18 with a primary or secondary amine. Suitable solvents for the reaction include inert organic solvents such as dichloromethane, dichloroethane or tetrahydrofuran.

In step 3, a phenylamine compound of formula It is prepared by reducing the nitro group of compound 37 to an amino group. Suitable nitro group reducing conditions include catalytic hydrogenation using a platinum or palladium catalyst in a protic organic solvent, such as methanol, ethanol, or ethyl acetate.

Route (b) describes an alternative preparation of a compound of Formula If where $R^3$ is a sulfonamide group, in particular where m is an integer 1:

The bromobenzyl-nitrobenzene 7 is prepared as previously described in Scheme C.

In alternative step 1a, a compound 19 is prepared by reacting compound 7 with a sulfurous acid salt such as aqueous sodium sulfite or potassium sulfite. The reaction proceeds at reflux temperature in water or an acetonitrile-water mixture.

In alternative step 1b, the compound 18 is then prepared by treating compound 19 with a chlorinating agent such as phosphorus pentachloride. The reaction can be performed neat or in the presence of phosphorus oxychloride.

The phenylamine compound of formula If is then prepared by proceeding correspondingly as in Scheme F, route (a), steps 2 and 3.

Exemplary preparation of compounds of Formula I by this method from the corresponding compounds of formula If are described in detail in Examples 11–12.

Scheme G

Scheme G describes an alternative method of preparing compounds of Formula I where $R^1$ is a group represented by formula (A) and $R^3$ is ——$(CH_2)_mCONR^8R^9$, from the corresponding intermediate compounds of formula Ig.

Route (a)

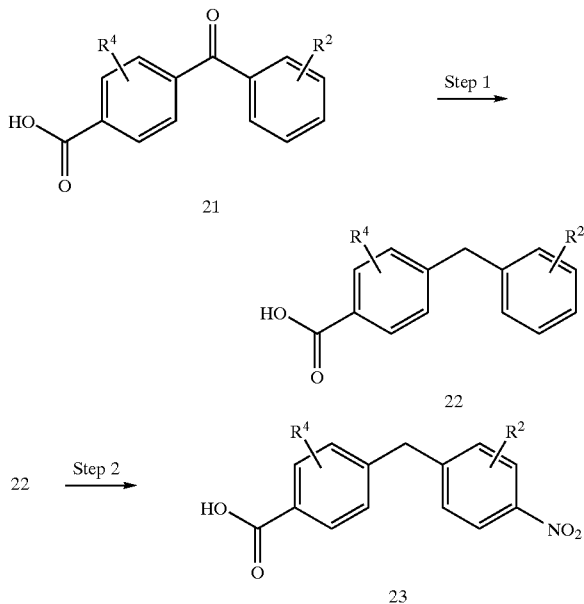

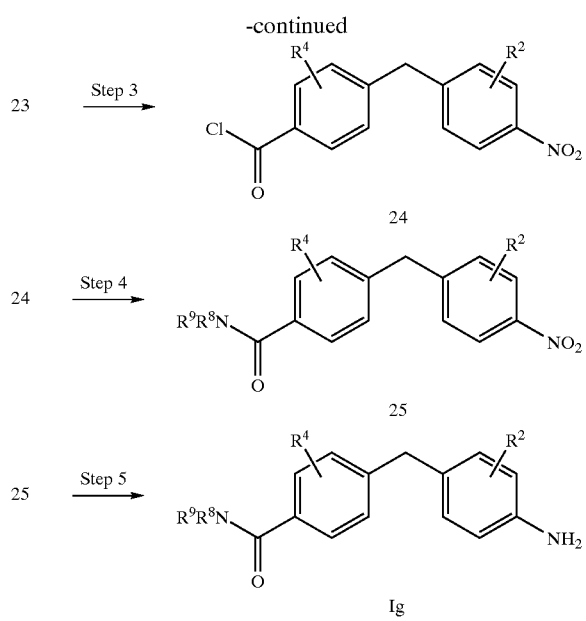

In step 1, a benzyl-benzoic acid 22 is prepared by reducing the ketone group of benzoyl-benzoic acid 21 with a reducing agent selective for the ketone group, such as hydrogenation conditions using a palladium or platinum catalyst. The reaction proceeds at ambient temperature in the presence of a strong acid such as perchloric acid. Suitable solvents for the reaction are protic or aprotic solvents such as methanol, ethanol, ethyl acetate, and the like.

In step 2, a nitrobenzyl-benzoic acid 23 is prepared by following the method described in the chemical literaturen, for example Coon et al., *J. Org. Chem.* 1973, 38, 4243. Briefly, compound 22 is nitrated by the formation of nitronium salts such as by reaction with trifluoromethanesulfonic acid and nitric acid. Suitable solvents for the reaction include inert organic solvents such as halogenated hydrocarbons, for example dichloromethane or dichloroethane.

In step 3, nitrobenzyl-benzoyl chloride 24 is prepared by treating compound 23 with a chlorinating agent such as phosgene or phosgene equivalents, phosphorus oxychloride or oxalyl chloride in the presence of N,N-dimethylformamide (Vilsmeier reaction conditions). Suitable solvents for the reaction include inert organic 3solvents such as halogenated hydrocarbons, for example dichloromethane or dichlorcethane.

In step 4, an aminocarbonylbenzyl-nitrobenzene 25 is prepared by reacting compound 24 with a primary or secondary amine. The reaction proceeds in the presence of a base such as pyridine in an inert organic solvent such as dichloromethane, dichloroethane or tetrahydrofuran.

In step 5, a phenylamine compound of formula Ig is prepared by reducing the nitro group of compound 25 to an amino group. Suitable nitro group reducing conditions include hydrogenation with a platinum or palladium catalyst in an alcoholic solvent such as methanol or ethanol.

An exemplary preparation of a compound of Formula I by this method from the corresponding compound of formula Ig is described in detail in Example 13.

Scheme H

Scheme H describes an alternative method of preparing compounds of Formula I where $R^1$ is a group represented by formula (B) where X is S; and $R^5$ is or ——$O(CH_2)_nZ$ or ——$(CH_2)_mOY$, in particular where m is an integer 0, from the corresponding intermediate compounds of formula Ih.

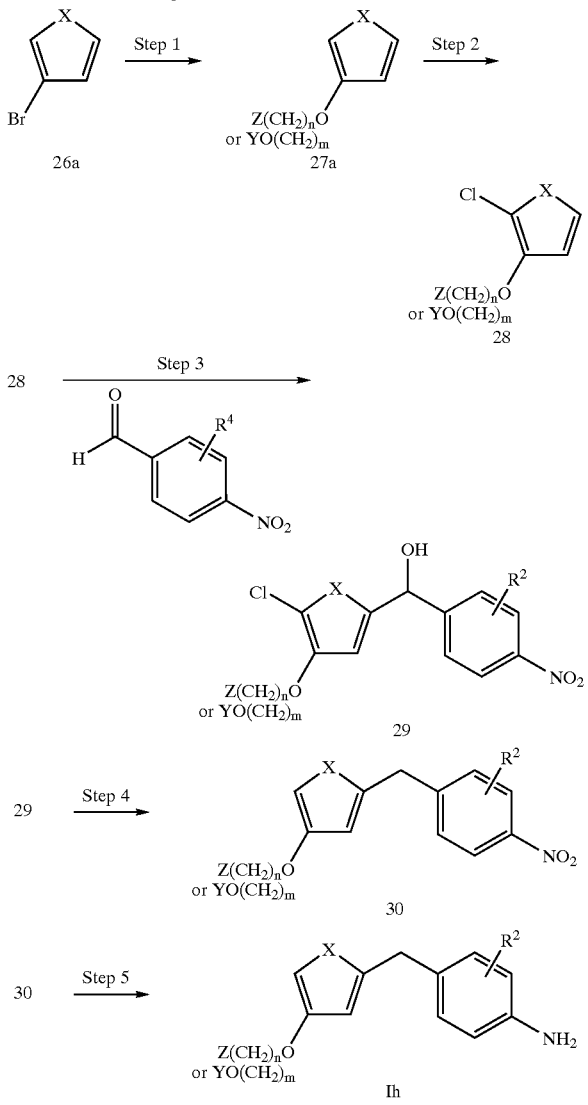

In step 1, a thienyl compound 27b is prepared by treating the bromothienyl 26a with an alkoxide anion, for example sodium methoxide, in the presence of copper salts such as cuprous iodide. The reaction proceeds under an inert atmosphere in a suitable aprotic organic solvent such as N,N-dimethylformamide, N-methylpyrrolidine, tetrahydrofuran, and the like.

In step 2, an ortho-chlorinated thienyl compound 28 can be prepared by methods in the chemical literature, for example, Stanetty et al., *Monatshefte Chemie* 1989, 120, 65. Briefly, the compound 27b is treated with a halogenating agent such as sulfuryl chloride under an inert atmosphere. Suitable solvents for the reaction include hexane, dichloromethane or dichloroethane.

In step 3, a thienylhydroxymethyl-nitrobenzene 29 is prepared by treating compound 28 with a strong base such as n-butyllithium, followed by a benzaldehyde. The reaction proceeds with cooling under an inert atmosphere. Suitable solvents for the reaction include aprotic organic solvents such as tetrahydrofuran, or diethyl ether, and the like, preferably tetrahydrofuran.

In step 4, a thienylmethyl-nitrobenzene compound 30 is prepared by reducing the hydroxymethyl group of the compound 29 with an alkylated halosilane such as trimethylsilyl chloride, in the presence of an halide salt, e.g., sodium iodide. Suitable solvents for the reaction include aprotic solvents for example acetonitrile, N,N-dimethylformamide, and the like.

In step 5, a phenylamine compound of formula Ih is prepared by reducing the nitro group of compound 30 to an amino group. Suitable nitro group reducing conditions include nickel boride in acidic methanol, tin(II) chloride hydrate in ethanol, or catalytic hydrogenation using a platinum or palladium catalyst (e.g., $PtO_2$ or Pd/C) in an organic solvent such as ethanol, isopropanol, or ethyl acetate.

An exemplary preparation of a compound of Formula I by this method from the corresponding compound of formula Ih is described in detail in Example 14.

Scheme I

Scheme I describes an alternative method of preparing compounds of Formula I where $R^1$ is a group represented by formula (B) where X is S, and $R^5$ is or ——$O(CH_2)_nZ$ or ——$(CH_2)_mOY$, in particular where m is an integer 0, from the corresponding intermediate compound if formula Ii.

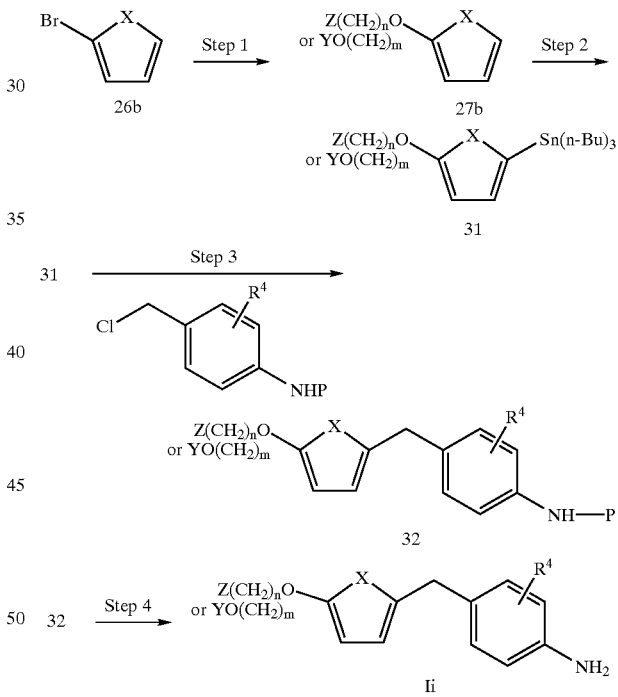

In step 1, a thienyl compound 27b can be prepared by a method described in the chemical literature, for example M. A. Keeystra et al., *Tetrahedron*, 1992, 48, 3633. Briefly, the bromothienyl compound 26b is treated with an alkoxide anion, e.g., methoxide or cyclopentoxide, in the presence of a strong base such as sodium hydride. The reaction proceeds with heating under an inert atmosphere, followed by the addition of copper salts such as cuprous bromide or cuprous iodide. Suitable solvents for the reaction include inert organic solvents such as methanol, ethanol, dioxane or tetrahydrofuran.

In step 2, an alkylstannane 31 is prepared by the stannylation of the compound of formula 27b by treatment with a haloalkylstannane, such as (tri-n-butyl)tin chloride, in the presence of a lithium reagent, e.g., n-butyllithium. The reaction proceeds under an inert atmosphere in an aprotic organic solvent including tetrahydrofuran or diethyl ether.

In step 3, a P-protected compound 32 where P is an amino-protecting group, is prepared by reacting compound 31 with an amino-protected benzyl chloride reagent, particularly a trimethylsilylalkyl carbonyl group. The reaction proceeds in the presence of a suitable catalyst including platinum or palladium catalyst, e.g., tetrakis (triphenylphosphine)-palladium in a co-solvent such as hexamethylphosphoramide.

In step 4, a phenylamine compound of formula Ii is prepared by removing the amino-protecting group from compound 32 by treatment with a nucleophile such as a fluoride ion source, e.g., (tetra-n-butyl)ammonium fluoride, in an inert organic solvent including dioxane, tetrahydrofuran or diethyl ether, and the like.

Alternatively, other phenylamine compounds of formula Ii can be prepared by exchanging the —O(CH$_2$)$_n$Z or —(CH$_2$)$_m$OY of formula Ii where Y or Z is alkyl or cycloalkyl, with other alkyl groups in the presence of an acid such as p-toluenesulfonic acid. The reaction proceeds under an inert Atmosphere at reflux temperature. Suitable solvents for the reaction include alcoholic solvents such as methanol, ethanol or isopropanol.

Exemplary preparations of compounds of Formula I by this method from th corresponding compounds of formula Ii is described in detail in Examples 15–17.

Scheme J

Scheme J describes an alternative method of preparing compounds of Formula I where R$^1$ is a group represented by formula (C) where X is N, and R$^6$ is ——C(V)NR$^8$R$^9$ where V is O or S, from the corresponding intermediate compound of formula Ij.

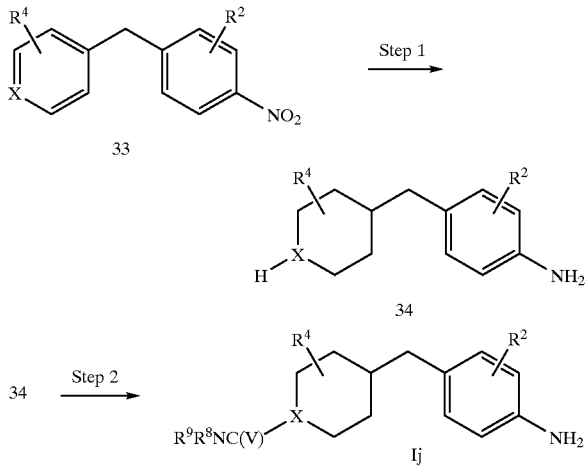

In step 1, a heterocyclylmethyl-phenylamine 34 is prepared by reducing the aromatic and nitro groups of a heteroarylmethyl-nitrobenzene 33 by catalytic hydrogenation conditions, for example, a platinum or palladium catalyst (e.g., PtO$_2$ or Pd/C, preferably 10% Pd/C) in a protic organic solvent such as acidic methanol or acidic ethanol, preferably acidic ethanol. The reaction proceeds at a temperature of about 200 to 100° C. at about 20–100 psi pressure.

In step 2, a phenylamine compound of formula Ij is prepared by reacting compound 34 with an isocyanate/thioisocyanate in an inert organic solvent such as dichloromethane, diethylamine, or tetrahydrofuran. The reaction proceeds under an inert atmosphere at about −100 to 30° C.

An exemplary preparation of a compound of Formula I by this method from the corresponding compound of formula Ij is described in detail in Example 18.

Scheme K

Scheme K describes an alternative method of preparing compounds of Formula I where R$^1$ is a group represented by formula (C) where X is N, and R$^6$ is ——COR$^9$ or ——SO$_2$R$^9$, from the corresponding intermediate compound of formula Ik.

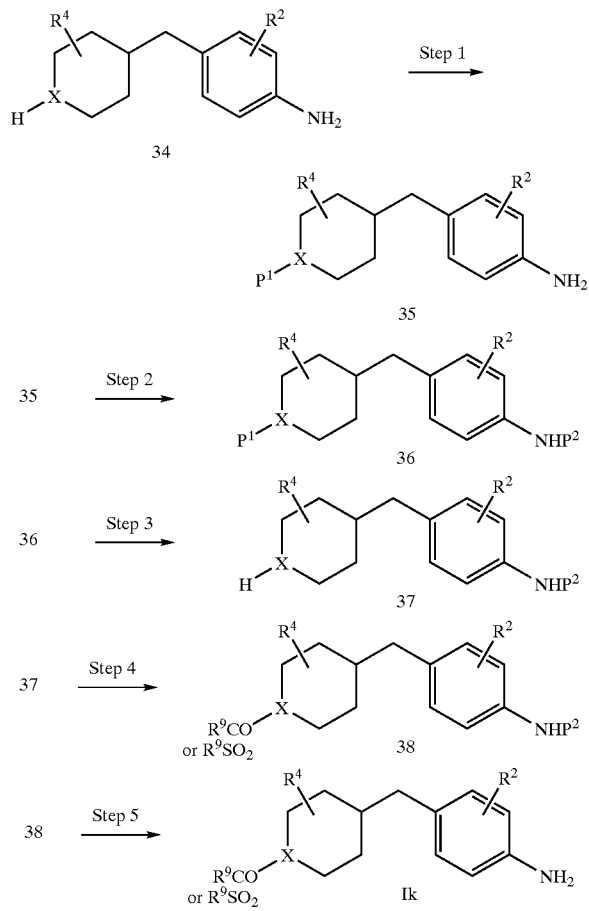

The heterocycylylmethyl-phenylamine 34 is prepared as previously described in Scheme J.

In step 1, a P$^1$-protected compound 35 where P$^1$ is an amino-protecting group, is prepared by attaching a suitable amino-protecting group to compound 34 such as trifluoroacetyl, benzyl, tert-butoxycarbonyl (BOC) or carbobenzyloxy (CBZ), preferably (BOC) by methods known to one of ordinary skill in the art. Briefly, compound 34 is treated with di-tert-butyl-dicarbonate in an aprotic organic solvent such as tetrahydrofuran.

In step 2, a P$^1$- and P$^2$-protected compound 36 where P$^2$ is also an amino-protecting group, is prepared by attaching a suitable amino-protecting group to the phenylamino group such as trifluoroacetyl, benzyl, tert-butoxycarbonyl (BOC) or carbobenzyloxy (CBZ), preferably trifluoroacetyl, to compound 35 by methods known to one of ordinary skill in the art. Briefly, compound 35 is treated with trifluoroacetic anhydride in the presence of a base such as triethylamine. The reaction proceeds under an inert atmosphere in an inert organic solvent such as dichloromethane, dichloroethane or tetrahydrofuran and the like.

In step 3, a $P^2$-protected compound 37 is prepared by removing the $P^1$ amino-protecting group from compound 36 by treatment with a strong organic acid such as trifluoroacetic acid in an inert organic solvent such as halogenated hydrocarbons, for example dichloromethane or dichloroethane.

In step 4, a compound 38 s prepared by reacting compound 37 with a sulfonylating agent such as a sulfonyl halide or an acylating agent such as an acyl halide. The reaction proceeds under an inert atmosphere in the presence of a base, such as triethylamine in a halogenated organic solvent such as dichloromethane or dichloroethane.

In step 5, an phenylamine compound of formula Ik is prepared by removing the $P^2$ amino-protecting group from compound 38 by treatment with a with a base such as lithium hydroxide. Suitable solvents for the reaction include alcoholic or protic solvents such as methanol, ethanol, or water.

An exemplary preparation of a compound of Formula I by this method from the corresponding compound of formula Ik is described in detail in Example 19.

Scheme L

Scheme L describes an alternative method of preparing compounds of Formula I where $R^1$ is a group represented by formula (C) where X is N, and $R^6$ is ——$CONR^8R^9$ or ——$SO_2NR^8R^9$, from the corresponding intermediate compound of formula Il.

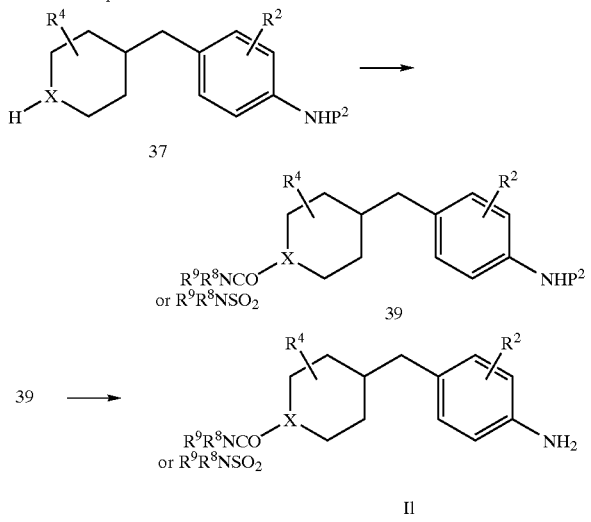

The $P^2$ protected compound 37 is prepared as previously described in Scheme K.

A compound 39 is prepared by reacting compound 37 with a carbamoyl halide or sulfamoyl halide. The reaction proceeds under an inert atmosphere in the presence of a base, such as triethylamine in a halogenated organic solvent such as dichloromethane or dichloroethane.

In the following step, an phenylamine compound of formula Id is prepared by removing the $P^2$-protecting group from compound 39 by treatment with a with a base such as lithium hydroxide. Suitable solvents for the reaction include alcoholic or protic solvents such as methanol, ethanol, or water.

An exemplary preparation of a compound of Formula I by this method from the corresponding compound of formula II is described in detail in Example 20.

Scheme M

Scheme M, in general, describes the preparation of compounds of Formula I where $R^1$ and $R^2$ are as defined in the Summary of the Invention from the corresponding intermediate compounds of formulae Ia – Il.

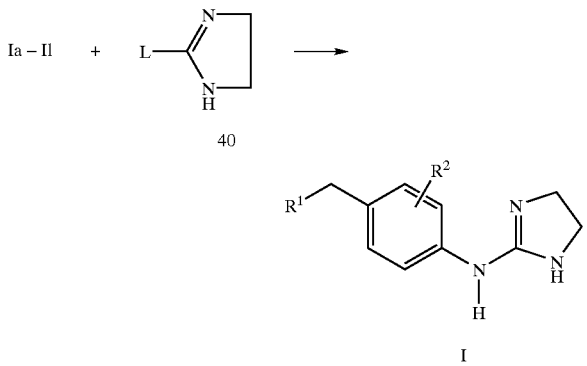

The 2-imidazoline compound of formula 40 is known to or can readily be synthesized by those of ordinary skill in the art. For example, the synthesis of the sulfate salt of formula 40 where L is chloro, is described by A Trani and E. Bellasio, J. Het. Chem., 1974, 11, 257.

In general, the imidazoline compounds of Formula I can be prepared by reacting the corresponding intermediate compounds of formulae Ia–Il with a 2-imidazoline compound 40 as an acid addition salt or tree base. The reaction proceeds on heating under reflux, and typically under an inert atmosphere. Suitable solvents for the reaction are inert organic solvents including methanol, ethanol, isopropanol, dichloromethane, acetonitrile, tetrahydrofuran, dioxane, and the like. The choice of solvent will depend upon the utilization of the acid addition salt or free base.

General Utility

The IP receptor antagonists such as those described in this invention possess both anti-inflammatory and analgesic properties in vivo. Accordingly, these compounds are therefore useful as anti-inflammatory and analgesic agents in mammals, especially humans. They find utility in pain conditions (states) from a wide variety of causes, including but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

The compounds also find utility in inflammatory conditions from a variety of causes, including but not limited to, bacterial, fungal or viral infections, rheumatoid arthritis, osteoarthritis, surgery, bladder infection or idiopathic bladder inflammation, over-use, old age, or nutritional deficiencies, prostatis, conjunctivitis.

The compounds also find utility in bladder disorders associated with bladder outlet obstruction and urinary incontinence conditions such as urge incontinence, stress incontinence, and bladder hyperreactivity.

The compounds also find utility in respiratory conditions such as asthma, in which the C-fibers in the lungs are hyper-responsive to a number of environmental stimuli, including cold air, dust, pollen and other antigens. Since these C-fibers express IP prostanoid receptors, the activation of these receptors by $PGI_2$, and a subsequent release of neurokinins may contribute to the contraction of lung smooth muscle tissues, edema, and mucus secretion. Thus, compounds of this invention given either systemically or with aerosol application may constitute an effective therapy for asthma.

In addition, the compounds also find utility in the treatment of septic shock.

Testing

The anti-inflammatory/analgesic activity of the compounds of this invention may be assayed by in vivo assays such as the Rat Carrageenan-Induced Mechanical Hyperalgesia Paw Assay and the Rat Complete Freund's Adjuvant-induced Mechanical Hyperalgesia Assay, as described in more detail in Examples 30 and 31, respectively. Activity in the inhibition of contractions may be assayed by in vitro assays such as the Inhibition of Bladder Contractions Induced by Isovolumetric Bladder Distension Assay, as described in more detail in Examples 32 and 33. Activity in the inhibition of the septic shock may be assayed by in vivo assays such as the Rat Reversal of Endotoxin-Induced Hypotension Assay, as described in more detail in Example 34.

Administration and Pharmaceutical Composition

The invention includes a pharmaceutical composition comprising a compound of the present invention or a pharmaceutically acceptable salt or a crystal form thereof together with one or more pharmaceutically acceptable carriers, and optionally other therapeutic and/or prophylactic ingredients.

In general, the compounds of this invention will be administered in a therapeutically effective amount by any of the accepted modes of administration for agents that serve similar utilities. Suitable dosage ranges are 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of this invention for a given disease.

In general, compounds of this invention will be administered as pharmaceutical formulations including those suitable for oral (including buccal and sub-lingual), rectal, nasal, topical, pulmonary, vaginal or parenteral (including intramuscular, intraarterial, intrathecal subcutaneous and intravenous) administration or in a form suitable for administration by inhalation or insufflation. The preferred manner of administration is oral using a convenient daily dosage regimen which can be adjusted according to the degree of affliction.

The compounds of the invention, together with a conventional adjuvant, carrier, or diluent, marl be placed into the form of pharmaceutical compositions and unit dosages. The pharmaceutical compositions and unit dosage forms may comprise of conventional ingredients in conventional proportions, with or without additional active compounds or principles, and the unit dosage forms may contain any suitable effective amount of the active ingredient commensurate with the intended daily dosage range to be employed. The pharmaceutical composition may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing one (1) milligram of active ingredient or, more broadly, 0.01 to one hundred 100) milligrams, per tablet, are accordingly suitable representative unit dosage forms.

The compounds of the present invention may be formulated in a wide variety of oral administration dosage forms. The pharmaceutical compositions and dosage forms may comprise the compounds of the invention or its pharmaceutically acceptable salt or a crystal form thereof as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is a mixture with the finely divided active component. In tablets, the active component is mixed with the carrier having the necessary binding capacity in suitable proportions and compacted in the shape and size desired. The powders and tablets preferably containing from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid arms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient n a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, Formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 24 to 29.

EXAMPLES

The following preparations and examples are given to enable those skilled in the art to more clearly understand and to practice the present invention. They should not be considered as limiting the scope of the invention, but merely as being illustrative and representative thereof.

Preparation 1

1-Bromo-4-isopropoxymethylbenzene

60% Sodium hydride in mineral oil (0.96 g, 24 mmol) was added to a solution of isopropanol (7.59 mL, 36 mmol) in dry N,N-dimethylformamide (30 mL) at 0° to 5° C. under argon atmosphere. After the mixture was stirred for about 25 minutes, 4-bromo-benzyl bromide was added and the mixture stirred at 20° C. for an additional 1 hour. The solution was partitioned between saturated ammonium chloride (50 mL) and diethyl ether (50 mL). The aqueous phase was extracted with diethyl ether (3×20 mL), and the combined organic layers were washed with water, dried ($Na_2SO_4$), and evaporated in vacuo. The crude product was filtered over silica gel to give pure 1-bromo-4-isopropoxymethylbenzene (2.33 g, 85%) as clear oil.

Preparation 2

4-Chloromethylphenylcarbamic Acid 2-Trimethylsilaryl Ethyl Ester

To a mixture of 4-chloromethylphenyl isocyanate (1.07g, 6.4 mM) in tetrahydrofuran (22 ml) was added 2-trimethylsilyl ethanol (0.91 mL, 6.4 mmol) at 20–25° C. under argon. The mixture was stirred for 4 hours at 20–25° C. The solvent was evaporated in vacuo. Saturated sodium bicarbonate was added and product was extracted with ethyl acetate. The extract was washed with water, brine, dried ($Na_2SO_4$), and concentrated to dryness. Purification by flash chromatography on silica, eluting with hexane/ethyl acetate, gave crystalline 4-chloromethylphenylcarbamic acid 2-trimethylsilanyl ethyl ester (1.24 g, 68% yield) as a white solid. mp 55–56° C.; $^1$H NMR 7.38 (d, J=8.6, 2H), 7.32 (d, J=8.6, 2H), 6.60 (bs, 1H), 4.55 (S, 2H), 4.26 (m, 2H), 1.05 (m, 2H), 0.06 (s, 9H).

Example 1

2-[4-(4-Isopropoxybenzyl)phenyl]-amino-imidazoline

The following is a preparation of a compound of Formula I from the corresponding compound of formula Ia in which $R^1$ is a group represented by formula (A), $R^2$ and $R^4$ are hydrogen, Y is isopropyl, and m is an integer 0.

Step 1

The compound of formula 3a was prepared according to the procedure of Shani, J. et al., *J. Med. Chem*, 1985, 28, 1504. Thus, a mixture of 4-nitrobenzoyl chloride (90 g, 0.48 mol) and anisole (57.24 g, 0.53 mol) in carbon disulfide (450 mL) was stirred in a three neck round bottom flask equipped with nitrogen inlet, condenser and mechanical stirrer that was being cooled in an ice bath. Aluminum chloride (84.0 g, 0.63 mol) was added in portions and stirring continued at ice bath temperature for 30 minutes, then at room temperature for an additional 1 hour. The reaction mixture was cooled, treated with concentrated hydrochloric acid (150 mL), diluted with cold water (250 mL). The product was collected, filtered, washed, dried, and crystallized from ethyl acetate to give 4-(4-methoxybenzoyl)-nitrobenzene as an off-white solid, m.p. 120–122° C.; Analysis for $C_{14}H_{11}NO_4$: Calc.: C, 65.3; H, 4.31; N, 5.44; Found: C, 66.22; H, 4.16; N, 5.69.

Step 2

A solution of 4-(4-methoxybenzoyl)-nitrobenzene (150 g, 0.58 mol), glacial acetic acid (500 mL), and hydrobromic acid (48% w/w aqueous solution, 400 mL) was heated under reflux for 16 hours. The reaction mixture was cooled to room temperature and poured onto crushed ice. The crude product as filtered, washed several times with water and dried at about 50° C. under high vacuum. Crystallization from ethyl acetate/hexanes gave 4-(4-hydroxybenzoyl)-nitrobenzene (114 g, 81%), m.p. 190–193° C.; Analysis for $C_{13}H_9NO_4$: Calc.: C, 64.20; H, 3.73; N, 5.76; Found: C, 63.95; H, 3.65; N, 5.85; MS m/e (%): 243 (M+; 45).

Step 3

A reaction mixture containing 4-(4-hydroxybenzoyl)-nitrobenzene (48.63 g, 0.2 mol), 2-bromopropane (98.4 g, 0.8 mol), sodium iodide (1.5g) and anhydrous potassium carbonate (27.6 g, 0.2 mol) in N,N-dimethylformamide (200 mL) was heated at about 60–70° C. under nitrogen for 18 hours. The reaction mixture was concentrated, and the residue stirred with water and filtered. The crude product was washed several times with water and dried to give a cream-colored product (54.8 g, 96%), which was then crystallized from ethyl acetate to give 4-(4-isopropoxbenzoyl)-nitrobenzene, m.p. 138° C.; Analysis for $C_{16}H_{15}NO_4$: C, 67.36; H, 5.30; N, 4.91; Found: C, 67,39; H, 5.28; N, 5.07.

Step 4

A mixture of 4-(4-isopropoxybenzoyl)-nitrobenzene (14.0 g, 49.09 mmol) and 10% palladium on carbon (2.0 g) in a solution of ethanol (250 mL) and concentrated hydrochloric acid (30 mL) was hydrogenated at 50 psi in a Parr apparatus for 16 hours. The catalyst was removed by filtration through a Celite pad, and filtrate was concentrated in vacuo. The residue was diluted with ice cold water, basified with concentrated ammonium hydroxide solution, and extracted into ethyl acetate. The organic extracts were washed with water and brine, and dried ($MgSO_4$). Removal of the solvent gave a thick oil which on crystallization from ethyl acetate/hexanes gave 4-(4-isopropoxybenzyl)-phenylamine (10.4 g, 87%) as a white solid, m.p. 92–93° C.; Analysis for $C_{16}H_{19}NO$: Calc.: C, 79.63; H, 7.94; N, 5.80; Found: C, 79.51; H,7.92; N, 5.96. MS m/e (%): 241 (M+, 83).

Last Step

2-Chloro-2-imidazoline sulfate was prepared according to the procedures described in A. Trani and E. Bellasio., *J. Het. Chem.*, 1974, 11, 257.

A mixture of 2-chloro-2-imidazoline sulfate (24.36 g, 120 mmol) and 4-(4-isopropoxybenzyl)-phenylamine (24.1 g, 100 mmol) in isopropanol (300 mL) was heated under reflux for 1–2 hours under an inert atmosphere. The reaction mixture was concentrated in vacuo and the residue diluted with ice cold water. The mixture was basified with 10% sodium hydroxide and thoroughly extracted with dichloromethane. The combined organic extracts were washed with cold water and brine, dried ($K_2CO_3$), and concentrated. Crystallization from diethylether/hexanes gave 2-[4-(4-isopropoxybenzyl)phenyl]-amino-imidazoline (9.94 g, 96%) as an off-white solid, m.p. 103–104° C.; Analysis for $C_{19}H_{22}N_3O$: C, 73.76; H, 7.49; N, 13.58; Found. C, 73.51; H, 7.42; N, 13.57; MS m/e (%): 309 (M+; 100).

A solution of sulfuric acid (0.08 g) in acetone (1 mL) was added to a mixture of 2-[4-(4-isopropoxybenzyl)phenyl]-amino-imidazoline (0.5 g) in acetone (14 mL). The mixture was warmed, stirred for 15 minutes, and filtered to give 2-[4-(4-isopropoxybenzyl)-phenyl]amino-imidazoline sulfate (0.56 g) as a white solid, m.p. 215–216° C.; Analysis for $C_{38}H_{48}N_6O_6S$: C, 63.66; H, 6.75; N, 11.72; Found; C 63.50; H, 6.64; N, 11.72.

Proceeding as in Example 1, step 1, and proceeding directly to Example 1, step 4 and last step, gave 2-[4-(4-methoxybenzyl)phenyl]amino-imidazoline, m.p. 114–116° C.

Proceeding as in Example 1, step 1, but replacing 4-nitrobenzoyl chloride with 3-methoxy-4-nitrobenzoyl chloride and proceeding directly to Example 1, step 4 and last step, gave 2-[4-(4-methoxybenzyl)-3-methoxyphenyl]amino-imidazoline, m.p. 127–128° C.

Proceeding as in Example 1, step 3, but replacing 2-bromopropane with ethyl 2-bromopropionate, and then correspondingly as in Example 1, subsequent steps, gave 2-{4-[4-(4,5-dihydro-H-imidazol-2-ylamino)benzyl]phenoxy}propionic acid, m.p.>300° C.; Analysis for $C_{19}H_{21}N_{33}$: Calc.: C, 67.24; H 6.24, N, 12.38; Found: C, 66.90; H 6.23, N, 12.31.

Proceeding as in Example 1, step 3, but replacing 2-bromopropane with other alkyl halides, and then correspondingly as in Example 1, subsequent steps, the following compounds of Formula I were prepared:

- 2-[4-(4-ethoxybenzyl)phenyl]amino-imidazoline, m.p. 152–153° C.;
- 2-{4-[4-(2,2,2-trifluoroethoxy)benzyl]phenyl}amino-imidazoline hydrochloride, m.p. 75–78° C.;
- 2-[4-(4-propoxybenzyl)phenyl]amino-imidazoline oxalate, m.p. 14–147° C.;
- 2-[4-(4-butoxybenzyl)phenyl]amino-imidazoline hydrochloride, m.p. 97–100° C.;
- 2-[4-(4-butoxybenzyl)phenyl]amino-imidazoline oxalate, m.p. 172–174° C.;
- 2-[4-(4-isobutoxybenzyl)phenyl]amino-imidazoline hydrochloride, m.p. 127–129° C.:
- 2-[4-(4-pentyloxybenzyl)phenyl]amino- imidazoline oxalate, m.p. 163–166° C.;
- 2-{4-[4-(1-methylbutoxy)benzyl]phenyl}amino-imidazoline, m.p. 99–112° C.;

2-{4-[4-(2-hydroxypropoxy)benzyl]phenyl}amino-imidazoline hydrochloride, m.p. 129–133° C.;

2-{4-[4-(3-hydroxy-2-hydroxymethylpropoxy)benzyl]phenyl}amino-imidazoline maleate, m.p. 70–75° C.;

2-[4-(4-benzyloxybenzyl)phenyl]amino-imidazoline hydrochloride, Analysis for $C_{23}H_{24}N_3OCl$: Calc.: C, 70.13; H 6.14, N, 10.67; Found: C, 69.79; H 6.10, N, 10.74;

2-[4-(4-cyclopentyloxybenzyl)phenyl]amino-imidazoline hydrochloride, m.p. 116–119° C.;

2-[4-(4-cyclohexoxybenzyl)phenyl]amino-imidazoline hydrochloride, m.p. 108–110° C.;

2-[4-(4-cyclohexylmethoxybenzyl)phenyl]amino-imidazoline hydrochloride, m.p. 95–100° C.;

2-[4-(4-tetrahydropyran-2-yloxybenzyl)phenyl]amino-imidazoline oxalate, m.p. 168–170° C.;

2-{4-[2-(4-methoxyphenyl)ethoxybenzyl]phenyl}amino-imidazoline, m.p. 122–124° C.;

2-[4-(4-benzoylmethoxybenzyl)phenyl]amino-imidazoline hydrochloride, Analysis for $C_{24}H_{24}N_3O_2Cl$: Calc.: C, 67.28; H 5.86, N, 9.81; Found: C, 67.27; H 5.76, N, 9.62;

2-{4-[4-(cyclopentylaminocarbonyl)methoxybenzyl]phenyl}amino-imidazoline hydrochloride, m.p. 78–81° C.;

2-{4-[4-(1-piperidinecarbonyl)methoxybenzyl]phenyl}amino-imidazoline hydrochloride, m.p. 65–67° C.;

2-{4-[4-(phenylaminocarbonyl)methoxybenzyl]phenyl}amino-imidazoline hydrochloride, m.p. 186–187° C.;

2-{4-[4-(diisopropylaminocarbonyl)methoxybenzyl]phenyl}amino-imidazoline hydrochloride, m.p. 62–65° C.;

2-{4-[4-(diethylaminocarbonyl)methoxybenzyl]phenyl}amino-imidazoline hydrochloride, Analysis for $C_{22}H_{29}N_4O_2Cl$: Calc.: C, 60.75; H7.18, N, 12.88; Found: C, 60.91.; H 7.04, N, 12.95;

2-{4-[4-(isopropylaminocarbonyl)methoxybenzyl]phenyl}amino-imidazoline hydrochloride, m.p. 66–78° C.;

2-{4-[4-(N-isopropyl-N-methylaminocarbonyl)methoxybenzyl]phenyl}amino-imidazoline hydrochloride, m.p. 77–81° C.;

2-{4-[(4-methoxyphenyl)aminocarbonylmethoxybenzyl]phenyl}amino-imidazoline hydrochloride, Analysis for $C_{25}H_{27}N_4O_3Cl$: Calc.: C, 63.33; H 5.91, N, 11.82: Found C, 63. 04; H 5.78, N, 11.67;

2-[4-(2-fluoro-4-propoxylbenzyl)phenyl]amino-imidazoline oxalate, m.p. 130–133° C.;

2-[4-(3-fluoro-4-isopropoxylbenzyl)phenyl]amino-imidazoline oxalate, m.p. 120–121° C.;

2-[4-(2-fluor-4-tetrahydropyran-2-ylmethoxybenzyl)phenyl]amino-imidazoline maleate, m.p. 138–141° C;

2-[4-(3-chloro-4-isopropoxybenzyl)phenyl]amino-imidazoline hydrochloride, m.p. 118–120° C.;

2-[4-(2-fluoro-4-methoxybenzyl)phenyl]amino-imidazoline hydrochloride, m.p. 126–129° C.;

2-[4-(3-fluoro-4-methoxybenzyl)phenyl]amino-imidazoline hydrochloride, m.p. 138–140° C.;

2-[4(4-fluoro-2-methoxybenzyl)phenyl]amino-imidazoline hydrochloride, m.p. 230–233° C.;

2-[4-(2,4-dimethoxybenzyl)phenyl]amino-imidazoline hydrochloride, m.p. 137–143° C.;

2-[4-(3,4-dimethoxybenzyl)phenyl]amino-imidazoline hydrochloride, m.p. 127–128° C.; and 2-[4-(3-chloro-4-methoxybenzyl)phenyl]amino-imidazoline hydrochloride, m.p. 169–172° C.

Example 2

2-[4-(4-Tetrahydropyran-4-yloxybenzyl)phenyl]-amino-imidazoline

The following is an alternative preparation of a compound of Formula I from the corresponding compound of formula Ia in which $R^1$ is a group represented by formula (A), $R^2$ and $R^4$ are hydrogen, Z is 4-tetrahydropyran-4-yl, and n is an integer 0.

2-[4-(4-Tetrahydropyran-4-yloxybenzyl)phenyl]-amino-imidazoline was prepared by proceeding as in Example 1, steps 1 and 2, and then to Alternative Step 3:

Diethyl azodicarboxylate (1.47 g, 8.4 mmol) was slowly added dropwise to a solution of 4-(4-hydroxybenzoyl)-nitrobenzene (1.7 g, 7mmol) (prepared as described in Example 1, steps), 4-hydroxytetrahydropyran (0,78 g, 7.7 mmol) and triphenylphosphine (2.2 g, 8.4mmol) in dry tetrahydrofuran (20 mL) while stirring at room temperature under inert atmosphere. The reaction mixture was stirred for an additional hour then quenched with water (1 mL) and concentrated in vacuo. The residue was diluted with water and extracted with ethyl acetate The combined organic extracts were washed with water and brine, dried ($Na_2SO_4$), and concentrated in vacuo. The crude product was chromatographed on silica gel (25% ethyl acetate/hexanes) and crystallized from hexanes to give 4-(4-tetrahydropyran-4-yloxybenzoyl)-nitrobenzene (1.4 g, 61%) as a white solid, m.p. 105–106 ° C.; Analysis for $C_{18}H_{17}NO_5$: Calc.: C, 66.05; H, 5.23; N, 4.28; Found: C, 65.95; H, 3.14; N, 4.38. MS m/e (%): 283 (M+; 100).

Proceeding as in Example 1, steps 4 and last step, but replacing 4-(4-isopropoxybenzoyl)-nitrobenzene with 4-(4-tetrahydropyran-4-yloxybenzoyl)-nitrobenzene, gave 2-[4-(4-tetrahydropyran-4-yloxybenzyl)phenyl]amino-imidazoline, m.p.169–170° C.

Proceeding as in Example 2, but replacing 4-hydroxytetrahydropyran in with other hydroxy compounds, the following compounds of Formula I were prepared:

2-{4-[4-(1-ethylpropoxy)benzyl]phenyl}amino-imidazoline, Analysis for $C_{21}H_{27}N_3O$: Calc.: C, 74.74; H 8.06, N, 12.45; Found: C, 74.62; H 7.90, N, 12.33;

2-{4-[4-(sec-butoxy)benzyl]phenyl}amino-imidazoline hydrochloride, m.p. 118–119° C.;

(R)-2-{4-[4-(sec-butoxy)benzyl]phenyl}amino-imidazoline maleate, m.p. 163–164° C;

(S)-2-{4-[4-(sec-butoxy)benzyl]phenyl}amino-imidazoline maleate, m.p. 163° C.;

(S)-2-{4-[4-(2-methylbutoxy)benzyl]phenyl}amino-imidazoline hydrochloride, m.p. 119–122° C.;

2-[4-(4-hexyloxybenzyl)phenyl]amino-imidazoline oxalate, m.p. 150–161° C;

2-{4-[4-(2-methoxyethoxy)benzyl]phenyl}amino-imidazoline, m.p. 110–112° C.;

2-[4-(4-hydroxybenzyl)phenyl]amino-imidazoline, m.p. 170–177° C.;

2-{4-[4-(2-hydroxyethoxy)benzyl]phenyl}amino-imidazoline, m.p. 164–165° C.;

2-{4-[4-(3-ethoxypropoxy)benzyl]phenyl}amino-imidazoline hydrochloride, m.p. 91–92° C.;

2-[4-(4-chlorobutoxy)benzyl]phenyl}amino-imidazoline, Analysis for $C_{20}H_{24}N_3OCl$: Calc.: C, 67.12; H 6.76, N, 11.74; Found: C, 66.84; H 6.79, N, 11.80;

2-{4-[4-(2-methoxy-1-methylethoxy)benzyl]phenyl}amino-imidazoline hydrochloride, m.p. 71–74° C.;

2-{4-[4-(3-methoxybutoxy)benzyl]phenyl}amino-imidazoline hydrochloride, m.p. 71–76° C.;

2-{4-[4-(1-hydroxymethylethoxy)benzyl]phenyl}amino-imidazoline hydrochloride, m/s 326 (M+1);

2-{4-[4-(2-hydroxy-1-hydroxymethylethoxy)benzyl]phenyl}amino-imidazoline hydrochloride, m.p. 50–55° C.;

2-{4-[4-(2-ethoxy-1-ethoxymethyl)ethoxybenzyl]phenyl}amino-imidazoline hydrochloride, gum;

2-{4-[4-(2,3-dihydroxypropoxy)benzyl]phenyl}amino-imidazoline hydrochloride, m.p. 55–60° C.;

2-{4-[4-(2-phenylethoxy)benzyl]phenyl}amino-imidazoline hydrochloride, Analysis for $C_{24}H_{26}N_3OCl$: Calc.: C, 70.66; H 6.42, N, 10.30; Found: C, 70.42; H 6.37, N, 10.42.;

2-{4-[4-(2-phenoxyethoxy)benzyl]phenyl}amino-imidazoline hydrochloride, m.p. 140–141° C.;

2-{4-[4-(3-phenylpropoxy)benzyl]phenyl}amino-imidazoline hydrochloride, m.p. 101–104° C.;

2-[4-(4-cyclopropylmethoxybenzyl)phenyl]amino-imidazoline hydrochloride, m.p. 121–122° C.;

2-[4-(4-cyclobutylmethoxybenzyl)phenyl]amino-imidazoline, Analysis for $C_{21}H_{25}N_3O$: Calc.: C, 75.19; H 7.51, N, 12.53; Found: C, 74.69; H 7.32, N, 11.96;

2-{4-[4-(2-cyclopentylethoxy)benzyl]phenyl}amino-imidazoline oxalate, m.p. 152–153° C.;

2-{4-[4-(2-cyclohexylethoxy)benzyl]phenyl}amino-imidazoline maleate, m.p. 144–147° C.;

2-{4-[4-(2-cyclohexyloxyethoxy)benzyl]phenyl}amino-imidazoline oxalate, m.p. 120–127° C.;

2-{4-[4-(2-isopropoxyethoxy)benzyl]phenyl}amino-imidazoline hydrochloride, m.p. 76–80° C.;

2-{4-[4-(2-(2-oxo-pyrrolidin-1-yl)ethoxy)benzyl]phenyl}amino-imidazoline hydrochloride, m.p. 143–145° C.;

2-{4-[4-(2-(2-oxo-imidazolin-1-yl)ethoxy)benzyl]phenyl}amino-imidazoline hydrochloride, m.p. 85–88° C.;

2-[4-(4-tetrahydropyran-4-ylmethoxybenzyl)phenyl]amino-imidazoline, m.p.159–160° C.;

2-[4-(4-tetrahydrofuran-3-ylmethoxybenzyl)phenyl]amino-imidazoline, m.p. 147–149 C;

2-[4-(4-tetrahydrofuran-3-yloxybenzyl)phenyl]amino-imidazoline, m.p. 149–150° C.;

2-{4-[4-(4-methylcyclohexyloxy)benzyl]phenyl}amino-imidazoline, m.p. 80–85° C.;

2-{4-[4-(5-methyl-[1,3]dioxan-5-ylmethoxy)benzyl]phenyl}amino-imidazoline hydrochloride, m.p. 85–90° C.;

2-{4-[4-(3-chloro-2-hydroxymethyl-2-methylpropoxy)benzyl]phenyl}amino-imidazoline hydrochloride, m.p. 65–70° C.;

2-{4-[4-(2-thien-2-ylethoxy)benzyl]phenyl}amino-imidazoline hydrochloride, Analysis for $C_{22}H_{24}N_3OClS$: Calc.: C, 63.83; H 5.84, N, 10.15; Found: C, 63.85; H 5.80, N, 10.14;

2-{4-[4-(2-thien-3-ylethoxy)benzyl)phenyl]amino-imidazoline hydrochloride, Analysis for $C_{22}H_{24}N_3OClS$: Calc.: C, 63.14; H 5.90, N, 10.04; Found: C, 63.30; H 5.81, N, 10.11;

2-{4-[4-(2-methanesulfonylethoxy)benzyl]phenyl}amino-imidazoline hydrochloride, m.p. 172–175° C.;

2-{4-[4-(4-methoxyphenyl)sulfonylaminoethoxybenzyl]phenyl}amino-imidazoline hydrochloride, Analysis for $C_{26}H_{31}N_4O_6ClS$: Calc.: C, 58.08; H 5.95, N, 10.41; Found: C, 57.97; H 9.94, N, 10.58;

2-[4-(3-fluoro-4-isobutoxybenzyl)phenyl]amino-imidazoline oxalate, m.p. 134–135° C.;

2-[4-(2-fluoro-4-isobutoxybenzyl)phenyl]amino-imidazoline hydrochloride, m.p. 134–135° C.;

2-{4-[3-fluoro-4-(tetrahydropyran-4-yloxy)benzyl]phenyl}amino-imidazoline hydrochloride, m.p. 149–151° C.;

2-{4-[2-fluoro-4-(tetrahydropyran-4-yloxy)benzyl]phenyl}amino-imidazoline, m.p. 169–170° C.;

2-{4-[4-(tetrahydropyran-4-ylmethoxy)benzyl]phenyl}amino-imidazoline, m.p. 124–127° C;

2-{4-[3-fluoro-4-(tetrahydropyran-4-ylmethoxy)benzyl]phenyl}amino-imidazoline, m.p. 154–155° C.;

2-{4-[2-fluoro-(4-tetrahydropyran-4-ylmethoxy) benzyl]phenyl}amino-imidazoline maleate, m.p. 134–135° C;

2-{4-[2-fluoro-4-pentyloxybenzyl]phenyl}amino-imidazoline hydrochloride, m.p. shrinks at 72° C.;

2-{4-[4-(2-isopropoxyethoxy)benzyl]phenyl}amino-imidazoline oxalate, m.p. 134–137° C.;

2-[4-(3-chloro-4-isobutoxybenzyl)phenyl]amino-imidazoline, m.p. 126–128° C.; and 2-{4-[3-chloro-4-(tetrahydropyran-4-yloxy)benzyl]phenyl}amino-imidazoline hydrochloride, m.p. 128–130° C.

Example 3

2-[4(4-Isopropoxybenzyl)phenyl]-amino-imidazoline

The following s an alternative preparation of a compound of Formula I from the corresponding compound of formula Ia in which $R^1$ is a group represented by formula (A), $R^2$ and $R^4$ are hydrogen, Y is isopropoxy, and m is an integer 0.

Step 1

A mixture of 4-bromophenol (30.0 g, 173 mmol), potassium carbonate (26.3 g, 190 mol), sodium iodide (0.60 g, 4 mmol), 2-bromopropane (85.1 g, 0.692 mmol), and N,N-dimethylformamide (173 mL) was warmed at 60° C. for 17 hours. The solution was cooled to room temperature and water (300 mL) was added. The solution was extracted with diethyl ether. The extract was washed with aqueous sodium hydroxide, water, and aqueous sodium chloride, dried ($Na_2SO_4$), filtered, and concentrated. The product was purified by vacuum distillation to give 4-bromo-isopropoxybenzene (25.3 g, 118 mmol) as a colorless liquid.

Step 2

A mixture of magnesium (0.534 g, 22.0 mmol) and tetrahydrofuran (20 mL) under nitrogen was brought to reflux. To the solution was slowly added 4-bromo-isopropoxybenzene (3.10 g, 14.4 mmol) and to ensure initiation of the reaction 1,2-dibromoethane (0.74 g, 3.93 mmol). After completion of the Grignard reaction, the solution was cooled to room temperature and 0.5M zinc chloride in tetrahydrofuran (14.5 mL, 7.3 mmol) was added. The solution was warmed to reflux to 30 minutes then cooled to room temperature.

Step 3

A mixture of 4-nitrobenzoyl chloride (1.47 g, 7.92 mmol), tetrakis(triphenylphosphine)palladium (0.46 g, 0.40 mmol), and tetrahyrofuran (10 mL) under nitrogen was cooled in an ice water bath. To the solution was added a portion of the diarylzinc solution (3.5 mmol). The solution was stirred for 1 hour in the ice water bath, then overnight at room temperature. The solution was diluted with water (15 mL) and concentrated. The concentrate was extracted with dichloromethane. The extract was dried ($MgSO_4$), filtered and concentrated. The residue was purified using silica gel chromatography to give 4-isopropoxybenzoyl-4-nitrobenzene (1.0 g, 3.5 mmol), m.p. 135.6–136.9° C.

Last Step

Proceeding as described in Example 1, last step, gave 2-[4-(4-isopropoxbenzyl)-phenyl]amino-imidazoline, as an identical product as that obtained in Example 1.

Example 4

2-[4-(4-Isopropoxymethylbenzyl)phenyl]-amino-imidazoline

The following is an alternative preparation of a compound of Formula I from the corresponding compound of formula Ia in which $R^1$ is a group represented by formula (A), $R^2$ and $R^4$ are hydrogen, Y is isopropyl, and m is an integer 1.

Step 1

To a stirred solution of 1-bromo-4-isopropoxymethyl-benzene (300 mg, 13.1 , mmol) (prepared as described in Preparation 1) in dry tetrahydrofuran (1.4 mL) at −78° C. under argon atmosphere was added dropwise 1 .7M tert-butyllithium in pentane (1.62 mL, 2.75 mmol). After the mixture was stirred for about 20 minutes, tri-n-butyltin chloride (0.35 mL, 1.31 mmol) was added. The mixture was allowed to reach 0° to 5° C. and stirred for about 1 hour. A mixture of (4-chloromethylphenyl) carbamic acid 2-trimethylsilanyl-ethyl ester (374 mg, 13.1 mmol) (prepared as described in Preparation 2), hexamethylphosphoramide (4.4 mL), tetrakis(triphenylphosphine)palladium (0) (29.3 mg, 0.025 mmol) was added at 0° to 5° C., and then heated to about 65° C. for 20 hours. The solution was partitioned between water (15 mL) and diethyl ether (15 mL). The aqueous phase was extracted with diethyl ether, and the combined organic layers were washed with water and brine, dried ($Na_2SO_4$), and evaporated in vacuo. The residue was dissolved in acetonitrile, washed with hexane (2×20 mL), dried ($Na_2SO_4$), concentrated in vacuo, and purified by flash chromatography to give pure 4-(4-isopropoxymethylbenzyl)phenyl carbamic acid 2-trimethylsilanyl-ethyl ester (204 mg, 26%) as clear oil.

Step 2

To a solution of 4-(4-isopropoxymethylbenzyl)phenyl carbamic acid 2-trimethylsilanylethyl ester (734 mg, 1.84 mmol) in dry dimethyl sulfoxide at 20° C. under argon atmosphere was added tetra-n-butylammonium fluoride in tetrahydrofuran (5.52 mL, 5.52 mmol). After the mixture was stirred for 1 hour, the solution was partitioned between water (50 mL) and diethyl ether (50 mL). The aqueous phase was extracted with diethyl ether (2×20 mL), and the combined organic layers were washed with water and brine, dried ($Mg_2SO_4$), and evaporated in vacuo. The crude product was purified by flash chromatography to give pure 4-(4-isopropoxymethyl-benzyl)-phenylamine (405 mg, 86%) as a clear oil.

Last Step

To a solution of 4-(4-isopropoxymethylbenzyl)-phenylamine (400 mg, 1.57 mmol) in isopropanol (4.8 mL) at 20° C. under argon atmosphere was added 2-chloro-2-imidazoline sulfate (382 mg, 1.88 mmol). The mixture was heated to 80° C. and stirred for 3 hours. The solvent was evaporated in vacuo, and water and 10% sodium hydroxide was added to pH 11–12. The basic aqueous phase was extracted with dichloromethane (3×20 mL), and the combined organic layers were washed with water, dried ($Na_2SO_4$), and evaporated in vacuo. The crude product was purified by flash chromatography, washed with 0.07M potassium carbonate, and concentrated to give pure 2-[4-(4-isopropoxymethyl-benzyl)-phenyl]-imidazoline (463 mg, 91%) as a clear oil.

Oxalic acid (129 mg, 1.43 mmol) was added to 2-[4-(4-isopropoxymethyl-benzyl)-phenyl]-imidazoline and recrystallized from acetone to give 2-[4-(4-isopropoxymethyl-benzyl)-phenyl]-imidazoline oxalate (507 mg) as a white crystalline solid, m.p. 156.3–156.7° C.; Analysis for $C_{20}H_{25}N_3O.C_2H_2O_4$: Calc.: C, 63.91; H, 6.58; N, 10.16; Found: C, 63.98; H, 6.53; N, 10.24.

Proceeding as in described in Example 4, step 1, but replacing 1-bromo-4-isopropoxymethyl-benzene with 1-bromo-4-sec-butoxymethyl-benzene, and then correspondingly as in subsequent steps, gave 2-[4-(4-sec-butoxymethylbenzyl)-phenyl]-imidazoline oxalate, m.p. 145.0–145.3° C.; Analysis for $C_{21}H_{27}N_3O.C_2H_2O_4$: Calc.: C, 65.62; H, 6.84; N, 9.83; Found: C, 64.81; H, 6.82; N, 9.98.

Example 5

2-[4-(4-Morpholinobenzyl)phenyl]amino-imidazoline

The following is an alternative preparation of a compound of Formula I from the corresponding compound of formula Ib in which $R^1$ is a group represented by formula (A), $R^2$ and $R^4$ are hydrogen, and $R^3$ is morpholino.

Step 1

Aluminum chloride (26.0 g, 195 mmol) was added in portions to a solution of 4-nitrobenzoyl chloride (27.8 g, 150 mL) and 4-fluorobenzene (15.8 g, 165 mmol) in carbon disulfide (100 mL). After 1 hour, the resulting yellow mixture was carefully treated with concentrated hydrochloric acid (60 mL) and stirred for 30 minutes. The mixture was then diluted with water and extracted with ethyl acetate. The organic layer was washed with dilute sodium hydroxide solution, water and brine, dried ($MgSO_4$), and the solvent removed in vacuo. Crystallization from ethyl ether/hexanes gave 4-(4-fluorobenzoyl)-nitrobenzene (10.6 g, 82%) as a white solid, m.p. 87–88° C.; Analysis for $C_{13}H_8NO_3F$: Calc.: C, 63.69; H, 3.26; N, 5.74: Found: C, 63.89; H, 3.28; N, 5.78.

Step 2

A mixture containing 4-(4-fluorobenzoyl)-nitrobenzene (1.96 g, 8 mmol), morpholine (0.84 g, 9.6 mmol), and potassium carbonate (1.33 g, 9.6 mmol) in dimethyl sulfoxide (15 mL) was heated to 100–110° C. for 12 hours. The reaction mixture was cooled to room temperature and diluted with cold water, and filtered. The crude product was washed several times with water and dried to give 4-(4-morpholinobenzoyl)-nitrobenzene (2.28 g, 91%), m.p. 173–175° C., and was used in the next step without further purification.

Step 3

4-(4-Morpholinobenzoyl)-nitrobenzene (1.0 g) was hydrogenated at 50 psi using 10% palladium on carbon in ethanol and mineral acid as described previously in Example 1, Step 5. The product thus obtained, 4-(4-morpholinobenzyl)-phenylamine (0.66 g, 77%) was used in the next step without further purification.

Last Step

Proceeding as described in Example 1, last step, but replacing 4-(4-isopropoxybenzyl)-phenylamine with 4-(4-morpholinobenzyl)-phenylamine (0.63 g), gave 2-[4-(4-morpholinobenzyl)phenyl]amino-imidazoline (0.51 g, 63%), m.p. 177–179° C.; Analysis for $C_{20}H_{24}N_4O$: Calc.: C, 71.44; H, 7.14; N, 16.66; Found: C, 71.62; H, 7.24; N, 16.41.

Proceeding as in Example 5, step 1, and then correspondingly as in Example 5, step 3 and last step, gave 2-[4-(4-fluorobenzyl)phenyl]amino-imidazoline, m.p. 110–112° C.

Proceeding as in Example 5, step 2, but replacing morpholine with N,N-(2-hydroxyethyl)amine, and then correspondingly as in Example 5, subsequent steps, gave 2-{4-[4-(N,N-(2-hydroxyethyl)amino)-benzyl]phenyl}amino-imidazoline, m.p. 150–152° C.

Proceeding as in Example 5, step 1, but replacing 4-fluorobenzene with 2,4-difluorobenzene, and then correspondingly as in Example 5, step 3 and last step, gave 2-[4-(2,4-difluorobenzyl)phenyl]amino-imidazoline hydrochloride, m.p. 150–152° C.

Proceeding as in Example 5, step 1, but replacing 4-fluorobenzene with alkylated benzenes, and then correspondingly as in Example 5, subsequent steps, the following compounds of Formula I were prepared:

2-[4-(4-ethylbenzyl)phenyl]amino-imidazoline hydrochloride, m.p. 72–74° C;

2-[4-(4-isopropylbenzyl)phenyl]amino-imidazoline fumarate, Analysis for $C_{19}H_{23}N_3 0.35 C_4H_4O_2$: Calc.: C, 62.60; H, 6.28; N, 9.78; Found: C, 62.61, H, 6.44; N, 10.00;

2-[4-(4-isobutylbenzyl)phenyl]amino-imidazoline fumarate, m.p. 182–184° C.;

2-{4-(4-(3-methylbutyl)benzyl]phenyl}amino-imidazoline hydrochloride, Analysis for $C_{21}H_{28}N_3Cl$: Calc.: C, 69.94; H, 7.91; N, 7.76; Found: C, 69.84, H., 11.65, N, 11.75;

2-[4-(4-propylbenzyl)phenyl]amino-imidazoline hydrochloride, Analysis for $C_{19}H_{24}N_3O$: Calc.: C, 68.07; H, 7.39; N, 12.53; Found: C, 68.05, H, 7.21, N, 12.70;

2-[4-(4-cyclopentyl)benzyl]phenyl}amino-imidazoline fumarate, Analysis for $C_{25}H_{29}N_3O_4$: Calc.: C, 62.20; H, 6.19; N, 8.43; Found: C, 62.42, H, 6.23, N, 8.63; and 2-[4-(4-cyclohexyl)benzyl)phenyl]amino-imidazoline fumarate, Analysis for $C_{22}H_{28}N_3Cl$: Calc.: C, 68.43; H, 7.78; N, 10.88; Found: C, 68.36, H, 7.45, N, 11.23.

Example 6

2-{4-[4-(4-Methoxyphenyl)sulfonylaminomethylbenzyl]-phenyl}amino-imidazoline

The following is an alternative preparation of a compound of Formula I from the corresponding compound of formula Ic in which $R^1$ is a group represented by formula (A), $R^2$, $R^4$ and $R^7$ are hydrogen, $R^9$ is 4-methoxyphenyl, and m is an integer 1.

Step 1

Aluminum chloride (9.3 g) was added in a single portion to a mixture of 4-nitrobenzoyl chloride (10 g) and toluene (6.3 mL) dissolved in carbon disulfide (35 mL). The mixture was warmed from room temperature to reflux and heated for 3 hours. Concentrated hydrochloric acid (19 mL) was slowly added, and the mixture stirred for an additional 30 minutes, poured into water, and extracted with dichloromethane (3×). The extract was washed with dilute ammonium hydroxide and water, dried ($Na_2SO_4$), and evaporated. Recrystallization from ethyl acetate gave 4-(4-methylbenzoyl)-nitrobenzene (10.6 g, 82%) as a pale yellow solid, m.p. 122.4–123.1° C.

Step 2

Benzoyl peroxide (0.012 g) was added to a mixture of 4-(4-methylbenzoyl)-nitrobenzene (1.20 g) and N-bromo succinimide (0.89 g) suspended in carbon tetrachloride (63 mL). The reaction mixture was refluxed under argon for 4 hours while illuminated with an incandescent lamp. The mixture was filtered, and the yellow solution containing the crude product was evaporated, chromatographed on silica gel, eluting with hexane/ethyl acetate, to give 4-(4-bromomethylbenzoyl)-nitrobenzene (1.79 g, 81%) as a white solid, m.p. 112.7–113.1° C.

Step 3

4-(4-bromomethylbenzoyl)-nitrobenzene (500 mg) was dissolved in dichloromethane (5 mL) and stirred under argon. A solution of trifluoromethanesulfonic acid (0.27 mL) in dichloromethane (2 mL) was added dropwise, followed by a solution of triethylsilane (0.37 mL) in dichloromethane (2 mL). After 5 minutes, a second portion of trifluoromethanesulfonic acid and triethylsilane (same proportions) was added. The reaction mixture was stirred at room temperature for 3 hours, poured into excess aqueous sodium bicarbonate, and extracted with dichloromethane (3×). The solution containing the crude product was evaporated, chromatographed on silica gel, eluting the product with hexane/ethyl acetate, and evaporated to dryness, to give 4-(4-bromomethylbenzyl)-nitrobenzene (270 mg, 56%).

Step 4

Sodium azide (210 mg, 1.15 eq) was added to a solution of 4-(4-bromomethylbenzyl)-nitrobenzene (901 mg) in N,N-dimethylformamide (10 mL). The reaction mixture was stirred at room temperature for 2 hours, poured into water, and extracted with diethyl ether (3×). The organic phase was washed with water (3×), dried ($MgSO_4$), and evaporated to dryness. Chromatography on silica gel, eluting with hexane/ethyl acetate, gave 4-(4-azidomethylbenzyl)-nitrobenzene (492 mg, 62%) as a yellow oil.

Step 5

A solution of 4-(4-azidomethylbenzyl)-nitrobenzene (5.835 g) in tetrahydrofuran (175 mL) was treated with water (0.43 mL) and triphenylphosphine (6.45 g, 1.1 eg). The mixture was stirred at room temperature for 18 hours, and the solvent was evaporated. The residue was suspended in water, and suspension made acidic by the dropwise addition of hydrochloric acid to about pH 1, then extracted with diethyl ether (3×). The aqueous phase was made alkaline with 50% aqueous sodium hydroxide, extracted with dichloromethane (3×) to afford a crude brown oil (5.66 g). Chromatography on silica gel, eluting with dichloromethane/methanol/ammonium hydroxide, gave 4-(4-aminomethylbenzyl)-nitrobezene (3.91 g, 79%) as a yellow solid.

Step 6

4-(4-Aminomethylbenzyl)-nitrobenzene (500 mg) was dissolved in dichloromethane (7 mL) and heated with 4-methoxybenzenesulfonyl chloride (426 mg) and triethylamine (0.3 mL). The mixture was stirred at room temperature for 15 hours, poured into dilute aqueous hydrochloric acid, and extracted with dichloromethane (3×). The solvent was evaporated to give 4-[4-(4-methoxyphenyl) sulfonylaminomethylbenzyl]-nitrobenzene as a yellow solid (851 mg, ~100%), and was used in the next step without further purification.

Step 7

4-[4-(4-Methoxyphenyl)sulfonylaminomethylbenzyl]-nitrobenzene (791 mg) was dissolved in ethyl acetate (15 mL) and hydrogenated over 5% palladium on carbon at room temperature. The reaction was allowed to proceed for 6 hours, filtered, and evaporated to dryness. The crude product thus obtained was chromatographed on a short silica column, eluting with hexane/ethyl acetate (1:1), to give 4-[4-(4-methoxyphenyl)sulfonylaminomethylbenzyl]-phenylamine (645 mg, 87%) as a yellow solid.

Last Step

Proceeding as described in Example 1, last Step, but replacing 4-(4-isopropoxybenzyl)-phenylamine with 4-[4-(4-methoxyphenyl)-sulfonylaminomethylbenzyl]-phenylamine (645 mg), concentrating solvents, and chromatography on silica gel, eluting with dichloromethane/methanol/ammonium hydroxide (60:10:1), and recrystalling from acetone with oxalic acid (134 mg, 1 eq), gave 2-{4-[4-(4-methoxyphenyl)sulfonylaminomethylbenzyl]-phenyl}amino-imidazoline oxalate (685 mg, 75%) as a white solid, m.p. 167.0–167.5° C.; Analysis for $C_{26}H_{28}N_4O_7S$: Calc.: C, 57.89; H, 5.11; N, 10.47; Found: C, 57.77; H, 5.22; N, 10.36.

Proceeding as in Example 6, step 6, but replacing 4-methoxybenzenesulfonyl chloride with other sulfonyl chlorides, and then correspondingly in Example 6, subsequent steps, the following compounds of Formula I were prepared:

2-[4-(4-benzenesulfonylaminomethylbenzyl)-phenyl] amino-imidazoline hydrochloride, m.p. 228.2–229.2 0C.;

2-{4-[4-(4-fluorophenyl)sulfonylaminomethylbenzyl]-phenyl}amino-imidazoline oxalate, m.p. 170.0–171.2 0C;

2-{4-[4-(2-fluorophenyl)sulfonylaminomethylbenzyl]-phenyl}amino-imidazoline oxalate, m.p. 94.4–95.6° C.;

2-[4-(4-isopropylsulfonylaminomethylbenzyl)phenyl] amino-imidazoline oxalate, m.p. 128.5–129.5° C.; and 2-[4-(4-propylsulfonylaminomethylbenzyl)phenyl] amino-imidazoline oxalate, m.p. 122.8–123.5° C.

Example 7

2-[4-(4-Ethanesulfonylaminobenzyl)phenyl]amino-imidazoline

The following is an alternative preparation of a compound of Formula I from the corresponding compound of formula Ic' in which $R^1$ is a group represented by formula (A), $R^2$ and $R^4$ are hydrogen, $R^9$ is ethyl, and m is an integer 0.

Step 1

Ethanesulfonyl chloride (1.1 mL, 10 mmol) was added in one portion to a solution of 4,4'-methylenedianiline (1.98 g, 10 mmol) in dichloromethane (25 mL). The reaction mixture was stirred for 1 hour and evaporated to give a solid, which was dissolved in dichloromethane (50 mL) and poured into diethyl ether/2% aqueous potassium carbonate (1:1). After extraction, the aqueous layer was drawn off and discarded.

The organic layer was extracted with 1% aqueous potassium hydroxide (2×100 mL) and the aqueous layer was treated with excess carbon dioxide and extracted with dichloromethane (3×25 mL). The dichloromethane layer was diluted with diethyl ether (125 mL) and extracted with 1% aqueous hydrochloric acid (2×100 mL). The layers were again separated and the aqueous phase was extracted with diethyl ether (50 ml), and the organic phases were discarded. The aqueous phase, which contained the product, was neutralized with solid potassium carbonate, extracted with dichloromethane (4×20 ml), and evaporated to dryness. Recrystallization from acetone/hexanes gave 4-[4-(ethanesulfonyl)aminobenzyl]-phenylamine (940 mg, 32%) as white needles, m.p.108–109° C.

Last Step

Proceeding as described in Example 1, last step, but replacing 4-(4-isopropoxybenzyl)-phenylamine with 4-[4-(ethanesulfonyl)-aminobenzyl]-phenylamine (290 mg, 1 mmol), and crystallization from ethyl acetate, gave 2-[4-(4-ethanesulfonylaminobenzyl)-phenyl]amino-imidazoline (319 mg, 89%).

The hydrochloride salt was obtained by suspending the free base in methanol (10 mL) and adding ethanolic hydrochloric acid until acidic. The solvents were stripped, and product was refluxed with stirring in ethyl acetate (5 mL). The product, 2-[4-(4-ethanesulfonylaminobenzyl)-phenyl] amino-imidazoline hydrochloride was filtered and dried, m.p. 178–178.5° C.; Analysis for $C_{18}H_{23}ClN_4O_2S$: Calc.: C, 54.74; H, 5.87; N, 14.19; Found: C, 54.65; H, 5.79; N, 14.21.

Proceeding as in Example 7, step 1, but replacing ethanesulfonyl chloride with other sulfonyl chlorides, and then correspondingly as in Example 7, subsequent steps, the following compounds of Formula I were prepared:

2-{4-[4-benzenesulfonylaminobenzyl]phenyl}amino-imidazoline hydrochloride, Analysis for $C_{22}H_{23}ClN_4O_2S$: Calc.: C, 57.89; H, 5.41; N, 12.27; Found: C, 57.66; H, 5.17; N, 11.95;

2-{4-[4-(4-methylphenyl)sulfonylaminobenzyl] phenyl}amino-imidazoline hydrochloride, Analysis for $C_{23}H_{25}ClN_4O_2S$: Calc.: C, 59.40; H, 5.61; N, 12.07; Found: C, 59.59; H, 5.64; N, 11.66;

2-[4-(4-isopropylsulfonylaminobenzyl)phenyl]amino-imidazoline hydrochloride, m.p. 206.6–207° C.;

2-[4-(4-methanesulfonylaminobenzyl)phenyl]amino-imidazoline hemioxalate, m.p. 254.2–254.5° C.;

2-[4-(4-benzylsulfonylaminobenzyl)phenyl]amino-imidazoline hydrochloride, Analysis for $C_{23}H_{25}ClN_4O_2S$: Calc.: C, 60.45; H, 5.51; N, 12.26; Found: C, 60.33; H, 5.67; N, 12.39;

2-{4-[4-(2,2,2-trifluoroethyl)sulfonylaminobenzyl] phenyl}amino-imidazoline hydrochloride, Analysis for $C_{18}H_{20}ClF_3N_4O_2S$: Calc.: C, 48.16; H, 4.49; N, 12.48; Found: C, 47.89; H, 4.47; N, 12.33;

2-[4-(4-propylsulfonylaminobenzyl)phenyl]amino-imidazoline hydrochloride, Analysis for $C_{19}H_{25}ClN_4O_2S$: Calc.: C, 55.56; H, 6.18; N, 13.64; Found: C, 55.34; H, 6.17; N, 13.44;

2-[4-(4-butylsulfonylaminobenzyl)phenyl]amino-imidazoline hydrochloride, m.p. 157–160° C.;

2-{4-[4-(4-methoxyphenyl)sulfonylaminobenzyl] phenyl}amino-imidazoline hydrochloride, Analysis for $C_{23}H_{25}ClN_4O_3S$: Calc.: C, 57.96; H, 5.35; N, 11.76; Found: C, 57.81; H, 5.35; N, 11.58;

2-{4-[4-(thien-2-ylsulfonyl)aminobenzyl] phenyl}aminoimidazoline hydrochloride, m.p. 109.5–110° C.; and 2-[4-(4-dimethylaminosulfonylaminobenzyl)phenyl] amino-imidazoline hydrochloride, m.p. 198.5–201° C.

Proceeding as in Example 7, step 1, out replacing ethanesulfonyl chloride with carbonyl chlorides, and then correspondingly as in Example 7, subsequent steps, the following compounds of Formula I were prepared from the corresponding compound of formula Id:

2-{4-[4-(tetrahydropyran-4-ylcarbonyl)aminobenzyl] phenyl}amino-imidazoline, m.p. 225–227° C.; and 2-{4-[4-(isopropylcarbonyl)aminobenzyl] lphenyl}amino-imidazoline hydrochloride, m.p. gum.

Example 8

2-{4-[4-(Ethanesulfonyl)methylaminobenzyl] phenyl}amino-imidazoline

The following is an alternative preparation of a compound of Formula I from the corresponding compound of formula Ic in which $R^1$ is a group represented by formula (A), $R^2$ and $R^4$ are hydrogen, R7 is methyl, $R^9$ is ethyl, and m is an integer 0.

Solid potassium tert-butoxide (113 mg, 1 mmol) was added to a solution of 4-(4-ethanesulfonylaminobenzyl)-phenylamine (290 mg) (prepared as described in Example 7) in dimethyl sulfoxide (2mL). The mixture was stirred and methyl iodide (0.1 mL, 1.5 mmol) was added. After 1 hour, the reaction mixture was poured into water and extracted with diethyl ether (2×). The organic phase was dried on potassium carbonate, evaporated and chromatographed on silica gel, eluting with dichloromethane/acetone, to give 4-[4-(ethanesulfonyl)methylaminobenzyl]-phenylamine (200 mg, 66%) as a yellow solid.

Proceeding as described in Example 1; last step, but replacing 4-(4-isopropoxybenzyl)-phenylamine with 4-[4-(ethanesulfonyl)methylaminobenzyl]-phenylamine (300 mg, 0.99 mmol), refluxing the reaction mixture in isopropanol for 16 hours, and crystallization from ethyl acetate/hexanes gave 2-{4-[4-(ethanesulfonyl)methylaminobenzyl]-phenyl}amino-imidazoline (318 mg, 89%). The free amine was then converted to the hydrochloride salt. m.p. 178–178.5° C.; Analysis for $C_{19}H_{23}ClN_4O_2S$: Calc.: C, 53.68; H, 6.35; N, 13.18; Found: C, 53.72; H, 6.01; N, 13.09.

Proceeding as in Example 8, but replacing methyl iodide with other alkyl iodides, and then correspondingly as in Example 8, the following compounds of Formula I were prepared:

2-{4-[4-(methanesulfonyl)benzylaminobenzyl] phenyl}amino-imidazoline hydrochloride, Analysis for $C_{24}H_{27}ClN_4O_2S$: Calc.: C, 58.08; H, 5.95; N, 10.41; Found: C, 57.97; H, 5.94; N, 10.58;

2-{4-[4-(isopropylsulfonylmethylaminobenzyl] phenyl}amino-imidazoline hydrochloride, Analysis for $C_{20}H27ClN_4O_2S$: Calc.: C, 55.15; H, 6.57; N, 12.86; Found: C, 55.11; H, 6.39; N, 12.76;

2-{4-[4-(propylsulfonyl)methylaminobenzyl] phenyl}amino-imidazoline hydrochloride, Analysis for $C_{20}H_{27}ClN_4O_2S$: Calc.: C, 56.31; H, 6.47; N, 13.13; Found: C, 56.10; H, 6.34; N, 13.04;

2-{4-[4-(ethanesulfonyl)ethylaminobenzyl] phenyl}amino-imidazoline hydrochloride, Analysis for $C_{21}H_{29}ClN_4O_2S$: Calc.: C, 56.55; H, 6.78; N, 12.56; Found: C, 56.51, H, 6.61; N, 12.51; and 2-{4-[4-(ethanesulfonyl)propylaminobenzyl] phenyl}amino-imidazoline hydrochloride, Analysis for $C_{22}H_{31}ClN_4O_2S$: Calc.: C, 54.47; H, 6.62; N, 12.70; Found: C, 54.40, H, 6.44; N, 12.59.

Example 9

2-{4-[4-(1,1-Dioxo-isothiazolidin-1-yl)benzyl]-phenyl}amino-imidazoline

The following is an alternative preparation of a compound of Formula I from the corresponding compound of formula Ic in which $R^1$ is a group represented by formula (A), $R^2$ and $R^4$ are hydrogen, $R^3$ is 1,1-dioxo-isothiazolidin-1-yl.

4-[4-(3-Chloropropyl)sulfonylaminobenzyl]-phenylamine (1.40 g, 3.9 mmol) (prepared as described in Example 7) was stirred in a solution of tetrahydrofuran (25 mL) containing 60% sodium hydride (180 mg, 4.5 mmol). The mixture was refluxed for 16 hours, poured into water, and extracted with dichloromethane (3×). Evaporation and recrystallization gave pure 4-[4-(1,1-dioxo-isothiazolidine)-benzyl]-phenylamine (1.09 g, 86%) as an off-white solid, m.p. 134.5–135.5° C.

Proceeding as described in Example 1, last step, but replacing 4-(4-isopropoxybenzyl)-phenylamine with 4-[4-(1,1-dioxo-isothiazolidin-1-yl)-benzyl]-phenylamine gave 2-{4-[4-(1,1-dioxo-isothiazolidin-1-yl)benzyl]-phenyl}amino-imidazoline; m.p. 197.2–198.5° C.; Analysis for $C_{21}H_{24}N_4O_6S$: Calc.: C, 54.74; H, 5.25; N, 12.17; Found: C, 54.63; H, 5.28; N, 12.11.

Example 10

2-{4-[4-(3-Phenylureido)benzyl]phenyl}amino-imidazoline

The following is an alternative preparation of a compound of Formula I from the corresponding compound of formula Ie in which $R^1$ is a group represented by formula (A), $R^2$, $R^4$, $R^7$ and $R^8$ are hydrogen; $R^9$ is phenyl, V is O, and m is an integer 0.

Step 1

A mixture of 4,4'-methylenedianiline (19.8 g), potassium carbonate (20 g) in ethyl acetate (300 mL) and water (200 mL) was stirred in an ice bath. Benzyl chloroformate (15 mL) was slowly added to the mixture. The resulting mixture was stirred for 1 hour, then the organic layer was separated, and the aqueous layer extracted with additional ethyl acetate. The combined organic extracts were washed with water and brine, dried ($Na_2SO_4$), and the solvent removed in vacuo. The crude mixture was isolated by column chromatography on silica gel, eluting with 30% ethyl acetate/hexanes, to give 4-(4-aminobenzyl)phenyl-carbamic acid benzyl ester as solid.

Step 2

4-(4-Aminobenzyl)phenyl-carbamic acid benzyl ester (0.997, 3 mmol) was added to a solution of phenylisocyanate (0.393 g, 3.3 mmol) in dichloromethane (20 mL). The reaction mixture was stirred for 1 hour at room temperature under nitrogen. The reaction mixture was quenched with water and concentrated in vacuo. The residue was suspended in water, filtered, washed with water, and dried to give {4-[4-(3-phenylureido)benzyl]phenyl}-carbamic acid benzyl ester (1.38 g) as a white solid.

Step 3

A mixture of 4-[4-(3-phenylureido)benzyl]phenyl-carbamic acid benzyl ester (1.3 g) and 10% palladium on carbon (0.35 g) in ethanol (150 mL) was hydrogenated at 50 psi in a Parr apparatus for 12 hours. The reaction mixture filtered through a Celite pad to remove catalyst. The filtrate on concentration gave 4-[4-(3-phenylureido)benzyl]-phenylamine (0.76 g) as white solid.

Last Step

A mixture of 4-[4-(3-phenylureido)benzyl]-phenylamine (0.7 g, 2.21 mmol) and 2-chloro-2-imadazoline sulfate (0.673 g, 3.32 mmol) in 2-propanol (20 mL) was heated under reflux for 1 hour. The reaction mixture was concentrated, diluted with dichloromethane and basified with a 10% sodium hydroxide solution. The organic layer was separated, and the aqueous layer extracted with additional dichloromethane. The combined organic extracts were washed with water and brine, dried ($K_2CO_3$, and the solvent removed in vacuo. The residue was chromatographed on aluminum oxide (neutral, activity I, 15% methanol/dichloromethane) to give 2-{4-[4-(3-phenylureido)benzyl]phenyl}amino-imidazoline as a white solid, m.p. 167–170 0C.; Analysis for $C_{23}H_{23}N_5O$: Calc.: C, 71.70; H. 5.97; N, 18.18; Found: C, 71.34; H, 5.98; N, 17.91.

Proceeding as described in Example 6. step 6, but replacing 4-methoxybenzenesulfonyl chloride with phenylisocyanate, and then correspondingly as in Example 6, gave 2-{4-[4-(3-phenylureido)methylbenzyl]phenyl}-amino-imidazoline fumarate, m.p. 207–208.5° C.

Example 11

2-[4-(4-Dimethylaminosulfonylbenzyl)-phenyl]amino-imidazoline

The following is an alternative preparation of a compound of Formula I from the corresponding compound of formula If in which $R^1$ is a group represented by formula (A), $R^2$ and $R^4$, $R^8$ and $R^9$ are each methyl, and m is an integer 0.

Step 1

A solution of 4-benzyl-nitrobenzene (4.26 g, 70 mmol) dissolved in dichloromethane (25 mL) was added dropwise to a solution of chlorosulfonic acid (6 mL) in dichloromethane (25 mL) at −30° C. The mixture was stirred for 10 minutes at 0° C., then poured onto ice and shaken. The organic phase was separated and solvents were evaporated. The residue was recrystallized from dichloromethane/hexanes to yield 4-(4-chlorosulfonylbenzyl)-nitrobenzene (5.52 g, 78%) as dichloromethane hemisolvate crystals.

Step 2

A solution of dimethylamine in tetrahydrofuran (2M, excess) was added 4-(4-chlorosulfonylbenzyl)-nitrobenzene dichloromethane hemisolvate (354 mg, 1 mmol) dissolved in tetrahydrofuran (5 mL). The mixture was stirred for 1 hour and extracted with a solution of diethyl ether and dilute potassium carbonate. The organic layer was separated and solvents evaporated. The residue was recrystallized from acetone/hexanes to give 4-(4-dimethylaminosulfonylbenzyl)-nitrobenzene (311 mg, 98%).

Step 3

4-(4-Dimethylaminosulfonylbenzyl)-nitrobenzene (311 mg) was dissolved in ethyl acetate and hydrogenated at 40 psi using a 10% palladium on carbon catalyst for 2 hours. The mixture was filtered, and solvents evaporated to give 4-(4-dimethylaminosulfonylbenzyl)-phenylamine as a white solid (288 mg, 99%).

Last Step

A mixture of 4-(4-dimethylaminosulfonylbenzyl)-phenylamine (288 mg) and 2-chloro-imidazoline sulfate (110 mg) in 2-propanol was heated under reflux for 1 hours. A dilute solution of potassium carbonate was poured into the mixture and extracted with dichloromethane (4×15 mL). Solvents were evaporated to give 2-[4-(4-dimethylaminosulfonylbenzyl)-phenyl]amino-imidazoline as a solid (320 mg).

The product was dissolved in ethyl acetate and treated with excess methanolic hydrogen chloride to give a crude product. Solvents were evaporated and the residue was recrystallizated from 2-propanol/ethyl acetate to give 2-[4-(4-dimethylaminosulfonylbenzyl)-phenyl]amino-imidazoline hydrochloride as a white solid (292 mg, 76%), m.p. 194.1–195.3° C.; Analysis for $C_{18}H_{23}ClN_4O_2S$: Calc.: C, 54.99; H, 5.87; N, 14.19; Found: C, 54.74; H, 5.87; N, 13.96.

Proceeding as described in Example 11, step 2, but replacing dimethylamine with other amines, and then correspondingly as in Example 11, subsequent steps, other compounds of Formula I were prepared:

2-[4-(4-benzylaminosulfonylbenzyl)-phenyl]amino-imidazoline hydrochloride, m.p. glass; Analysis for $C_{23}H_{23}ClN_4O_2S.0.7H_2O$: Calc.: C, 59.04; H, 5.45; N, 11.97; Found: C, 59.05; H, 5.42; N, 11.90;

2-[4-(4-isobutylaminosulfonylbenzyl)-phenyl]amino-imidazoline hydrochloride, m.p. glass; Analysis for $C_{20}H_{27}ClN_4O_2S.0.7H_2O$: Calc.: C, 55.36; H, 6.34; N, 12.91; Found: C, 55.38; H, 6.21; N, 12.66;

2-[4-(4-pyrrolidin-1-ylsulfonylbenzyl)-phenyl]amino-imidazoline hydrochloride, m.p. 190.0–191.2° C.; Analysis for $C_{20}H_{25}ClN_4O_2S$: Calc.: C, 57.06; H, 5.99; N, 13.31; Found: C, 56.97; H, 5.93; N, 13.15;

2-[4-(4-isopropylaminosulfonylbenzyl)-phenyl]amino-imidazoline oxalate, m.p. 138.0–140.5° C.; Analysis for $C_{21}H_{26}N_4O_6S$: Calc.: C, 54.53; H, 5.67; N, 12.1; Found: C, 54.39; H, 5.58; N, 12.02;

2-[4-(4-diisopropylaminosulfonylbenzyl)-phenyl]amino-imidazoline hydrochloride, m.p. glass; Analysis for $C_{22}H_{31}ClN_4O_2S.0.5H_2O$: Calc.: C, 57.57; H, 6.81; N. 12.20; Found: C, 57.67; H, 6.85; N, 11.81;

2-[4-(4-t-butylaminosulfonylbenzyl)-phenyl]amino-imidazoline oxalate, m p. glass, Analysis for $C_{22}H_{28}N_4O_6S.H_2O$: Calc.: C, 53.43; H, 6.11; N, 1.33; Found: C, 53.67; H, 53.67; N, 11.03; and 2-[4-(4-butylaminosulfonylbenzyl)-phenyl]amino-imidazoline oxalate, m.p. 153.6–154.4° C., Analysis for $C_{22}H_{28}N_4O_6S$: Calc.: C, 55.45; H, 5.92; N, 11.76; Found: C, 55.23; H, 5.80; N, 11.67.

Example 12

2-[4-(4-Benzylaminosulfonylmethylbenzyl)-phenyl]amino-imidazoline

The following is an alternative preparation of a compound of Formula I from the corresponding compound of formula If in which $R^1$ is a group represented by formula (A), $R^2$, $R^4$ and $R^8$ are hydrogen, $R^9$ is benzyl, and m is an integer 1.

Alternative Step 1a

A solution of sodium sulfite (0.73 g, 7 mmol) dissolved in water (10 mL) was added to a solution of 4-(4-bromomethylbenzyl)-nitrobenzene (1.41 g, 5.6 mmol) in acetonitrile (10 mL). The mixture was stirred and heated under reflux for 2 hours. Solvents were evaporated and dried to give the 4-(4-nitrobenzyl)-phenylmethanesulfonic acid sodium salt as a white powder (2.29 g).

Alternative Step 1b 4-(4-Nitrobenzyl)-phenylmethanesulfonic acid sodium salt (2.29 g) was combined with phosphorus pentachloride (1.45 g). The mixture was heated to 90° C. for 5 minutes, poured into water, and extracted with dichloromethane (3×20 mL). Solvents were evaporated to give 4-(4-chlorosulfonylmethylbenzyl)-nitrobenzene as an impure yellow solid (0.63 g). This product was used directly in the next step.

Step 2

Benzylamine (0.3 mL) was added to a solution of 4-(4-chlorosulfonylmethyl-benzyl)-nitrobenzene (100 mg) in tetrahydrofuran (4 mL). The mixture was stirred for 2 hours, poured into dilute aqueous potassium carbonate, and extracted with dichloromethane (3×15 mL). Solvents were evaporated and the residue was chromatographed on silica gel, eluting with 2% acetone in dichloromethane, to give 4-(4-benzylaminosulfonylmethylbenzyl)-nitrobenzene (44 mg) as a solid.

Step 3

A solution of 4-(4-benzylaminosulfonylmethylbenzyl)-nitrobenzene (44 mg) was dissolved in ethyl acetate and hydrogenated at 40 psi with 10% palladium or carbon catalyst for 2 hours. The mixture was filtered, and the solvent was evaporated to give 4-(4-benzylaminosulfonylmethylbenzyl)-phenylamine (39 mg) as an off-white solid.

Last Step

A mixture of 4-(4-benzylaminosulfonylmethylbenzyl)-phenylamine (39 mg) and 2-chloro-imidazoline base (1 ea) in 2-propanol was heated under reflux for 16 hours. A dilute solution of potassium carbonate was poured into the mixture and extracted with dichloromethane (4×15 mL). Solvents were evaporated to give 2-[4-(4-benzylaminosulfonylmethylbenzyl)-phenyl]amino-imidazoline as a solid (41.7 mg), m.p. 115–118° C.; Analysis for $C_{24}H_{25}ClN_4O_2S \cdot H_2O$: Calc.: C, 58.94; H, 5.98; N, 11.46; Found: C, 59.01; H, 5.91; N, 11.30.

Proceeding as described in Example 12, step 2, but replacing benzylamine with other amines, and then correspondingly as in Example 12, subsequent steps, other compounds of Formula I were prepared:

2-[4-(4-isobutylaminosulfonylmethylbenzyl)-phenyl]amino-imidazoline hydrochloride as a solid (51.5 mg), m.p. 113.2–114.6° C.; Analysis for $C_{21}H_{29}ClN_4O_2S \cdot 0.5H_2O$: Calc.: 56.55; H, 6.78; N, 12.56; Found: C, 56.68; H. 6.67; N, 12.40;

2-[4-(4-dimethylaminosulfonylmethylbenzyl)-phenyl]amino-imidazoline oxalate (73 mg, 58%), m.p. 154.4–154.8° C.; Analysis for $C_{23}H_{28}N_4O_6S$: Calc.: C, 56.54; H, 5.78; N, 11.42; Found: C, 56.56; H, 5.67; N, 11.46; and 2-[4-(4-pyrrolidin-1-ylsulfonylmethylbenzyl)-phenyl]amino-imidazoline oxalate (105 mg, 3%), m.p. 160–161° C.; Analysis for $C_{21}H_{26}N_4O_6S$: Calc.: C, 54.53; H, 5.67; N, 12.11; Found: C, 54.48; H, 5.58; N, 12.13.

Example 13

2-[4-(4-Pyrrolidin-1-ylaminocarbonylbenzyl)-phenyl]amino-imidazoline

The following is an alternative the preparation of a compound of Formula I from the corresponding compound of formula Ig in which $R^1$ is a group represented by formula (A), $R^2$ and $R^4$ are hydrogen, $R^8$ and $R^9$ taken together with the nitrogen to which they are attached form pyrrolidine, and m is an integer 0.

Step 1

10% Palladium on carbon (0.5 g) was added to a solution of 4-benzoyl-benzoic acid (11.31 g, 50 mol) in ethanol (250 mL) and 70% perchloric acid (10 mL). The suspension was hydrogenated under 40 psi at room temperature for 8 hours. The catalyst was removed by filtration and the filtrate made neutral with aqueous sodium bicarbonate. Solvents were evaporated, and the residue was partitioned into ethyl acetate and dilute aqueous potassium hydroxide. The aqueous phase was acidified with hydrochloric acid. The precipitated acid was filtered, washed, and dried to give 4-benzyl-benzoic acid (10.74 g, ~100%).

Step 2

4-(4-Nitrobenzyl)-benzoic acid was prepared utilizing the procedures described in Coon et al. *J. Org. Chem.* 1973, 38, 4243.

70% Nitric acid (3.16 mL) was added dropwise to a suspension of trifluoromethanesulfonic acid (9.34 mL, 105.6 mmol) in dichloromethane (250 mL). The suspension was cooled in a dry ice-acetone bath and a solution of 4-benzyl-benzoic acid (10.19 g, 48 mmol) in dichloromethane (50 mL) was added dropwise. The mixture was stirred for about 2 hours at −78° C. and an additional 2 hours at room temperature. The reaction mixture was poured into crushed ice. The separated organic layer was washed with dichloromethane (2×) and the combined organic layers were dried over ($Na_2SO_4$), and solvents were evaporated. Recrystallization of the crude product from methanol/ethyl acetate gave 4-(4-nitrobenzyl)-benzoic acid (9.27 g, 58%) as a yellow solid.

Step 3

4-(4-Nitrobenzyl)-benzoic acid (1.03 g, 4 mmol) was dissolved in dichloromethane (40 mL). Oxalyl chloride (0.42 mL, 1.2 eq) was added to the mixture, followed by 1 drop of N,N-dimethylformamide. The mixture was stirred for 1 hour at room temperature and the solvents evaporated to give 4-(4-chlorocarbonylbenzyl)-nitrobenzene (1.10 9) as a pale yellow solid.

Step 4

4-(4-Chlorocarbonylbenzyl)-nitrobenzene was dissolved in dichloromethane (40 mL) and a solution of pyrrolidine (64 mg, 1 eq) in pyridine (0.2 mL) was added. The mixture was stirred for 2 hours at room temperature, washed with dilute potassium hydroxide, and solvents evaporated to yield a yellow oil. The residue was chromatographed on silica gel, eluting with dichloromethane/methanol, to give 4-(4-pyrrolidin-1-ylcarbonyltenzyl)-nitrobenzene (299 mg, 99%).

Step 5

A mixture of 4-(4-pyrrolidin-1-ylcarbonylbenzyl)-nitrobenzene (202 mg, 065 mmol), 10% palladium on carbon (110 mg), and ethanol (20 mL) was hydrogenated at 40 psi for 16 hours. The mixture was filtered through a Celite pad, and solvents evaporated to give 4-[4-(1-pyrrolidinecarbonyl)benzyl]-phenylamine as a white solid (187 mg, 99%).

Last Step

A mixture of 4-[4-(1-pyrrolidinecarbonyl)benzyl]-phenylamine (182 mg, 0.64 mmol) and 2-chloro-2-imidazoline bisulfate (131 mg, 1 eq) in 2-propanol (30 mL) was stirred at 60° C. for 60 hours. The solvents were evaporated, and the residue suspended in dilute potassium hydroxide. The suspension was extracted with dichloromethane and chromatographed on silica gel, eluting with methanol/ammonium hydroxide, to give a white solid (205 mg). The white solid was extracted with ethyl acetate, washed with dilute potassium hydroxide, and treated with excess hydrochloric acid in diethyl ether to give 2-{4[4-(1- pyrrolidinecarbonyl)benzyl]-phenyl}amino-imidazoline hydrochloride (193 mg, 77%), m.p. shrinks at 46° C.; Analysis for $C_{21}H_{25}ClN_4O.0.7H_2O$: Calc.: C, 63.71; H, 6.69; N, 14.09; Found: C, 63.44; H, 6.38; N, 13.81.

Proceeding as described in Example 13, step 4, but replacing pyrrolidine with other amines, and then correspondingly as in Example 13, subsequent steps, other compounds of Formula I were prepared:

2-[4-(4-isobutylaminocarbonylbenzyl)-phenyl]amino-imidazoline oxalate, m.p. 100–144° C.; Analysis for $C_{23}H_{28}N_4O$: Calc.: C, 62.71; H, 6.41; N, 12.72; Found: C, 62.44; H, 6.36; N, 12.72; and 2-[4-(4-benzylaminocarbonylbenzyl)-phenyl]amino-imidazoline oxalate, m.p. 188.5–195.0° C.; Analysis for $C_{24}H_{24}N_4O.0.85C_2H_2O_4$: Calc.: C, 66.95; H, 5.62; N, 12.15; Found: C, 67.05; H, 5.55; N, 12.26.

Example 14

2-[4-(4-Cyclopentyloxythien-2-ylmethyl)phenyl]amino-imidazoline

The following is a preparation of a compound of Formula I from the corresponding compound of formula Ih in which $R^1$ is a group represented by formula (B) where X is S, $R^2$ is hydrogen, Y is cyclopentyl, and m is an integer 0.

Step 1

To a solution of cyclocentanol (8.75 ml, 95.8 mmol) in N,N-dimethylformamide (250 mL) was added sodium hydride (60% dispersion in mineral oil, 3.84 g, 95.8 mmol) at 0–5° C. under nitrogen. After 10 minutes, the mixture was allowed to reach room temperature and stirred for 40 minutes. 3-Bromothiophene (3.59 mL, 38.3 mmol) was added followed by cuprous iodide (14.63 g, 76.8 mmol). The mixture was heated at 120° C. for 22 hours. After cooling to about 10° C., a solution of sodium cyanide (12.1 g, 0.25 mol) in water (200 mL) was added under vigorous stirring. The mixture was stirred for additional 10 minutes then filtered. The filtrate was extracted with hexane. The extract was washed with water, dried ($Na_2SO_4$) and concentrated to dryness. Distillation (100° C., 8 mm Hg) gave 3-cyclopentyloxythiopene (4.52 g, 70%) as a slightly pale yellow oil; $^1$H NMR (300 Mz, $CDCl_3$) δ 7.15 (dd, J=5.2, 3.1 Hz, 1H), 6.72 (dd, J=5.2, 15 Hz, 1H) 6.19 (dd, J=3.1, 1.5 Hz, 1H), 4.65 (quintet, J=4.2 Hz), 1H), 1.55–1.95 (m, 8H). MS m/e (%): 168 (M+; 17).

Step 2

2-Chloro-3-cyclopentyloxythiophene was prepared according to the procedures described in P. Stanetty and E. Puschautz, *Monatshefte Chemie*, 1989, 120, 65. Thus, to a solution of 3-cyclopentyloxythiophene (3.98 g, 23.7 mmol) in dichloromethane (35 mL) was added sulfuryl chloride (2 mL, 24.9 mmol) at 15° C. under argon. The mixture was stirred for 1 hour, then concentrated to dryness. Purification by flash chromatography (silica, 100% hexane) gave 2-chloro-3-cyclopentyloxythiophene (2.75 g, 59%) as a pale yellow oil; $^1$HNMR 300 MHz, $CDCl_3$) δ 6.99 (d, J=6.0 Hz, 1 H), 6.75 (d,J=6.0 Hz, 1 H), 4.69–4.74 (m, 1H), 1.7–1.93 (m, 6H), 1.5–1.7 (m,2H). MS m/e (%): 202 (M+; 6).

Step 3

To a solution of 2-chloro-3-cyclopentyloxythiophene (2.15 g, 10.6 mmol) in ether (27 mL) was added n-butyllithium (2.5 N in hexanes, 4.4 mL, 11 mmol) dropwise at −78° C. under argon. The mixture was allowed to reach 20–25° C. and stirred for 4 hours. After cooling back to −78° C., a solution of p-nitrobenzaldehyde (1.56 g, 10.3 mmol) in tetrahydrofuran (27 mL) was added dropwise. The mixture was stirred at −78° C. for 1 hour. Saturated ammonium chloride was added at −78° C. and the mixture was allowed to reach about 10° C. The crude product was extracted with ethyl acetate, washed with water, brine, dried ($Na_2SO_4$), and concentrated to dryness to give 4-(5-chloro-4-cyclopentyloxythien-2-yl)-(4-nitrophenyl)methanol (3.6 g), and was directly used in the next step.

Step 4

4-(Cyclopentyloxythien-2-ylmethyl)-nitrobenzene may be prepared by methods described in E. J Stoner et al., *Tetrahedron*, 1995, 51, 11043. Thus, to a suspension of sodium iodide (6.64 g, 44.3 mmol) in acetonitrile (10 mL) was added trimethylsilyl chloride (5.6 mL, 44.3 mmol) at 20–25° C. under argon. After stirring for 15 minutes at 20–25° C., the mixture, was cooled to 0–5° C. and a solution of crude 4-(5-chloro-4-cyclopentyloxythien-2-yl)-(4-nitrophenyl)methanol (3.6 g) in acetonitrile (10 mL) was slowly added. Aqueous sodium hydroxide (10%, 11.5 mL) was added followed by excess water. The product was extracted with ethyl acetate, washed with a solution of sodium thiosulfate (4.83 g) in water (10 mL), water, brine, dried ($Na_2SO_4$), and concentrated to dryness. Purification by flash chromatography (silica, 98.5:1.5 hexane/ethylacetate)-gave 4-(4-cyclopentyloxythien-2-ylmethyl)-nitrobenzene (1.25 g, 40%) as a pale yellow oil; $^1$HNMR (300 MHZ, $CDCl_3$) δ 11.97 (d,J=8.8, 2H), 7.40 (d,J=8.8Hz, 2H), 6.45 (m, 1 H), 6.03 (d, J=1.7, 1H), 4.60 (quintet, J=4.3Hz, 1H), 4.13 (S, 2H), 1.5–1.89 (m, 8H). MS m/e (%): 303 (M+; 15).

Step 5

To a solution of 4-(4-cyclopentyloxythien-2-ylmethyl)-nitrobenzene (1.28 g, 4.2 mmol) in absolute ethanol (34 mL) was added tin dichloride hydrate (4.76 9, 21.2 mmol) at 20–25° C. under nitrogen. The mixture was heated at 75° C. for 2.5 hours and cooled to 0–5° C. Saturated sodium bicarbonate was added to pH 8. Ethyl acetate was added and the mixture was filtered. The layers were separated, and the aqueous phase was extracted with additional ethyl acetate. The combined organic phases were washed with brine, dried ($Na_2SO_4$), and concentrated to dryness. Purification by flash chromatography (silica, hexane/ethylacetate) gave 4-(4-cyclopentyloxythien-2-ylmethyl)-phenylamine (0.47 g, 41%) as a pale yellow oil; $^1$H NMR (300 MHz, $CDCl_3$) δ 7.03 (d, J=8.5Hz, 2H), 6.63 (d, J=8.5Hz 2H), 6.41 (m, 1 H), 5.96 (d, J=1.7Hz, 1H, 4.58 (quintet, J=4.3 Hz, 1H), 3.91 (S, 2H), 3.59 (bs, 2H), 1.67–1.88 (m, 6H), 1.46–1.67 (m, 2N).

Last Step

To a solution of 4-(4-cyclopentyloxythien-2-ylmethyl)-phenylamine (463 mg, 1.69 mmol) in isopropyl alcohol (7 ml) was added a solution of 2-chloro-2-imidazoline (293 mg, 2.8 mmol) in isopropyl alcohol (7 ml). The mixture was heated at reflux overnight, and the isopropyl alcohol was removed in vacuo. 10% Sodium hydroxide was added, and the product was extracted with dichloromethane. The extract was washed with water, dried ($Na_2SO_4$) and concentrated to dryness to give a crude product.

The crude product (578 mg) was dissolved in toluene (90 mL), and followed by the addition of cyclopentanol (4 mL) and p-toluenesulfonic acid hydrate (674 mg). The mixture was heated at 100–110° C. for 2 hours and cooled to room temperature. 10% Sodium hydroxide was added. The final product was extracted with dichloromethane (3×), washed with water, dried ($Na_2SO_4$), and concentrated to dryness. Purification by preparative TLC, eluting with ethyl acetate/methyl alcohol/isopropyl amine, gave 2-[4-(4-cyclopentyloxythien-2-ylmethyl)phenyl]amino-imidazoline (290 mg, 50%) as a pale yellow oil; $^1$H NMR δ 300 MHz, CDCl$_3$) δ 7.13 (d, J=8.2 Hz 2H), 6.93 (d, J=8.2 Hz 2H), 6.42 (m, 1H), 5.97 (d, J=1.7 Hz, 1H), 4.59 (quintet, J=4.3 Hz, 1H), 3.96 (S, 2H), 3.8–4.1 (broad, 2H), 3.52 (S, 4H), 1.67–1.89 (m, 6H), 1.51–1.66 (m, 2H).

2-[4-(4-cyclopentyloxythien-2-ylmethyl)phenyl]amino-imidazoline oxalate, m.p. 142.4–143.3° C.

Proceeding as in Example 14, step 1, but replacing cyclopentanol with isopropanol, and then correspondingly as in Example 14, subsequent steps, gave 2-[4-(4-isopropoxythien-2-ylmethyl)phenyl]amino-imidazoline oxalate, m.p. 151.3–151.8° C.

Example 15

2-[4-(5-Methoxythien-2-ylmethyl)phenyl]amino-imidazoline

The following is an alternative preparation of a compound of Formula I from the corresponding compound of formula Ii in which R$^1$ is a group represented by formula (B) where X is S, R$^2$ is hydrogen, Y is methyl, and m is an integer 0.

Step 1

2-Methoxythiophene was prepared by the procedures described in H. A. Keeystra et al., *Tetrahedron*, 1992, 48, 3633. Thus, a solution of sodium methoxide in methanol was prepared by adding sodium (2.12 g, 92.2 mmol) to methanol (14 ml). 2-bromothiophene (10 g, 61.3 mmol) was added while maintaining reflux. Cuprous bromide (0.88 g, 6.1 mmol) was added and the mixture was maintained at reflux for 5.5 hours. A solution of sodium cyanide (3 g, 61.3 mmol) in water (30 ml) was added at 20–25° C. under vigorous stirring. The mixture was stirred until all solids dissolved, extracted with hexane, dried (Na$_2$SO$_4$), and concentrated to dryness. Distillation (90° C., 80 mm Hg) gave 2-methoxythiophene (5.35 g, 76%) as a colorless oil.

Step 2

5-Methoxythien-2-yl-(tri-n-butyl)stannane was prepared by the addition n-butyllithium (1.98 M in hexanes, 3.81 mL, 7.54 mmol) to a solution of 2-methoxythiophene (860 mg, 7.54 mmol) in tetrahydrofuran (4.3 mL) at −78° C. under argon. The mixture was allowed to reach 0–5° C. and stirred for 2 hours, re-cooled to −78° CC and tributyltin chloride (2.05 ml, 7.54 mmol) was added. The mixture was allowed to reach 0–5° C. and stirred for 1 hour. The product, 5-methoxythien-2-yl-(tri-n-butyl)stannane, was directly used in the next step.

Step 3

5-Methoxythien-2-yl-(tri-n-butyl)stannane was added to 4-chloromethylphenyl-carbamic acid 2-trimethylsilanyl ethyl ester (2.15 g, 7.54 mmol) (described in Preparation 2) at 20–25 ° C. followed by hexamethylphosphoramide (11 mL) and tetrakis(triphenylphosphine)-palladium (174.2 mg, 0.146 mmol). The mixture was heated at 65° C. for 4.5 hours. Water was added and product extracted with ether. The extract was washed with water, dried (Na$_2$SO$_4$), and concentrated to dryness. The residue was dissolved in acetonitrile and washed twice with hexane. The acetonitrile phase was concentrated to dryness, and purification by flash chromatography on silica, eluting with hexane/ethyl acetate, gave [4-(5-methoxythien-2-ylmethyl)phenyl]-carbamic acid 2-trimethylsilanyl ethyl ester (690 mg, 25%) as a yellow liquid; $^1$H NMR (300 MHz, CDCl$_3$) δ 7.25 (d, J=8.5 Hz 2H), 7.16 (d, J=8.5 Hz 2H), 6.49 (bs, 1H), 6.37 (dt, J=3.7, 1.0 Hz, 1H), 5.98 (d, J=3.7, 1.1H), 4.25 (m, 2H), 3.94 (bs, 2H), 3.82 (s, 3H), 1.04 (m, 2H), 0 06 (s, 9H).

Step 4

To a solution of [4-(5-methoxythien-2-ylmethyl)phenyl]-carbamic acid 2-trimethylsilanyl ethyl ester (684 mg, 1.88 mmol) in dimethyl sulfoxide (24 mL) was added tetra-n-butylammonium fluoride (1 M in tetrahydrofuran, 5.6 mL) at 20–25° C. under argon. The mixture was stirred for 1 hour. Ether was added and the solution was washed with water, brine, dried (Na$_2$SO$_4$), and concentrated to dryness. Purification by flash chromatography on silica, eluting with hexane/ethyl acetate, gave 4-(5-methoxythien-2-ylmethyl)-phenylamine (372 mg, 90%) as a thick yellow oil; $^1$H NMR (300 MHz, CDCl$_3$) δ 7.02 (d,J=8.5 Hz, 2H), 6.63 (d, J=8.5 Hz, 2H), 6.36 (dt, J=3.7, 1.1 Hz, 1H), 5.97 (d, J=3.7 Hz, 1H), 3.87 (bs, 2H), 3.81 (5, 3H), 3.4–3.7 (broad, 1H). MS m/e (%): 219 (M+;100).

Last Step

To a solution of [4-(5-methoxythien-2-ylmethyl)-phenylamine (145 mg, 0.66 mmol) in acetonitrile (10 ml) was added 2-chloro-2-imidazoline sulfate (155 mg, 0.76 mmol) at 20–25° C. under nitrogen. The resulting suspension was heated at 80° C. for 1.5 hours. The mixture was diluted with dichloromethane and washed with 10% sodium hydroxide, water, dried (Na$_2$SO$_4$), and concentrated to dryness. Purification by preparative TLC, eluting with ethyl acetate/methyl alcohol/isopropylamine, gave 2-[4-(5-methoxythien-2-ylmethyl)phenyl]amino-imidazoline (132 mg, 70%) as a yellow oil; $^1$H NMR (300 MHz, CDCl$_3$) δ 7.12 (d, J=8.4 Hz, 2H), 6.93 (d, J=8.4 Hz, 2H), 6.39 (dt, J=3.7, 1.1 Hz, 1H), 5.98 (d, J=3.7 Hz, 1H), 3.92 (bs, 2H), 3.82 (S, 3H), 3.52 (S , 4H), 3.15–3.35 (broad, 2H).

2-[4-(5-methoxythien-2-ylmethyl)phenyl]amino-imidazoline oxalate, m.p. 121.8–122.8° C.

Example 16

2-[4-(5-Cyclopentyloxythien-2-ylmethyl)phenyl] amino-imidazoline

The following is an alternative preparation of a compound of Formula I from the corresponding compound of formula Ii in which R$^1$ is a group represented by formula (B) where X is S, R$^2$ is hydrogen, Y is cyclopentyl, and m is an integer 0.

To a mixture of cyclopentanol (51.1 ml, 0.56 mol) and dioxane (50 mL) was added sodium hydride (60% in mineral oil, 4.91 g, 0.12 mol) at 0–5° C. under argon. The mixture was heated at 80° C. until an homogenous solution was observed. 2-Bromothiophene (10 g, 5.9 mL, 0.061 mol) was added at 80° C., followed by cuprous iodide (11.7 g, 0.061 mol). The. mixture was heated at 120° C. for 6 hours. After cooling to 20–25° C., sodium cyanide (30 g, 0.61 mol) in water (200 mL) was added. The mixture was vigorously stirred for 20 minutes, filtered, and extracted with hexane. The hexane extract was washed with water, dried (Na$_2$SO$_4$), and concentrated to dryness. Filtration through a column (silica, 100% hexane) gave 2-cyclopentyloxythiophene (2.6 g, 25.2%) as a colorless oil; $^1$HNMR (300 MHz, CDCl$_3$) δ 6.7 (dd, J=5.7, 3.7 Hz, 1 H), 6.54 (dd, J=5.7, 1.5 Hz, 1H), /86.18 (dd, J=3.7, 1.5 Hz), 4.66 (Sept, J=2.7 Hz, 1H), 1.5–2.0 (m, 8H).

Proceeding as described in Example 15, step 2, but replacing 2-methoxythiophene with 2-cyclopentyloxythiophene, and then correspondingly as in Example 15, subsequent steps gave 2-[4-(5-cyclopentyloxythien-2-ylmethyl)phenyl]amino-imidazoline oxalate, m.p. 71.2–75.5° C.

Example 17

2-[4-(5-Isopropoxythien-2-ylmethyl)phenyl]amino-imidazoline

The following is an alternative preparation of a compound of Formula I from the corresponding compound of formula Ii in which $R^1$ is a group represented by formula (B) where X is S, $R^2$ is hydrogen, Y is isopropyl, and m is an integer 0.

To a solution of 4-(5-methoxythien-2-ylmethyl)-phenylamine (210 mg, 0.96 mmol) in isopropyl alcohol (20 ml) was added p-toluenesulfonic acid hydrate (460 mg, 2.4 mmol) under nitrogen. The mixture was heated at reflux for 24 hours and cooled to 20–25° C. 5% Sodium hydroxide was added, and the product was, extracted with dichloromethane. The extract was dried ($Na_2SO_4$), and concentrated to dryness. Purification by preparative TLC, eluting with hexane/ethyl acetate, gave 4-(5-isopropoxythien-2-ylmethyl)-phenylamine (135 mg, 57%) as a pale yellow oil; $^1$HNMR (300 MHz, $CDCl_3$) δ 7.02 (d, J=8.5 Hz, 2H), 6.63 (d, J=8.5 Hz, 2H), 6.34 (dt, J=3.7, 1.1 Hz, 1H), 6.01 (d, J=3.7, 1H), 4.26 (quintet, J=6.1 Hz, 1H), 3.88 (bs, 2H), 1.31 (d, J=6.1 Hz, 6H). MS m/e (%): 247 (M+; 58).

Last Step

To a solution of 4-(5-isopropoxythien-2-ylmethyl)-phenylamine (131 mg, 0.53 mmol) in aceonitrile (8 ml) was added 2-chloro-2-imidazoline sulfate (121 mg, 0.59 mmol) at 20–25° C. under argon. The mixture was heated at 80° C. for 1.5 hours. The mixture was diluted with dichloromethane and washed with sodium hydroxide, water, dried ($Na_2SO_4$) and concentrated to dryness. Purification by preparative TLC, eluting with ethyl acetate/methyl alcohol/isopropylamine, gave 2-[4-(5-isopropoxythien-2-ylmethyl)phenyl]amino-imidazoline (150 mg, 90%) as a thick yellow oil; $^1$H NMR (300 Mhz, $CDCl_3$ δ 7.13 (d, J=8.4 Hz, 2H) 6.93 (d, J=8.4 Hz, 2H), 6.37 (dt, J=3.7, 1.0 Hz, 1H), 6.02 (d, J=3.7 Hz, 1H), 4.28 (quintet, J=6.2 Hz, 1H), 3.93 (bs, 2H), 3.52 (5, 4H), 3.24–3.5 (broad, 2H), 1.32 (d, J=6.2 Hz, 6H), MS m/e (%):316 (M+1, 100%).

2-[4-, 3-isopropoxythien-2-ylmethyl)phenyl]amino-imidazoline oxalate, m.p. 134.4–135° C.

Example 18

2-[4-(1-Isopropylaminocarbonylpiperidin-4-ylmethyl)-phenyl]amino-imidazoline

The following is a preparation of a compound of Formula I from the corresponding compound of formula Ij in which $R^1$ is a group represented by formula (C) where X is N, $R^2$, $R^4$, and $R^8$ are hydrogen, $R^9$ is isopropyl, V is O, and m is an integer 0.

Step 1

A mixture of 4-(4-nitrobenzyl)pyridine (12.85 g, 60 mmol), platinum(IV) oxide (1.0 g), 12N hydrochloric acid (5 ml, 60 mmol), water (5 ml) in ethanol (200 ml) was hydrogenated at 40 psi in a Parr apparatus for 12 hours. The reaction mixture was concentrated in vacuo, and the residue was diluted with cold water and basified with 10% sodium hydroxide solution. The resulting mixture was extracted into ethyl acetate. The combined organic extracts were washed with water and brine, dried ($Na_2SO_4$), and concentrated in vacuo. The residue on crystallization from ethyl acetate/hexanes gave 4-(piperidin-4-ylmethyl)-phenylamine (9.85 g, 86%) as a white crystalline solid, m.p. 110–113° C.

Step 2

A solution of 4-(piperidin-4-ylmethyl)-phenylamine (0.57 g, 3 mmol) in dichloromethane (20 mL) was cooled in an ice bath under nitrogen atmosphere. Isopropyl isocyanate (0.28 g, 3.3 mmol) was added dropwise to the solution and stirred at ice bath temperature for 30 minutes. The reaction mixture was quenched with water and extracted with dichloromethane. The combined organic extracts were washed with water and brine, dried, and solvents removed in vacuo. The crude product was chromatographed on silica gel, eluting with 2% methanol/dichloromethane containing 0.01% ammonium hydroxide, to give 4-(1-isopropylaminocarbonylpiperidin-4-ylmethyl)-phenylamine (0.66 g, 80%) as a gum.

Last Step

A mixture of 4-(1-isopropylaminocarbonylpiperidin-4-ylmethyl)-phenylamine (0.64 g, 2.31 mmol) and 2-chloro-2-imidazoline sulfate (0.70 g, 3.47 mmol) in 2-propanol (20 mL) was heated under reflux for 30 minutes. The reaction mixture was concentrated in vacuo. The residue was diluted with water, basified with 10% sodium hydroxide solution and extracted into dichloromethane. The organic layer was washed with water and brine, dried ($Na_2SO_4$), and concentrated in vacuo. The crude product was chromatographed on neutral aluminum oxide, eluting with 5% methanol/dichloromethane, and crystallized from ethyl acetate containing some ethanol, to give 2-[4-(1-isopropylaminocarbonylpiperidin-4-ylmethyl)-phenyl]amino-imidazoline (0.47 g, 59%) as a white solid, m.p. 191–192° C.

Proceeding as described in Example 18, step 1, and proceeding directly to the last step, gave 2-[4-(piperidin-4-ylmethyl)phenyl]amino-imidazoline hydrochloride as a foam.

Proceeding as described in Example 18, step 2, but replacing isopropyl isocyanate with other isocyanates, and then correspondingly as in Example 15, last step, other compounds of Formula I were prepared:

2-[4-(1-phenylaminocarbonylpiperidin-4-ylmethyl) phenyl]amino-imidazoline hydrochloride, m.p. shrinks at 99° C. (highly hygroscopic), $C_{22}H_{28}N_5OCl$; and 2-[4-(1-ethylaminocarbonylpiperidin-4-ylmethyl)phenyl] amino-imidazoline hydrochloride, m.p. shrinks at 97° C. (very hygroscopic), $C_{18}H_{28}N_5OCl$.

Example 19

2-[4-(1-Benzenesulfonylpiperidin-4-ylmethyl)-phenyl]amino-imidazoline

The following is an alternative preparation of a compound of Formula I from the corresponding compound of formula Ik in which $R^1$ is a group represented by formula (C) where X is N, $R^2$ and $R^4$ are hydrogen, and $R^9$ is benzene Step 1

A solution of 4-(piperidin-4-ylmethyl)-phenylamine (7.5 g, 39.44 mmol) in dry tetrahydrofuran (200 mL) was cooled in an ice bath under nitrogen atmosphere. Di-tert-butyl dicarbonate (9.76 g) was added to the solution in portions and stirred for 30 minutes. The resulting mixture was quenched with water, concentrated in vacuo, and extracted with ethyl acetate. The organic layer was washed with water and brine, dried, and solvents removed in vacuo. The crude product was chromatographed on a short silica gel column, eluting with 30% ethyl acetate/hexanes, to give 4-[1-(N-tert-butoxycarbonyi)piperidin-4-ylmethyl]-phenylamine (9.25 g, 81%) as an oil which solidifies, m.p. 91–92° C.

Step 2

A solution of 4-[1-(N-tert-butoxycarbonyl)piperidin-4-ylmethyl]-phenylamine (3.55 g, 12.24 mmol) and triethylamine (10.2 mL, 73.4 mmol) in dichloromethane (70 mL) was cooled in an ice bath under nitrogen atmosphere. Trifluoroacetic anhydride (5.2 mL, 36.7 mmol) was added dropwise to the solution. The resulting mixture was stirred for 30 minutes, quenched with pH 7.0 phosphate buffer (100 mL) and methanol (150 mL), and stirred at room temperature for 15 minutes. The reaction mixture was concentrated in vacuo, and the residue extracted into ethyl acetate. The organic layer was washed with cold water and brine, dried, and solvents removed in vacuo. The crude product was chromatographed on silica gel, eluting with 30% ethyl acetate/hexanes, to give 2,2,2-trifluoro-N-{4-[1-(N-tert-butoxycarbonyl)-piperidin-4-ylmethyl]-phenyl}acetamide (4.43 g, 94%) as a solid, m.p. 145–146° C.; Analysis for $C_{19}H_{25}N_2O_3F_3$: Calc.: C, 59.06; H, 6.52; N, 7.25; Found: C. 59.40; H, 6.54; N, 7.42.

Step 3

A mixture of 2,2,2-trifluoro-N-{4-[1-(N-tert-butoxycarbonyl)piperidin-4-ylmethyl]-phenyl}acetamide (3.3 g) and trifluoroacetic acid (5 mL) in dichloromethane (30 mL) was stirrred at room temperature for 2 hours. The reaction mixture was diluted with dichloromethane and cold water, and neutralized with sodium bicarbonate solution. The organic layer was separated, washed with water and brine, dried, and solvents removed in vacuo to give 2,2,2-trifluoro-N-[4-(piperidin-4-ylmethyl)-phenyl]acetamide (1.5 g) as a foam.

Step 4

A mixture of 2,2,2-trifluoro-N-[4-(piperidin4-ylmethyl)-phenyl]acetamide (0.5 g, 1.75 mmol) and triethylamine (0.23 g, 2.1 mmol) in dichloromethane (10 mL) was cooled in an ice bath under nitrogen atmosphere. A solution of benzenesulfonyl chloride (0.37 g, 2.1 mmoL) in dichloromethane (1 mL) was added under to the mixture while stirring. After 2 hours, the reaction mixture was quenched with water. The separated organic layer was washed with cold water and brine, dried, and solvents removed in vacuo. The residue was crystallized from ethyl acetate/hexanes to give 2,2,2-trifluoro-N-[4-(1-benzenesulfonyl-piperidin-4-ylmethyl)-phenyl]acetamide (0.43 g, 57%), m.p. 194–195° C.; Analysis for $C_{20}H_{21}N_2O_3SF_3$: Calc.: C, 56.32; H, 4.96; N, 6.57; Found: C, 56.54; H, 4.99; N, 6.68.

Step 5

A mixture of 2,2,2-trifluoro-N-[4-(1-benzenesulfonylpiperidin-4-ylmethyl)-phenyl]acetamide (0.45 g) and lithium hydroxide (0.23 g) in methanol (10 mL) and water (1 mL) was stirred for about 48 hours. The reaction mixture was concentrated in vacuo, diluted with cold water, and extracted with dichloromethane. The organic layer was washed with cold water and brine, dried, and solvents removed in vacuo. The residue was crystallized from ethyl acetate/hexanes to give 4-(1-benzenesulfonylpiperidin-4-ylmethyl)-phenylamine (0.29 g, 83%), m.p. 158° C.; Analysis for $C_{18}H_{22}N_2O_2S$: Calc.: C, 65.43; H, 6.71; N, 8.48; Found: C, 65.59; H, 6.61; N, 8.66.

Last Step

A mixture of 4-(1-benzenesulfonylpiperidin-4-ylmethyl)-phenylamine (0.28 g, 0.83 mmol) and 2-chloro-2-imidazoline sulfate (0.25 g, 1.25 mmol) in 2-propanol (20 mL) was heated under reflux for 30 minutes under nitrogen atmosphere. The reaction mixture was concentrated in vacuo. The residue was basified with 10% sodium hydroxide solution and extracted with dichloromethane. The organic layer was washed with cold water and brine, dried, and solvents removed in vacuo. The residue was chromatographed on neutral aluminum oxide, eluting with 1% methanol/dichloromethane, to give 2-[4-(1-benzenesulfonylpiperidin-4-ylmethyl)-phenyl]amino-imidazoline (0.29 g, 89%) as a foam. Analysis for $C_{21}H_{26}N_4O_2S.5H_2O$: Calc.: C, 61.89; H, 6.68; N, 13.75; Found: C, 62.00; H, 6.52; N, 13.85.

Proceeding as described in Example 19, step 4, but replacing benzenesulfonyl chloride with other sulfonyl chlorides or carbonyl chlorides, and then correspondingly as in Example 19, subsequent steps, other compounds of Formula I were prepared:

2-[4-(1-methanesulfonylpiperidin-4-ylmethyl)phenyl]amino-imidazoline hydrochloride; Analysis for $C_{16}H_{25}N_4O_2ClS$;

2-[4-(1-isopropylsulfonylpiperidin-4-ylmethyl)phenyl]amino-imidazoline; Analysis for $C_{18}H_{28}N_4O_2S.4H_2O$: Calc.: C, 58.16; H, 7.81; N, 15.07; Found: C, 58.26; H, 7.52; N, 14.96;

2-[4-(1-isopropylcarbonylpiperidin-4-ylmethyl)phenyl]amino-imidazoline, m.p. 193–194° C.; Analysis for $C_{19}H_{28}N_4O$: Calc.: C, 69.48; H, 8.59; N, 17.06; Found: C, 69.41; H, 8.59; N, 16.95;

2-[4-(1-isobutylcarbonylpiperidin-4-ylmethyl)phenyl]amino-imidazoline, m.p. 122–125° C.; MS m/z, 343 (M+1); and 2-{4-[1-(3-methylbutylcarbonyl)piperidin-4-ylmethyl]phenyl}amino-imidazoline hydrochloride, m.p. 155–157° C.; Analysis for $C_{21}H_{33}N_4OCl$: Calc.: C, 64.19; H, 8.46; N, 14.26; Found: C, 64.05; H, 8.39; N, 14.27.

Example 20

2-{4-[1-(1-Piperidinesulfonyl)piperidin-4-ylmethyl]-phenyl}amino-imidazoline

The following is an alternative preparation of a compound of Formula I from the corresponding compound of formula II in which $R^1$ is a group represented by formula (C) where X is N, $R^2$ and $R^4$ are hydrogen, and $R^8$ and $R^9$ together with the nitrogen to which they are attached form piperidine.

Step 4

A solution of 2,2,2-trifluoro-N-[4-(piperidin-4-ylmethyl)-phenyl]acetamide (0.5 g, 1.75 mmol) (prepared as previously described in Example 19, steps 1 to 3) and triethylamine in dichloromethane (10 mL) was cooled in an ice bath under a nitrogen atmosphere. The mixture was then treated with a solution of 1-piperidinesulfonyl chloride (0.39 g, 2.09 mmol) in dichloromethane (1 mL). The reaction mixture was stirred for 1.5 hours at 0–5° C. and quenched with water. The organic layer was separated, and the aqueous layer extracted with dichloromethane. The combined organic extracts were washed with water and brine, dried, and solvents removed in vacuo. The residue was chromatographed on silica gel, eluting with 30% ethyl acetate/hexanes, to give 2,2,2-trifluoro-N-[4-(1-piperidinesulfonylpiperidin-4-ylmethyl)-phenyl]acetamide (0.48 g) as a white solid, m.p. 156–157° C.; Analysis for $C_{19}H_{26}N_3O_3SF_3$: Calc.: C, 52.64; H, 6.05; N, 9.69; Found: C, 52.84; H, 6.00; N, 9.79.

Step 5

A mixture of 2,2,2-trifluoro-N-[4-(1-piperidinesulfonylpiperidin-4-ylmethyl)-phenyl]acetamide (0.48 g, 1.11 mmol) and lithiumhydroxide (0.23 g, 5.54 mmol) in methanol (10 mL) and water (1 mL) was heated at 60° C. for about 2 hours. The reaction mixture was concentrated in vacuo, diluted with water, and extracted with dichloromethane. The organic extracts were washed with water and brine, and dried ($Na_2SO_4$). The residue was crystallized from ethyl acetate/hexanes, to give 4-(1-piperidinesulfonylpiperidin-4-ylmethyl)-phenylamine (0.30 g) as a white solid, m.p. 144–145° C.; Analysis for $C_{17}H_{27}N_3O_2S$: Calc.: C, 60.50; H, 8.06; N, 12.45; Found: C, 60.76; H, 8.07; N, 12.56.

Last Step

Proceeding as previously described in Example 19, last step, gave 2-[4-(1-piperidinesulfonylpiperidin-4-ylmethyl)-phenyl]amino-imidazoline (0.29 g, 89%) as a foam. Analysis for $C_{20}H_{31}N_5O_2S$: Calc.: C, 59.23; H, 7.70; N, 17.27; Found: C, 59.13; H, 7.56; N, 17.13.

Proceeding as in Example 20, step 4, but replacing 1-piperidinesulfonyl chloride with 1-pyrrolidinesulfonyl chloride, and correspondingly as in Example 20, subsequent steps, gave 2-[4-(-pyrrolidinesufonylpiperidin-4-ylmethyl)-phenyl]amino-imidazoline as a foam; Analysis for $C_{19}H_{29}N_5O_2S$: Calc.: C, 57.23; H, 7.53; N, 17.56; Found: C, 57.27; H, 7.24; N, 17.40.

Example 21

X-Ray Diffraction Patterns of Crystal Form I

Crystal Form I of 2-[4-(4-Isopropoxybenzyl)phenyl]-amino-imidazoline sulfate is prepared by methods previously described in Example 1. The X-ray diffraction pattern shown in FIG. 1 was obtained utilizing a Scintag X1 powder X-ray diffractometer equipped with a copper Kα1 irradiation source. The numbers indicated in FIG. 1, top and lower abcissae indicate "d" spacing and 2θ, respectively; and right and left ordinates indicate relative intensities in % and counts per second (CPS), respectively.

The X-ray powder diffraction patterns given below are in terms of 'd' spacings and relative intensities (RI) above 3%. The weighted mean value of X-ray wavelength used for the calculations was $1.5406 \times 10^{-10}$ cm.

| d, $10^{-10}$ m | RI, % | d, $10^{-10}$ m | RI, % |
|---|---|---|---|
| 31.084 | 100 | 4.391 | 3 |
| 10.266 | 4 | 4.179 | 9 |
| 7.686 | 39 | 4.149 | 9 |
| 5.546 | 4 | 3.947 | 7 |
| 5.451 | 3 | 3.898 | 6 |
| 5.118 | 10 | 3.838 | 4 |
| 4.838 | 10 | 3.697 | 6 |
| 4.767 | 13 | 3.554 | 3 |
| 4.744 | 13 | 3.408 | 3 |

Example 22

Preparation of Crystal Form II

2-[4-(4-Isoproxybenzyl)phenyl]amino-imidazoline sulfate(194 mg) was dissolved in water (1 mL) at 60° C., and the clear supernatant was transferred into a Craig tube and cooled in an ice-water bath. Crystals were collected by centrifugation and dried under vacuum at ambient temperature to give Crystal Form II of 2-[4-(4-isopropoxybenzyl)phenyl]-amino-imidazoline sulfate (138 mg), m.p. 217–218° C.

Alternatively, 2-[4-(4-isoproxybenzyl)phenyl]amino-imidazoline sulfate(38 g) was dissolved in water (500 mL) at 80° C. After hot filtration, the solution was cooled to ambient temperature and stored at 4° C. for 5 hours. Crystals were collected by filtration and dried at ambient temperature to give Crystal Form II of 2-[4-(4-isopropoxy-benzyl)phenyl]-amino-imidazoline sulfate (33.6 g), m.p. 216–217° C.

Example 23

X-Ray Diffraction Patterns of Crystal Form II

Figure 2:
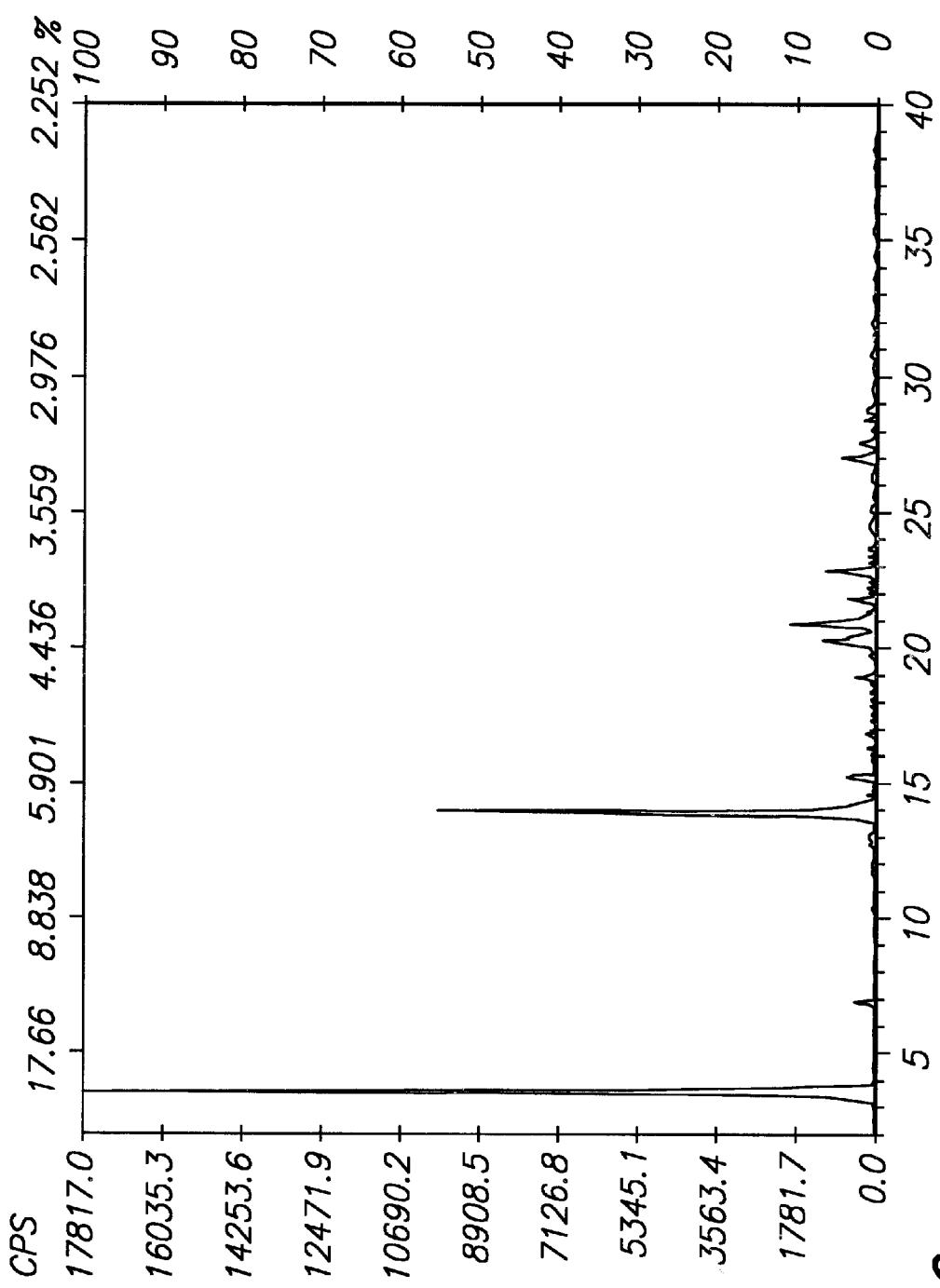
FIG. 2 shows the X-ray diffraction pattern of Crystal Form II of 2-[4-(4-isoproxybenzyl)phenyl]amino-imidazoline sulfate.

The X-ray diffraction pattern of Crystal Form II shown in FIG. 2 was obtained utilizing a Scintag X1 powder X-ray diffractometer equipped with a copper Kα1 irradiation source. The numbers indicated in FIG. 1, top and lower abcissae indicate "d" spacing and 2θ, respectively; and right and left ordinates indicate relative intensities in % and counts per second (CPS), respectively.

The X-ray powder diffraction patterns given below are in terms of 'd' spacings and relative intensities (RI) above 3%. The weighted mean value of X-ray wavelength used for the calculations was $1.5406 \times 10^{-10}$ cm.

| d, $10^{-10}$ m | RI, % | d, $10^{-10}$ m | RI, % |
|---|---|---|---|
| 25.664 | 100 | 4.258 | 9 |
| 12.756 | 3 | 4.086 | 3 |
| 6.386 | 49 | 3.910 | 4 |
| 4.397 | 7 | 3.307 | 4 |

Example 24

| Composition for Oral Administration | |
|---|---|
| The composition contains: | % wt./wt. |
| Active ingredient | 20.0% |
| Lactose | 79.5% |
| Magnesium stearate | 0.5% |

The two ingredients are mixed and dispersed into capsules containing 100 mg each; one capsule would approximate a total daily dosage.

Example 25

| Composition for Oral Administration | |
|---|---|
| The composition contains: | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The above ingredients are combined and granulated using methanol as solvent. The formulation is then dried and formed into tablets (containing 20 mg of active compound) with an appropriate tableting machine.

Example 26

| Parenteral Formulation (IV) | |
|---|---|
| The composition contains: | % wt./w. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 27

| Suppository Formulation | |
|---|---|
| The composition contains: | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 28

| Topical Formulation | |
|---|---|
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the above ingredients, except water, are combined and heated to 60° C. with stirring. A sufficient quantity of water at 60° C. is then added with vigorous stirring to emulsify the ingredients, and water then added q.s. 100 g.

Example 29

Nasal Spray Formulations

Several aqueous suspensions containing from 0.025–0.5 percent active compound are prepared as nasal spray formulations. The formulations optionally contain inactive ingredients such as microcrystalline cellulose, sodium carboxymethylcellulose, dextrose, and the like. Hydrochloric acid may be added to adjust pH. The nasal spray formulations may be delivered via a nasal spray metered pump typically delivering 50–100 microliters of formulation per actuation. A typical dosing schedule is 2–4 sprays every 4–12 hours.

Example 30

Carrageenan-Induced Mechanical Hyperalgesia Assay

The anti-inflammatory/analgesic activity of compounds of this invention was determined by the Carrageenan-Induced Mechanical Hyperalgesia Assay by measuring the inhibition of carrageenan-induced paw hyperalgesia in the rat, using a modification of the method described in L. O. Randall and J. J. Selitto, *Archives of International Pharmacodynamics*, 1957, 11, 409–419, and Vinegar et al., *Journal of Pharmacology and Experimental Therapeutics*, 1969, 166, 96–103.

Male Sprague-Dawley rats (130–150 g) were weighed and randomly assigned to treatment groups (n=10). To induce mechanical hyperalgesia, rats were lightly anesthetized with halothane and administered 1% carrageenan or vehicle 1 (100 µl) in the plantar surface of the left hindpaw. Rats were administered vehicle (10 ml/kg, p.o. or 1 ml/kg, i.v) or compounds of this invention (at 1, 3, 10, 30 and 100 mg/kg, p.o.) or (0.3, 1.0, 3.0 and 10 mg/kg, i.v.) one hour before testing. Mechanical hyperalgesia was measured using an Analgesy-meter (UGO BASILE, Biological-Research Apparatus, Comerio, Italy). The vehicle- or carrageenan-treated hindpaw was placed on the dome of the apparatus, plantar surface facing down. A constantly increasing force was then applied to the dorsal surface of the paw. The force at which the rat withdrew its paw, struggled, or vocalized was considered the end point.

Treatment groups were compared using a one-way analysis of variance on the paw withdrawal force (RESP). Pairwise comparisons for the drug-treated groups to the vehicle group were made using Fisher's LSD strategy and Dunn's procedure. Percent inhibition of mechanical hyperalgesia was calculated for each animal, and the average $ID_{50}$ value was estimated using the following sigmoidal model:

% inhibition $=100/(1+\exp((ID_{50}\text{-dose})/N))$ where $ID_{50}$ is the dose of the compound needed to inhibit half of the maximum response (ie., 100% in this model) and N is a curvature parameter.

The compounds of this invention were active in this assay.

Example 31

Complete Freund's Adjuvant-Induced Mechanical Hyperalgesia Assay

The anti-inflammatory/analgesic activity of compounds of this invention may also be determined using an adjuvant-induced arthritis pain model in the rat, whereas pain is assessed by the animal's response to the squeezing of the inflamed foot, using a modification of the method described in J. Hylden et al., *Pain* 1989, 37, 229–243. The modification includes the assessment of hyperalgesia instead of changes in activity of spinal cord neurons.

Briefly, rats were weighed and randomly assigned to treatment groups. To induce mechanical hyperalgesia, rats were lightly anesthetized with halothane and 100 µl of Complete Freund's Adjuvant or saline was administered into the plantar surface of the left hindpaw. Twenty-four hours later, water (vehicle) or compounds of this invention were orally administered to the rats one hour before testing. Mechanical hyperalgesia was measured using an Analgesy-meter (UGO BASILE, Biological Research Apparatus, Comerio, Italy). The saline or carrageenan-treated hindpaw was placed on the dome of the apparatus, plantar surface facing down. A constantly increasing force was then applied to the dorsal surface of the paw, and the force at which the rat withdrew its paw, struggled, or vocalized was considered the end point. The treatment groups were compared using a one-way analysis of variance on the paw withdrawal force. Percent inhibition was calculated for each animal in the form:

$100\times((c/d-c/v)+(s/v-c/v))$ where c/d is the paw withdrawal force for the carrageenan-treated paw in an animal to which drug has been administered; c/v is the paw withdrawal force for the carrageenan-treated paw in an animal to which vehicle has been administered; and s/v is the paw withdrawal force for the saline-treated paw in an animal to which vehicle has been administered. Significance was determined using Student's t-test.

The compounds of the invention were active in this assay.

Example 32

Inhibition of Bladder Contractions Induced by Isovolumetric Bladder Distension in Rats The inhibition of bladder contractions was determined by an assay using a modification of the method described in C. A. Maggi et al., *J. Pharm. and Exper. Therapeutics*, 1984, 230, 500–513.

Briefly, male Sprague-Dawley rats (200–250 g) were weighed and randomly assigned to treatment groups. A catheter was inserted through the urethra into the bladder to induce bladder contractions, and a warm saline solution (5 mL) was infused. Rhythmic contractions were produced in about 30% of the animals. The compounds of the invention (0.1, 0.3 or 1 mg/kg) were administered intravenous at the onset of regular rhythmic contractions. The effects on rhythmic contracts were then measured.

The compounds of this invention were active in this assay.

Example 33

Inhibition of Volume-Induced Contractions in Rats

The inhibition of bladder contractions was determined by an assay using a modification of the method described in S. S. Hegde et al., *Proceedings of the 26th Annual Meeting of the International Continence Society* (Aug. 27th–30th) 1996, Abstract 126.

Female Sprague-Dawley rats were anesthetized with urethane and instrumented for intravenous administration of drugs and, in some cases, measurement of arterial pressure, heart rate and intra-bladder pressure. The effect of test compounds on volume-induced bladder contractions was determined in separate groups of animals. Volume-induced reflex bladder contractions were induced by filling the bladder with saline. The test compounds were administered intravenously in a cumulative manner at 10-minute intervals. Atropine (0.3 mg/kg, iv) was administered at the end of the study as a positive control.

The compounds of this invention were active in this assay.

Example 34

Reversal of Endotoxin-Induced Hypotension in Rats

Septic shock, sometimes referred to as endotoxic shock, is caused by the presence of infectious agents, particularly bacterial endotoxins, in the bloodstream and is characterized by hypotension and organ dysfunction. Many symptoms of septic shock, in particular, hypotension, are induced in the rat by the administration of bacterial endotoxins. The ability of a compound to inhibit endotoxin-induced hypotension is therefore predictive of the utility of the compound in the treatment of septic or endotoxic shock.

The activity of the compounds of the invention in the treatment of septic or endotoxic shock was Determined by measuring the reversal of endotoxin-induced hypotension in the rat, using a modification A the method described in M. Giral et al., *British Journal of Pharmacology*, 1969, 118, 1223–1231.

Briefly, adult rats (>200 g) were anesthetized with an inhalation anesthetic and femoral arteries and veins were cannulated for insertion of blood pressure transducers and drug administration lines, respectively. They were placed in Mayo restrainers while still under the influence of the anesthetic. After recovery from anesthesia and stabilization of heart rate and blood pressure (which typically required about 30 minutes), endotoxin (50 mg/kg *E. coli* and mg/kg *Salmonella*) was administered intravenously. Changes in blood pressure and heart rate were monitored. After one hour, compounds of this invention or vehicle were also administered intravenously, and cardiovascular parameters were continuously monitored for the next three hours. Responses are represented as percentage return to initial diastolic blood pressure. Significance was determined using Student's t-test.

The compounds of this invention were active in this assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound selected from the group of compounds represented by Formula I:

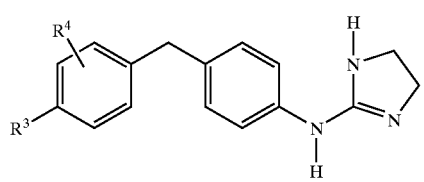

wherein

R$^3$ is selected from the group consisting of —(CH$_2$)$_m$OY wherein m is an integer from 0 to 3, and Y is selected from the group consisting of cycloalkyl and heterocyclyl, and R$^4$ is selected from the group consisting of hydrogen and halogen; or pharmaceutically acceptable salts thereof.

2. The compound of claim 1, wherein Y is cycloalkyl.
3. The compound of claim 2, wherein R$^4$ is hydrogen.
4. The compound of claim 2, wherein R$^4$ is a halogen.
5. The compound of claim 1, wherein Y is heterocyclyl.
6. The compound of claim 5, wherein R$^4$ is hydrogen.
7. The compound of claim 5, wherein R$^4$ is a halogen.
8. The compound of claim 1, wherein said compound is selected from the group consisting of:

2-[4-(4-cyclopentyloxybenzyl)phenyl]amino-imidazoline;

2-[4-(4-cyclohexyloxybenzyl)phenyl]amino-imidazoline;

2-[4-(4-cyclohexylmethoxybenzyl)phenyl]amino-imidazoline;

2-{4-[4-(2-(pyrrolidin-2-one)ethoxy)benzyl]phenyl}amino-imidazoline;

2-{4-[4-(tetrahydropyran-4-yloxy)benzyl]phenyl}amino-imidazoline;

2-{4-[4-(2-cyclohexylethoxy)benzyl]phenyl}amino-imidazoline;

2-{4-[4-(tetrahydropyran-4-ylmethoxy)benzyl]phenyl}amino-imidazoline;

2-{4-[4-(tetrahydropyran-2-ylmethoxy)benzyl]
phenyl}amino-imidazoline;

2-{4-[4-(2-(imidazolin-2-one)ethoxy)benzyl]
phenyl}amino-imidazoline;

2-[4-(2-cyclopentylethoxybenzyl)phenyl]amino-
imidazoline;

2-[4-(4-cyclobutylmethoxybenzyl)phenyl]amino-
imidazoline;

2-[4-(4-cyclopropylmethoxybenzyl)phenyl]amino-
imidazoline;

2-{4-[2-fluoro-4-(tetrahydropyran-4-yloxy)benzyl]
phenyl}amino-imidazoline;

2-{4-[2-fluoro-4-(tetrahydropyran-2-ylmethoxy)benzyl]
phenyl}amino-imidazoline;

2-{4-[3-chloro4-(tetrahydropyran-4-yloxy)benzyl]
phenyl}amino-imidazoline;

2-{4-[3-fluoro-4-(tetrahydropyran-4-yloxy)benzyl]
phenyl}amino-imidazoline;

2-{4-[3-fluoro-4-(tetrahydropyran-4-ylmethoxy)benzyl]
phenyl}amino-imidazoline;

2-{4-[3-chloro4-(tetrahydropyran4-ylmethoxy)benzyl]
phenyl}amino-imidazoline; and 2-{4-[4-(tetrahydrofuran-3-yloxy)benzyl]phenyl}amino-
imidazoline.

9. The compound of claim 1, wherein said compound is selected from the group consisting of:

2-[4-(4-cyclopentyloxybenzyl)phenyl]amino-
imidazoline;

2-[4-(4-tetrahydropyran-4-yloxybenzyl)phenyl]amino-
imidazoline;

2-{4-[4-(tetrahydropyran-4-ylmethoxy)benzyl]
phenyl}amino-imidazoline; and

2-{4-[4-(tetrahydrofuran-2-ylmethoxy)benzyl]
phenyl}amino-imidazoline.

* * * * *